US012760359B2

(12) United States Patent
Barad et al.

(10) Patent No.: US 12,760,359 B2
(45) Date of Patent: Oct. 13, 2026

(54) METHODS AND SYSTEMS FOR DETERMINING SEQUENCING READ DISTANCES

(71) Applicant: Ultima Genomics, Inc., Newark, CA (US)

(72) Inventors: Omer Barad, Mazkeret Batya (IL); Yoav Etzioni, Tel Aviv (IL)

(73) Assignee: Ultima Genomics, Inc., Fremont, CA (US)

( * ) Notice: Subject to any disclaimer, the term of this patent is extended or adjusted under 35 U.S.C. 154(b) by 694 days.

(21) Appl. No.: 18/035,081

(22) PCT Filed: Nov. 3, 2021

(86) PCT No.: PCT/US2021/072219
§ 371 (c)(1),
(2) Date: May 2, 2023

(87) PCT Pub. No.: WO2022/099271
PCT Pub. Date: May 12, 2022

(65) Prior Publication Data

US 2024/0043918 A1 Feb. 8, 2024

Related U.S. Application Data

(60) Provisional application No. 63/109,819, filed on Nov. 4, 2020.

(51) Int. Cl.
*C12Q 1/6869* (2018.01)
*C12Q 1/6809* (2018.01)

(52) U.S. Cl.
CPC ......... *C12Q 1/6869* (2013.01); *C12Q 1/6809* (2013.01)

(58) Field of Classification Search
CPC ............ C12Q 1/6869; C12Q 2533/101; C12Q 2535/113; C12Q 2537/157; C12Q 2563/107; C12Q 1/6809
See application file for complete search history.

(56) References Cited

U.S. PATENT DOCUMENTS

| | | | |
|---|---|---|---|
| 5,714,320 | A | 2/1998 | Kool |
| 8,364,417 | B2 | 1/2013 | Chen |
| 8,772,473 | B2 | 7/2014 | Huang |
| 9,428,807 | B2 | 8/2016 | Hubbell |
| 9,587,274 | B2 | 3/2017 | Chen |
| 9,817,944 | B2 | 11/2017 | Kural |
| 10,192,024 | B2 | 1/2019 | Chen |
| 10,344,328 | B2 | 7/2019 | Barbee |
| 11,220,709 | B2 | 1/2022 | Oberstrass et al. |
| 11,220,710 | B2 | 1/2022 | Oberstrass et al. |
| 11,459,609 | B2 | 10/2022 | Pratt et al. |
| 11,462,300 | B2 | 10/2022 | Bartov et al. |
| 11,578,363 | B2 | 2/2023 | Oberstrass et al. |
| 11,763,915 | B2 | 9/2023 | Etzioni et al. |
| 12,209,278 | B2 | 1/2025 | Pratt et al. |
| 12,482,536 | B2 | 11/2025 | Etzioni et al. |
| 2009/0053724 | A1 | 2/2009 | Roth |
| 2010/0093986 | A1 | 4/2010 | Zwick et al. |
| 2010/0173303 | A1 | 7/2010 | Ronaghi et al. |
| 2011/0270533 | A1 | 11/2011 | Zhang |
| 2012/0252682 | A1 | 10/2012 | Zhou et al. |
| 2013/0090860 | A1 | 4/2013 | Sikora |
| 2013/0281306 | A1 | 10/2013 | Rigatti et al. |
| 2014/0052381 | A1 | 2/2014 | Utiramerur |
| 2014/0315724 | A1* | 10/2014 | Zhou .................... C12Q 1/6869 435/6.1 |
| 2015/0066824 | A1 | 3/2015 | Harris |
| 2015/0203910 | A1 | 7/2015 | Smith et al. |
| 2016/0110499 | A1 | 4/2016 | Donnet |
| 2016/0326579 | A1 | 11/2016 | Olejnik |
| 2017/0044601 | A1 | 2/2017 | Crnogorac |
| 2017/0335387 | A1 | 11/2017 | Brinza |
| 2018/0330051 | A1 | 11/2018 | Hubbell |
| 2018/0363047 | A1 | 12/2018 | Smith |
| 2019/0360034 | A1 | 11/2019 | Zhou et al. |
| 2020/0002764 | A1 | 1/2020 | Belgrader et al. |
| 2020/0199666 | A1 | 6/2020 | Gatti-Lafranconi et al. |
| 2020/0372971 | A1 | 11/2020 | Etzioni |
| 2020/0377937 | A1 | 12/2020 | Pratt |

(Continued)

FOREIGN PATENT DOCUMENTS

| | | | |
|---|---|---|---|
| KR | 2018-0055905 | A | 5/2018 |
| WO | 1998/44152 | A1 | 10/1998 |

(Continued)

OTHER PUBLICATIONS

Ali, M.M. et al. (2014). "Rolling Circle Amplification: A Versatile Tool for Chemical Biology, Materials Science and Medicine," Chem. Soc. Rev. 43:3324, 19 pages.
Chaisson, M.J. et al. (2009). "De Novo Fragment Assembly With Short Mate Paired Reads: Does the Read Length Matter?," Genome Research 19:336-346.
Dean, F.B. et al. (2001). "Rapid Amplification of Plasmid and Phage DNA Using Phi29 DNA Polymerase and Multiply-Primed Rolling Circle Amplification," Genome Research 11:1095-1099.
Depristo, M.A. et al. (May 2011, e-pub. Nov. 1, 2011). "A Framework for Variation Discovery and Genotyping Using Next-Generation DNA Sequencing Data," Nature Genetics 43(5):491-498, 20 pages.
Hwang, S. et al. (Dec. 7, 2015). "Systematic Comparison of Variant Calling Pipelines Using Gold Standard Personal Exome Variants," Sci Rep. 5(17875):1-8.

(Continued)

*Primary Examiner* — Joseph G. Dauner
(74) *Attorney, Agent, or Firm* — MORRISON & FOERSTER LLP

(57) ABSTRACT

Described herein are methods of sequencing a polynucleotide and methods of analyzing sequencing data obtained from such sequencing methods. The sequencing methods can include accelerated primer extension through a region of the polynucleotide using labeled nucleotides provided according to a flow order, measuring a signal from labeled nucleotides incorporated into the primer, and determining distance information that indicates the length of the region using the measured signal.

21 Claims, 17 Drawing Sheets

Specification includes a Sequence Listing.

(56) References Cited

U.S. PATENT DOCUMENTS

| | | | |
|---|---|---|---|
| 2020/0392584 | A1 | 12/2020 | Almogy |
| 2021/0010075 | A1 | 1/2021 | Oberstrass |
| 2021/0054442 | A1 | 2/2021 | Pratt et al. |
| 2021/0147930 | A1 | 5/2021 | Oberstrass et al. |
| 2021/0147931 | A1 | 5/2021 | Oberstrass et al. |
| 2021/0366576 | A1 | 11/2021 | Bartov et al. |
| 2022/0170089 | A1 | 6/2022 | Pratt et al. |
| 2023/0060685 | A1 | 3/2023 | Pratt et al. |
| 2023/0197197 | A1 | 6/2023 | Bartov et al. |
| 2023/0313289 | A1 | 10/2023 | Oberstrass et al. |
| 2023/0343416 | A1 | 10/2023 | Etzioni et al. |
| 2023/0407385 | A1 | 12/2023 | Barad et al. |
| 2024/0018599 | A1 | 1/2024 | Barad et al. |
| 2024/0120025 | A1 | 4/2024 | Etzioni et al. |
| 2024/0287483 | A1 | 8/2024 | Mazur et al. |
| 2024/0309445 | A1 | 9/2024 | Oberstrass et al. |
| 2025/0197928 | A1 | 6/2025 | Pratt et al. |

FOREIGN PATENT DOCUMENTS

| | | | | |
|---|---|---|---|---|
| WO | 199844151 | A1 | 10/1998 | |
| WO | WO-2010075188 | A2 * | 7/2010 | ........... C12Q 1/6869 |
| WO | 2012134602 | A2 | 10/2012 | |
| WO | 2012166742 | A2 | 12/2012 | |
| WO | 2012166742 | A3 | 4/2013 | |
| WO | 2012134602 | A3 | 12/2013 | |
| WO | 2017/062863 | A1 | 4/2017 | |
| WO | 2019084158 | A1 | 5/2019 | |
| WO | 2019099886 | A1 | 5/2019 | |
| WO | 2019191003 | A1 | 10/2019 | |
| WO | 2020172197 | A1 | 8/2020 | |
| WO | 2020185790 | A1 | 9/2020 | |
| WO | 2020186243 | A1 | 9/2020 | |
| WO | 2020227137 | A1 | 11/2020 | |
| WO | 2020227143 | A1 | 11/2020 | |
| WO | 2020236630 | A1 | 11/2020 | |
| WO | 2020240025 | A1 | 12/2020 | |
| WO | 2021007495 | A1 | 1/2021 | |
| WO | 2022051296 | A1 | 3/2022 | |
| WO | 2022056296 | A1 | 3/2022 | |
| WO | 2022099270 | A1 | 5/2022 | |
| WO | 2022109574 | A1 | 5/2022 | |
| WO | 2022204685 | A1 | 9/2022 | |
| WO | 2023004421 | A1 | 1/2023 | |
| WO | 2023288319 | A1 | 1/2023 | |
| WO | 2023010069 | A1 | 2/2023 | |
| WO | 2023010131 | A1 | 2/2023 | |
| WO | 2023060091 | A1 | 4/2023 | |
| WO | 2023081653 | A1 | 5/2023 | |
| WO | 2023081883 | A2 | 5/2023 | |
| WO | 2023081883 | A3 | 6/2023 | |
| WO | 2023141430 | A1 | 7/2023 | |
| WO | 2023164505 | A2 | 8/2023 | |
| WO | 2023164505 | A3 | 10/2023 | |
| WO | 2024/102889 | A1 | 5/2024 | |

OTHER PUBLICATIONS

International Preliminary Report on Patentability, issued May 8, 2023, for PCT Application No. PCT/US2021/072219, filed Nov. 2021, 12 pages.
International Search Report and Written Opinion, mailed Feb. 2, 2022, for PCT Application No. PCT/US2021/072219, filed Nov. 3, 2021, 16 pages.
Mielczarek, M. et al. (2016). "Review of Alignment and SNP Calling Algorithms for Next-Generation Sequencing Data," J. Appl. Genetics 57:71-79.
Miller, J.R. et al. (2010, e-pub. Mar. 6, 2010). "Assembly Algorithms for Next-Generation Sequencing Data," Genomics 95:315-327.
Mitra, R.B. et al. (2003). "Fluorescent in Situ Sequencing on Polymerase Colonies," Analytical Biochemistry 320:55-65.
Nielsen, R. et al. (Jun. 2011). "Genotype and SNP Calling From Next-Generation Sequencing Data," Nature Reviews Genetics 12(6):443-451, 20 pages.
Partial Supplementary European Search Report, dated Jul. 7, 2023, for European Patent Application No. 20801590.9, 19 pages.
Peng, Q. et al. (2019, e-pub. Mar. 18, 2019). "Targeted Single Primer Enrichment Sequencing with Single End Duplex-UMI," Scientific Reports 9(4810):1-10.
Poplin, R. et al. (Jul. 24, 2018, e-pub. Nov. 14, 2017). "Scaling Accurate Genetic Variant Discovery to Tens of Thousands of Samples," BioRxiv, located at a https://www.biorxiv.org/content/biorxiv/early/2017/11/14/201178.1.full.pdf last visited on Aug. 7, 2020, 22 pages.
Somervuo, P. et al. (2018). "Barcosel: A Tool for Selecting an Optimal Barcode Set for High-Throughput Sequencing," BMC Bioinformatics 19:257, 6 pages.
Van Dijk, E.L. et al. (2018). "The Third Revolution in Sequencing Technology," Trends in Genetics 34(9):666-681.
Zerbino, D.R. et al. (2008, e-pub. Mar. 18, 2008). "Velvet: Algorithms for De Novo Short Read Assembly Using De Bruijn Graphs," Genome Research 18:821-829, 11 pages.
Zook, J. M. et al. (Apr. 1, 2019). "An Open Resource for Accurately Benchmarking Small Variant and Reference Calls," Nature Biotechnology 37:561-566, 14 pages.

* cited by examiner

| Base Count | Cycle 1 | | | | Cycle 2 | | | | Cycle 3 | | | | Cycle 4 | | | | Cycle 5 | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| | T | A | C | G | T | A | C | G | T | A | C | G | T | A | C | G | T | A | C | G |
| 0 | 0.0010 | 0.0010 | 0.9988 | 0.9988 | 0.0010 | 0.9988 | 0.9988 | 0.0001 | 0.0010 | 0.9988 | 0.0010 | 0.0010 | 0.0010 | 0.9988 | 0.0010 | 0.0010 | 0.9988 | 0.0010 | 0.9988 | 0.9988 |
| 1 | 0.9979 | 0.9979 | 0.0010 | 0.0010 | 0.9979 | 0.0010 | 0.0010 | 0.0010 | 0.9979 | 0.0010 | 0.9979 | 0.9979 | 0.9979 | 0.0010 | 0.9979 | 0.9979 | 0.0010 | 0.9979 | 0.0010 | 0.0010 |
| 2 | 0.0010 | 0.0010 | 0.0001 | 0.0001 | 0.0010 | 0.0001 | 0.0001 | 0.9979 | 0.0010 | 0.0001 | 0.0010 | 0.0010 | 0.0010 | 0.0001 | 0.0010 | 0.0010 | 0.0001 | 0.0010 | 0.0001 | 0.0001 |
| 3 | 0.0001 | 0.0001 | 0.0001 | 0.0001 | 0.0001 | 0.0001 | 0.0001 | 0.0010 | 0.0001 | 0.0001 | 0.0001 | 0.0001 | 0.0001 | 0.0001 | 0.0001 | 0.0001 | 0.0001 | 0.0001 | 0.0001 | 0.0001 |

*FIG. 14A*

| Base Count | Cycle 1 | | | | Cycle 2 | | | | Cycle 3 | | | | Cycle 4 | | | | Cycle 5 | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| | T | A | C | G | T | A | C | G | T | A | C | G | T | A | C | G | T | A | C | G |
| 0 | 0.0010 | 0.0010 | 0.9988 ★ | 0.9988 ★ | 0.0010 | 0.9988 ★ | 0.9988 ★ | 0.0001 | 0.0010 | 0.9988 ★ | 0.0010 | 0.0010 | 0.0010 | 0.9988 ★ | 0.0010 | 0.0010 | 0.9988 ★ | 0.0010 | 0.9988 ★ | 0.9988 ★ |
| 1 | 0.9979 ★ | 0.9979 ★ | 0.0010 | 0.0010 | 0.9979 ★ | 0.0010 | 0.0010 | 0.0010 | 0.9979 ★ | 0.0010 | 0.9979 ★ | 0.9979 ★ | 0.9979 ★ | 0.0010 | 0.9979 ★ | 0.9979 ★ | 0.0010 | 0.9979 ★ | 0.0010 | 0.0010 |
| 2 | 0.0010 | 0.0010 | 0.0001 | 0.0001 | 0.0010 | 0.0001 | 0.0001 | 0.9979 ★ | 0.0010 | 0.0001 | 0.0010 | 0.0010 | 0.0010 | 0.0001 | 0.0010 | 0.0010 | 0.0001 | 0.0010 | 0.0001 | 0.0001 |
| 3 | 0.0001 | 0.0001 | 0.0001 | 0.0001 | 0.0001 | 0.0001 | 0.0001 | 0.0010 | 0.0001 | 0.0001 | 0.0001 | 0.0001 | 0.0001 | 0.0001 | 0.0001 | 0.0001 | 0.0001 | 0.0001 | 0.0001 | 0.0001 |

*FIG. 14B*

| Base Count | Cycle 1 | | | | Cycle 2 | | | | Cycle 3 | |
|---|---|---|---|---|---|---|---|---|---|---|
| | 1 | 2 | 3 | 4 | 5 | 6 | 7 | 8 | 9 | 10 |
| | T | A | C | G | T | A | C | G | T | A |
| 0 | 0.0010 | 0.0010 | 0.9988 | 0.9988 | 0.0010 | 0.9988 | 0.9988 | 0.0001 | 0.0010 | 0.9988 |
| 1 | 0.9979 | 0.9979 | 0.0010 | 0.0010 | 0.9979 | 0.0010 | 0.0010 | 0.0010 | 0.9979 | 0.0010 |
| 2 | 0.0010 | 0.0010 | 0.0001 | 0.0001 | 0.0010 | 0.0001 | 0.0001 | 0.9979 | 0.0010 | 0.0001 |
| 3 | 0.0001 | 0.0001 | 0.0001 | 0.0001 | 0.0001 | 0.0001 | 0.0001 | 0.0010 | 0.0001 | 0.0001 |
| 1st Cand. Seq. | T | A | - | - | T | - | - | GG | T | - |
| 2nd Cand. Seq. | T | A | - | - | T | - | - | GG | T | - |

| Base Count | Cycle 3 | | Cycle 4 | | | | Cycle 5 | | | |
|---|---|---|---|---|---|---|---|---|---|---|
| | 11 | 12 | 13 | 14 | 15 | 16 | 17 | 18 | 19 | 20 |
| | C | G | T | A | C | G | T | A | C | G |
| 0 | 0.0010 | 0.0010 | 0.0010 | 0.9988 | 0.0010 | 0.0010 | 0.9988 | 0.0010 | 0.9988 | 0.9988 |
| 1 | 0.9979 | 0.9979 | 0.9979 | 0.0010 | 0.9979 | 0.9979 | 0.0010 | 0.9979 | 0.0010 | 0.0010 |
| 2 | 0.0010 | 0.0010 | 0.0010 | 0.0001 | 0.0010 | 0.0010 | 0.0001 | 0.0010 | 0.0001 | 0.0001 |
| 3 | 0.0001 | 0.0001 | 0.0001 | 0.0001 | 0.0001 | 0.0001 | 0.0001 | 0.0001 | 0.0001 | 0.0001 |
| 1st Cand. Seq. | C | - | - | A | - | - | T | - | C | G |
| 2nd Cand. Seq. | C | G | T | - | C | G | - | A | - | - |

FIG. 14C

```
    TATGGTCGTCGA           R1
      TGGTCGTCGAGC         R2
  TATATGGTCGTC             R3
--------------------------------
  TATATGGTCATCGAGCTAT      H1
  TATATGGTCGTCGAGCTAT      H2
          ↑
```

*FIG. 15A*

R1 Sequencing Data Set

| Base Count | Cycle 1 | | | | Cycle 2 | | | | Cycle 3 | | | | Cycle 4 | | | | Cycle 5 | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| | T | A | C | G | T | A | C | G | T | A | C | G | T | A | C | G | T | A | C | G |
| 0 | 0.0010 | 0.0010 | 0.9988 ●○ | 0.9988 ●○ | 0.0010 | 0.9988 ●○ | 0.9988 ●○ | 0.0001 | 0.0010 | 0.9988 ●○ | 0.0010 | 0.0010 ● | 0.0010 ● | 0.9988 ○ | 0.0010 ● | 0.0010 ● | 0.9988 ○ | 0.0010 ● | 0.9988 ○ | 0.9988 ○ |
| 1 | 0.9979 ●○ | 0.9979 ●○ | 0.0010 | 0.0010 | 0.9979 ●○ | 0.0010 | 0.0010 | 0.0010 | 0.9979 ●○ | 0.0010 | 0.9979 ●○ | 0.9979 ○ | 0.9979 ○ | 0.0010 ● | 0.9979 ○ | 0.9979 ○ | 0.0010 ● | 0.9979 ○ | 0.0010 ● | 0.0010 ● |
| 2 | 0.0010 | 0.0010 | 0.0001 | 0.0001 | 0.0010 | 0.0001 | 0.0001 | 0.9979 ●○ | 0.0010 | 0.0001 | 0.0010 | 0.0010 | 0.0010 | 0.0001 | 0.0010 | 0.0010 | 0.0001 | 0.0010 | 0.0001 | 0.0001 |
| 3 | 0.0001 | 0.0001 | 0.0001 | 0.0001 | 0.0001 | 0.0001 | 0.0001 | 0.0010 | 0.0001 | 0.0001 | 0.0001 | 0.0001 | 0.0001 | 0.0001 | 0.0001 | 0.0001 | 0.0001 | 0.0001 | 0.0001 | 0.0001 |

*FIG. 15B*

R2 Sequencing Data Set

| Base Count | Cycle 1 | | | | Cycle 2 | | | | Cycle 3 | | | | Cycle 4 | | | | Cycle 5 | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| | T | A | C | G | T | A | C | G | T | A | C | G | T | A | C | G | T | A | C | G |
| 0 | 0.0010 | 0.9979 ●○ | 0.9988 ●○ | 0.0001 | 0.0010 | 0.9988 ●○ | 0.0010 | 0.0010 ● | 0.0010 ● | 0.9988 ○ | 0.0010 ● | 0.0010 ● | 0.9988 ○ | 0.0010 ● | 0.9979 ○ | 0.0010 | 0.9988 ●○ | 0.9979 ○ | 0.0010 ● | 0.9988 ○ |
| 1 | 0.9979 ●○ | 0.0010 | 0.0010 | 0.0010 | 0.9979 ●○ | 0.0010 | 0.9988 ●○ | 0.9988 ○ | 0.9979 ○ | 0.0010 ● | 0.9979 ○ | 0.9979 ○ | 0.0010 ● | 0.9988 ○ | 0.0010 ● | 0.9979 ●○ | 0.0010 | 0.0010 ● | 0.9988 ○ | 0.0010 ● |
| 2 | 0.0010 | 0.0001 | 0.0001 | 0.9988 ●○ | 0.0010 | 0.0001 | 0.0010 | 0.0010 | 0.0010 | 0.0001 | 0.0010 | 0.0010 | 0.0001 | 0.0010 | 0.0001 | 0.0010 | 0.0001 | 0.0001 | 0.0010 | 0.0001 |
| 3 | 0.0001 | 0.0001 | 0.0001 | 0.0001 | 0.0001 | 0.0001 | 0.0001 | 0.0010 | 0.0001 | 0.0001 | 0.0001 | 0.0001 | 0.0001 | 0.0001 | 0.0001 | 0.0001 | 0.0001 | 0.0001 | 0.0001 | 0.0001 |

*FIG. 15C*

R3 Sequencing Data Set

| Base Count | Cycle 1 | | | | Cycle 2 | | | | Cycle 3 | | | | Cycle 4 | | | | Cycle 5 | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| | T | A | C | G | T | A | C | G | T | A | C | G | T | A | C | G | T | A | C | G |
| 0 | 0.0010 | 0.0010 | 0.9988 ●○ | 0.9988 ●○ | 0.0010 | 0.0010 | 0.9988 ●○ | 0.9988 ●○ | 0.0010 | 0.9988 ●○ | 0.9979 ●○ | 0.0001 | 0.0010 | 0.9988 ●○ | 0.0010 | 0.0010 ● | 0.0010 ● | 0.9979 ○ | 0.0010 ● | 0.9988 ●○ |
| 1 | 0.9979 ●○ | 0.9979 ●○ | 0.0010 | 0.0010 | 0.9979 ●○ | 0.9988 ●○ | 0.0010 | 0.0010 | 0.9979 ●○ | 0.0010 | 0.0010 | 0.0010 | 0.9988 ●○ | 0.0010 | 0.9979 ●○ | 0.9979 ○ | 0.9988 ○ | 0.0010 ● | 0.9988 ○ | 0.0010 |
| 2 | 0.0010 | 0.0010 | 0.0001 | 0.0001 | 0.0010 | 0.0010 | 0.0001 | 0.0001 | 0.0010 | 0.0001 | 0.0001 | 0.9979 ●○ | 0.0010 | 0.0001 | 0.0010 | 0.0010 | 0.0010 | 0.0001 | 0.0010 | 0.0001 |
| 3 | 0.0001 | 0.0001 | 0.0001 | 0.0001 | 0.0001 | 0.0001 | 0.0001 | 0.0010 | 0.0001 | 0.0001 | 0.0001 | 0.0010 | 0.0001 | 0.0001 | 0.0001 | 0.0001 | 0.0001 | 0.0001 | 0.0001 | 0.0001 |

*FIG. 15D*

| Base Count | Cycle 1 | | | | Cycle 2 | | | | Cycle 3 | | | | Cycle 4 | | | | Cycle 5 | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| | T | A | C | G | T | A | C | G | T | A | C | G | T | A | C | G | T | A | C | G |
| 0 | 0.0010 | 0.0010 | 0.9988 | 0.9988 | 0.0010 | 0.9988 | 0.9988 | 0.0001 | 0.0010 | 0.9988 | 0.0010 | 0.0010 | 0.9988 | 0.0010 | 0.9988 | 0.9988 | 0.0010 | 0.9988 | 0.0010 | 0.0010 |
| 1 | 0.9979 | 0.9979 | 0.0010 | 0.0010 | 0.9979 | 0.0010 | 0.0010 | 0.0010 | 0.9979 | 0.0010 | 0.9979 | 0.9979 | 0.0010 | 0.9979 | 0.0010 | 0.0010 | 0.9979 | 0.0010 | 0.9979 | 0.9979 |
| 2 | 0.0010 | 0.0010 | 0.0001 | 0.0001 | 0.0010 | 0.0001 | 0.0001 | 0.9979 | 0.0010 | 0.0001 | 0.0010 | 0.0010 | 0.0001 | 0.0010 | 0.0001 | 0.0001 | 0.0010 | 0.0001 | 0.0010 | 0.0010 |
| 3 | 0.0001 | 0.0001 | 0.0001 | 0.0001 | 0.0001 | 0.0001 | 0.0001 | 0.0010 | 0.0001 | 0.0001 | 0.0001 | 0.0001 | 0.0001 | 0.0001 | 0.0001 | 0.0001 | 0.0001 | 0.0001 | 0.0001 | 0.0001 |

*FIG. 16*

METHODS AND SYSTEMS FOR DETERMINING SEQUENCING READ DISTANCES

CROSS-REFERENCE TO RELATED APPLICATION

This application is a national stage application under 35 U.S.C. § 371 of International Application No. PCT/US2021/072219, filed internationally on Nov. 3, 2021, which claims priority to and the benefit of U.S. Provisional Application No. 63/109,819, filed Nov. 4, 2020, each of which is incorporated herein by reference for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165272000700SEQLIST.txt, date recorded: May 2, 2023, size: 4,217 bytes).

FIELD OF THE INVENTION

Described herein are methods of sequencing a polynucleotide, including methods for generating a coupled sequencing read pair, and methods of analyzing sequencing data obtained from the sequencing methods.

BACKGROUND

Paired-end sequencing methods have been used to obtain sequencing data for the 3' and 5' ends of a polynucleotide molecule. Generally, a sequencing primer is hybridized to a DNA polynucleotide to be sequenced, and several bases are sequenced to obtain sequencing data for the first end of the polynucleotide. A second sequencing primer is then hybridized to the complementary strand near the other end of the polynucleotide, and sequenced to determine sequencing data of the other end of the polynucleotide. The sequencing data for the 3' and 5' ends of the polynucleotide are coupled based on the fact that the sequencing data was obtained from the same sequencing cluster. Paired-end sequencing methods are frequently used in next-generation sequencing (NGS) protocols.

Using traditional paired-end sequencing, however, no (or very little) information is derived for the region between the 3' and 5' ends of a polynucleotide. Although the paired end sequencing data can be used for certain analytical purposes, it cannot be used to detect certain variants in the unsequenced region of the polynucleotide. Certain long-range sequencing techniques have been developed to sequence the region of the polynucleotide generally missed using traditional paired-end sequencing methods. However, long-range sequencing is relatively slow and prone to substantial sequencing errors.

BRIEF SUMMARY OF THE INVENTION

Described herein are methods of sequencing a polynucleotide and methods of analyzing sequencing data obtained from such sequencing methods. The sequencing methods can include accelerated primer extension through a region of the polynucleotide using labeled nucleotides provided according to a flow order, measuring a signal from labeled nucleotides incorporated into the primer, and determining distance information that indicates the length of the region using the measured signal.

A method of sequencing a polynucleotide can include hybridizing the polynucleotide to a primer to form a hybridized template; generating sequencing data associated with a sequence of a first region of the polynucleotide by extending the primer through the first region of the polynucleotide using labeled nucleotides (or the simultaneous use of labeled and unlabeled nucleotides) provided according to a first region flow order comprising a plurality of flow steps, and detecting the presence or absence of an incorporated labeled nucleotide after each flow step; extending the primer through a second region of the polynucleotide using labeled nucleotides provided according to a second region flow order comprising two or more flow steps; measuring a signal from the labeled nucleotides incorporated into the primer after the two or more flow steps of the second region flow order; and determining distance information indicative of the length of the second region using the measured signal. At least a portion of the two or more flow steps in the second region flow order can include the simultaneous use of two or more different nucleotide bases, or three or more different nucleotide bases. The primer can be extended through the second region without detecting incorporated labeled nucleotides after each flow step in the second region flow order. The labeled nucleotides include a label that need not be cleaved after each flow step in the second region flow order.

The method may include measuring a plurality of signals, wherein a signal is measured from labeled nucleotides incorporated into the primer after every two to five flow steps in the second region flow order; and determining the distance information using the plurality of signals. The labeled nucleotides may include label that is cleaved after measuring the signal after the every two to five flow steps in the second region flow order.

A first portion of the two or more flow steps in the second region flow order may include the use of only unlabeled nucleotides and a second portion of the two or more flow steps of the second region flow order can include the use of labeled nucleotides (or the simultaneous use of labeled nucleotides and unlabeled nucleotides). Alternatively, each of the two or more flow steps in the second region flow order can include the simultaneous use of labeled and unlabeled nucleotides.

In another method of sequencing a polynucleotide, the method includes: hybridizing the polynucleotide to a primer to form a hybridized template; generating sequencing data associated with a sequence of a first region of the polynucleotide by extending the primer through the first region of the polynucleotide using labeled nucleotides (or the simultaneous use of labeled and unlabeled nucleotides) provided according to a first region flow order comprising a plurality of flow steps, and detecting the presence or absence of an incorporated labeled nucleotide after each flow step; extending the primer through a second region of the polynucleotide using labeled nucleotides provided according to a second region flow order comprising a one or more flow steps, wherein at least one of the one or more flow steps comprises the simultaneous use of two or more different nucleotide bases; measuring a signal from labeled nucleotides incorporated into the primer after each of the one or more flow step in the second region flow order; and determining distance information indicative of a length of the second region using the measured signal or signals. Optionally, each of the one or more flow steps in the second region flow order can include the simultaneous use of two or more different nucleotide bases. In another option, at least one of the one or more flow steps (or each of the one or more flow steps) in the second region flow order includes the simultaneous use of three or more different nucleotide bases. In another option, east one of the one or more flow steps (or each of the one or more flow steps) in the second region flow order comprise the simultaneous use of four different nucleotide bases. The labeled nucleotides can include a label, which is optionally cleaved after measuring the signal after each flow step.

For any of the above methods, labeled nucleotides can be provided in the first region flow order at a concentration less than a concentration of labeled nucleotides provided in the second region flow order.

For any of the above methods, the primer may be extended through the first region before being extended through the second region. Alternatively, the primer may be extended through the second region prior to being extended through the first region.

The distance information determined by any of the above methods may be corrected for primers within a cluster comprising a plurality of copies of the polynucleotide that failed to extend with other primers within the cluster. Alternatively or additionally, the distance information determined by any of the above methods may be determined by determining a normalized signal per base incorporated into the primer, and determining a number of bases incorporated into the primer using the measured signal and the normalized signal per base.

The distance information indicative of the length of the second region for any of the above methods may be determined using a machine learning model.

The method of any of the above may include characterizing the polynucleotide as a duplicate of another polynucleotide or a unique polynucleotide using the distance information.

The method of any of the above may further include generating sequencing data associated with a sequence of a third region of the polynucleotide by extending the primer through a third region using labeled nucleotides according to a third region flow order comprising a plurality of flow steps, and detecting the presence or absence of an incorporated labeled nucleotide after each flow step, wherein the second region is between the first region and the third region, thereby generating a coupled sequencing read pair. Sequencing data of the first region can be associated with the sequencing data of the third region. Expected sequencing data for the second region can be determined using a reference sequence and the second region flow order. The method can further include determining expected sequencing data for the third region using a reference sequence for the second region, the second region flow order, a reference sequence for the third region, and the third region flow order. The method can optionally further include determining expected test variant sequencing data for the second region using the second region flow order and a second reference sequence for the second region, wherein the second reference sequence comprises the test variant. Expected test variant sequencing data for the third region can be determined, for example, using the second reference sequence for the second region, the second region flow order, a reference sequence for the third region, and the third region flow order.

A coupled sequencing read pair can be mapped to a reference sequence by a method that includes mapping a first region or portion thereof, or a third region or portion thereof, of a coupled sequencing read pair generated according to the method described above to a reference sequence; and mapping the unmapped first region or portion thereof, or the unmapped third region or portion thereof, to the reference sequence using the determined distance information.

Another method of mapping a coupled sequencing read pair to a reference sequence can include: mapping a first region or portion thereof and a third region or portion thereof of a coupled sequencing read pair generated according to the method described above to a reference sequence at two or more different position pairs comprising a first position and a second position; and selecting a correct position pair using the determined distance information.

A structural variant (e.g., a chromosomal fusion, an inversion, an insertion, or a deletion) can be detected by a method that includes mapping a first region or portion thereof, or a third region or portion thereof, of a coupled sequencing read pair generated according to the method described above, to a reference sequence; determining an expected locus within a reference sequence for the unmapped first region or portion thereof, or the unmapped third region or portion thereof, using the determined distance information; determining expected sequencing data for a sequence at the expected locus based on the reference sequence; and detecting the structural variant by comparing the sequencing data of the unmapped first region or portion thereof, or the unmapped third region or portion thereof, to the expected sequencing data, wherein a difference between the sequencing data of the unmapped first region or portion thereof, or the unmapped third region or portion thereof, and the expected sequencing data indicates the structural variant.

In another method of detecting a structural variant (e.g., a chromosomal fusion, an inversion, an insertion, or a deletion), the method can include: mapping a first region or portion thereof and a third region or portion thereof, of a coupled sequencing read pair generated according to the method described above, to a reference sequence; determining a mapped distance information between the mapped first region and the mapped third region; and detecting the structural variant by comparing the mapped distance information to the determined distance information of the second region, wherein a difference between the mapped distance information and the determined distance information indicates the structural variant.

BRIEF DESCRIPTION OF THE DRAWINGS

FIG. 14A shows sequencing data obtained by extending a primer with a sequence of 5'-TATGGTCGTCGA-3' (SEQ ID NO: 15) using a repeated flow-cycle order of T-A-C-G. The sequencing data is representative of the extended primer strand, and sequencing information for the complementary template strand can be readily determined is effectively equivalent. FIG. 14B shows the sequencing data shown in FIG. 14A with the most likely sequence, given the sequencing data, selected based on the highest likelihood at each flow position (as indicated by stars). FIG. 14C shows the sequencing data shown in FIG. 14A with traces representing two different candidate sequences (each represented by their complement): TATGGTCATCGA (SEQ ID NO: 16) (closed circles) and TATGGTCGTCGA (SEQ ID NO: 15) (open circles). The likelihood that the sequencing data matches a given sequence can be determined as the product of the likelihood that each flow position matches the candidate sequence.

FIG. 15A shows an alignment of sequencing reads R1 (SEQ ID NO: 15), R2 (SEQ ID NO: 17), and R3 (SEQ ID NO: 18) (each represented by the sequence of an extended primer) aligned with two candidate sequences H1 (SEQ ID NO: 19) and H2 (SEQ ID NO: 20) (each represented by their complement). FIG. 15B shows sequencing data corresponding to R1 with traces representing H1 (closed circles) an H2 (open circles). FIG. 15C shows sequencing data corresponding to R2 with traces representing H1 (closed circles) an H2 (open circles). FIG. 15D shows sequencing data corresponding to R3 with traces representing H1 (closed circles) an H2 (open circles).

FIG. 16 shows sequencing data from a hypothetical nucleic acid molecule sequenced using a A-T-G-C flow cycle order. Traces can be generated using potential haplotype sequences (each represented by their complement) TATGGTCG-TCGA (SEQ ID NO: 21) (H1) and TATGGTCGATCG (SEQ ID NO: 22) (H2), with H1 having a 1 base deletion relative to H2. The sequencing data has a better match to the H2 candidate sequence, and no indel is called in this sequence.

DETAILED DESCRIPTION OF THE INVENTION

Figure 1:
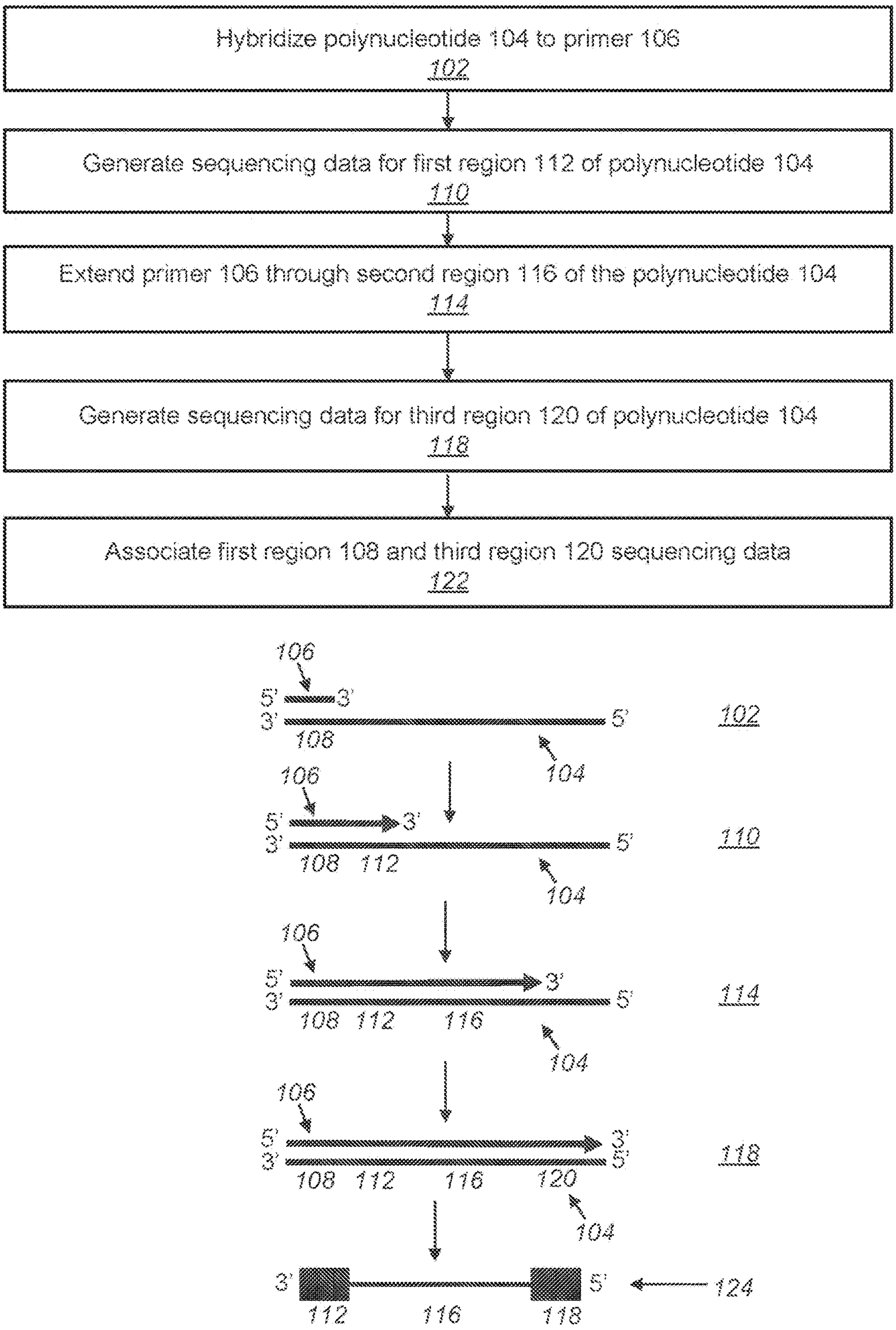
FIG. 1 illustrates a schematic of an exemplary method for generating a coupled sequencing read pair from a polynucleotide.

Described herein are methods of sequencing a polynucleotide. The method can include generating sequencing data associated with the sequenced of a region of a polynucleotide. The sequencing data can be generated by extending a primer through the region using labeled nucleotides provided according to a flow order for that region. The flow order includes a plurality of flow steps, and the presence or absence of an incorporated labeled nucleotide can be detected after each flow step. By including a single base type per sequencing flow and imaging after each flow, high quality sequencing data can be generated for accurate base calling. However, this process can be slow, particularly for long sequencing reads.

The polynucleotide can be hybridized to a sequencing primer, which is extended through a first region (i.e., the 3' end) of the polynucleotide to sequence the first region to generate sequencing data. The primer is then extended through a second region of the polynucleotide, which may occur at a faster rate than the extension of the primer through the first region. The accelerated primer extension through the second region may be referred to as "fast forward sequencing." See International patent application PCT/US2020/031163, the contents of which is incorporated herein by reference for all purposes. As further discussed herein, because the primer is extended through the second region (rather than the second region being completely skipped by the primer, as what occurs in more traditional paired-end sequencing), distance information indicative of the length of the second region may be determined even though the second region is not sequenced in the same manner as the first region.

As further described herein, distance information indicative of the length of the second can be determined by including labeled nucleotides in the flow, and measuring a signal from the labeled nucleotides incorporated into the primer. The flow may include two or more (e.g., 3 or even 4) different types of nucleobases, which increases the average primer extension length per flow. The signal may be taken after every flow, or even less frequently. The measured signal correlates with the number of incorporated labeled nucleotides, and thus the length of the flow or flows.

In one example, a method of sequencing a polynucleotides includes: hybridizing the polynucleotide to a primer to form a hybridized template; generating sequencing data associated with a sequence of a first region of the polynucleotide by extending the primer through the first region of the polynucleotide using labeled nucleotides provided according to a first region flow order comprising a plurality of flow steps, and detecting the presence or absence of an incorporated labeled nucleotide after each flow step; extending the primer through a second region of the polynucleotide using labeled nucleotides provided according to a second region flow order comprising two or more flow steps; measuring a signal from the labeled nucleotides incorporated into the primer after the two or more flow steps of the second region flow order; and determining distance information indicative of the length of the second region using the measured signal.

In another example, a method of sequencing a polynucleotide includes: hybridizing the polynucleotide to a primer to form a hybridized template; generating sequencing data associated with a sequence of a first region of the polynucleotide by extending the primer through the first region of the polynucleotide using labeled nucleotides provided according to a first region flow order comprising a plurality of flow steps, and detecting the presence or absence of an incorporated labeled nucleotide after each flow step; extending the primer through a second region of the polynucleotide using labeled nucleotides provided according to a second region flow order comprising a one or more flow steps, wherein at least one of the one or more flow steps comprises the simultaneous use of two or more different nucleotide bases; measuring a signal from labeled nucleotides incorporated into the primer after each of the one or more flow step in the second region flow order; and determining distance information indicative of a length of the region using the measured signal or signals.

Once the sequencing primer is extended through the second region, the primer can be extended into the third region (i.e., the 5' end) of the polynucleotide to sequence the third region. The sequencing data of the region and the third region can be coupled, resulting in a coupled sequencing read pair for the polynucleotide, and, as further described herein, additional sequencing data can be derived from the second region.

Sequencing data from the first region and the second region may be mapped to a reference sequence. The distance information determined for the region between the first region and the second region can be used to confirm the correct mapping placement of the first region and the second region.

Distance information may be used to determine the length of the polynucleotide. This information can be informative for one of several downstream analyses. For example, the length of the polynucleotide can be used to distinguish a duplication of a polynucleotide from a unique polynucleotide that starts at the same position. It is unlikely that two unique polynucleotides will have the same sequence associated with first region of the polynucleotide and the same length. By knowing the length of the polynucleotide it is possible to characterize the polynucleotide as a unique polynucleotide or a duplicate.

A reference sequence can also be used to extract sequencing data for the second region even though the second region may not have been sequenced directly. For example, sequencing data may be obtained from the first region and/or the third region of the polynucleotide by detecting the presence or absence of a labeled nucleotide incorporated into the extending primer. The reference sequence can be used to determine expected sequencing data (for example, an expected flowgram), which is compared to the generated sequencing data (such as a detected flowgram) to detect variants, including variants within the second region. The comparison between the expected sequencing information (e.g., the expected flowgram) and the generated sequencing data (e.g., the generated flowgram) can be performed in the third region (to detect variants in the second region). This methodology provide significant advantage over traditional paired-end sequencing methods, for which sequencing data for the 3' end or the 5' end of the polynucleotide are not affected by variants in the polynucleotide between the 3' end and the 5' end of the polynucleotide.

Definitions

As used herein, the singular forms “a,” “an,” and “the” include the plural reference unless the context clearly dictates otherwise.

Reference to “about” a value or parameter herein includes (and describes) variations that are directed to that value or parameter per se. For example, description referring to “about X” includes description of “X”.

“Expected sequencing data” refers to sequencing data one would expect if the sequence of a polynucleotide used to generate a coupled sequencing read pair, or the sequence of a region of said polynucleotide, matches a reference sequence.

A “flow order” refers to the order of separate nucleotide flows used to sequence a nucleic acid molecule using non-terminating nucleotides. The flow order may be divided into cycles of repeating units, and the flow order of the repeating units is termed a “flow-cycle order.” A “flow position” refers to the sequential position of a given separate nucleotide flow during the sequencing process.

The terms “individual,” “patient,” and “subject” are used synonymously, and refers to an animal including a human.

The term “label,” as used herein, refers to a detectable moiety that is coupled to or may be coupled to another moiety, for example, a nucleotide or nucleotide analog. The label can emit a signal or alter a signal delivered to the label so that the presence or absence of the label can be detected. In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl) phosphine (TCEP)) or enzymatically cleavable (e.g., via an esterase, lipase, peptidase, or protease). In some embodiments, the label is a fluorophore.

The term “nucleotide,” as used herein, generally refers to any nucleotide or nucleotide analog. The nucleotide may be naturally occurring (e.g., the canonical nucleotide bases A, G, T, U, C) or non-naturally occurring. The nucleotide analog may be a modified, synthesized or engineered nucleotide. The nucleotide analog may not be naturally occurring or may include a non-canonical base. The naturally occurring nucleotide may include a canonical base. The nucleotide analog may include a modified polyphosphate chain (e.g., triphosphate coupled to a fluorophore). The nucleotide analog may comprise a label. The nucleotide analog may be terminated (e.g., reversibly terminated). The nucleotide analog may comprise an alternative base. Non-standard nucleotides, nucleotide analogs, and/or modified analogs may include, but are not limited to, diaminopurine, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl) uracil, (acp3)w, 2,6-diaminopurine, ethynyl nucleotide bases, 1-propynyl nucleotide bases, azido nucleotide bases, phosphoroselenoate nucleic acids and the like. In some cases, nucleotides may include modifications in their phosphate moieties, including modifications to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates) or modifications with selenium moieties (e.g., phosphoroselenoate nucleic acids). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Nucleotide analogs may be capable of reacting or bonding with detectable moieties for nucleotide detection.

A "non-terminating nucleotide" is a nucleic acid moiety that can be attached to a 3' end of a polynucleotide using a polymerase or transcriptase, and that can have another non-terminating nucleic acid attached to it using a polymerase or transcriptase without the need to remove a protecting group or reversible terminator from the nucleotide. Naturally occurring nucleic acids are a type of non-terminating nucleic acid. Non-terminating nucleic acids may be labeled or unlabeled.

The term "% sequence identity" may be used interchangeably herein with the term "% identity" and may refer to the level of nucleotide sequence identity between two or more nucleotide sequences, when aligned using a sequence alignment program. As used herein, 80% identity may be the same thing as 80% sequence identity determined by a defined algorithm and means that a given sequence is at least 80% identical to another length of another sequence. The % identity may be selected from, e.g., at least 60%, at least 65%, at least 70%, at least 75%, at least 80%, at least 85%, at least 90%, at least 95%, or at least 99% or more sequence identity to a given sequence. The % identity may be in the range of, e.g., about 60% to about 70%, about 70% to about 80%, about 80% to about 85%, about 85% to about 90%, about 90% to about 95%, or about 95% to about 99%.

A "short genetic variant" is used herein to describe a genetic polymorph (i.e., mutation) 10 consecutive bases in length or less (i.e., 10, 9, 8, 7, 6, 5, 4, 3, 2, or 1 base(s) in length). The term includes single nucleotide polymorphisms (SNPs), multi-nucleotide polymorphisms (MNPs), and indels 10 consecutive bases in length or less.

It is understood that aspects and variations of the invention described herein include "consisting of" and/or "consisting essentially of" aspects and variations.

When a range of values is provided, it is to be understood that each intervening value between the upper and lower limit of that range, and any other stated or intervening value in that states range, is encompassed within the scope of the present disclosure. Where the stated range includes upper or lower limits, ranges excluding either of those included limits are also included in the present disclosure.

Some of the analytical methods described herein include mapping sequences to a reference sequence, determining sequence information, and/or analyzing sequence information. It is well understood in the art that complementary sequences can be readily determined and/or analyzed, and that the description provided herein encompasses analytical methods performed in reference to a complementary sequence.

The section headings used herein are for organization purposes only and are not to be construed as limiting the subject matter described. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

The figures illustrate processes according to various embodiments. In the exemplary processes, some blocks are, optionally, combined, the order of some blocks is, optionally, changed, and some blocks are, optionally, omitted. In some examples, additional steps may be performed in combination with the exemplary processes. Accordingly, the operations as illustrated (and described in greater detail below) are exemplary by nature and, as such, should not be viewed as limiting.

The disclosures of all publications, patents, and patent applications referred to herein are each hereby incorporated by reference in their entireties. To the extent that any reference incorporated by reference conflicts with the instant disclosure, the instant disclosure shall control.

Flow Sequencing

Sequencing data can be generated using a flow sequencing method that includes extending a primer hybridized to a template polynucleotide molecule according to a pre-determined flow cycle where, in any given flow position, a single type of nucleotide is accessible to the extending primer. At least some of the nucleotides of the particular type include a label, which upon incorporation of the labeled nucleotides into the extending primer renders a detectable signal. The resulting sequence by which such nucleotides are incorporated into the extended primer should be the reverse complement of the sequence of the template polynucleotide molecule. The sequencing data can be generated using a flow sequencing method that includes extending a primer using labeled nucleotides, and detecting the presence or absence of a labeled nucleotide incorporated into the extending primer. Flow sequencing methods may also be referred to as "natural sequencing-by-synthesis," or "non-terminated sequencing-by-synthesis" methods. Exemplary methods are described in U.S. Pat. No. 8,772,473 and International Patent Application No. PCT/2020/031163, each of which is incorporated herein by reference in its entirety. While the following description is provided in reference to flow sequencing methods, it is understood that other sequencing methods may be used to sequence all or a portion of the sequenced region.

Flow sequencing includes the use of nucleotides to extend the primer hybridized to the polynucleotide. Nucleotides of a given base type (e.g., A, C, G, T, U, etc.) can be mixed with hybridized templates to extend the primer if a complementary base is present in the template strand. The nucleotides may be, for example, non-terminating nucleotides. When the nucleotides are non-terminating, more than one consecutive base can be incorporated into the extending primer strand if more than one consecutive complementary base is present in the template strand. The non-terminating nucleotides contrast with nucleotides having 3' reversible terminators, wherein a blocking group is generally removed before a successive nucleotide is attached. If no complementary base is present in the template strand, primer extension ceases until a nucleotide that is complementary to the next base in the template strand is introduced. At least a portion of the nucleotides can be labeled so that incorporation can be detected. Most commonly, only a single nucleotide type is introduced at a time (i.e., discretely added), although two or three different types of nucleotides may be simultaneously introduced in certain embodiments. This methodology can be contrasted with sequencing methods that use a reversible terminator, wherein primer extension is stopped after extension of every single base before the terminator is reversed to allow incorporation of the next succeeding base.

The nucleotides can be introduced at a determined order during the course of primer extension, which may be further divided into cycles. Nucleotides are added stepwise (i.e., in "flow steps"), which allows incorporation of the added nucleotide to the end of the sequencing primer of a complementary base in the template strand is present. During a flow step, a primer hybridized to the polynucleotide is extended using one or more nucleotides. A flow step may include a single base type or the simultaneous use (e.g., a mixture) of two or more different base types. The cycles may have the same order of nucleotides and number of different base types or a different order of nucleotides and/or a different number of different base types. Solely by way of example, the order of a flow cycle may be A-T-G-C, wherein A nucleobases are used in a first flow, T nucleobases are used in a second flow, G nucleobases are used in a third flow, and C nucleobases are used in a fourth flow, before the cycle is restarted beginning with A nucleobases in the first flow. Alternative orders may be readily contemplated by one skilled in the art. Between the introductions of different nucleotides, unincorporated nucleotides may be removed, for example by washing the sequencing platform with a wash fluid. For example, during sequencing, one or more labeled nucleotides can be incorporated into the extending primer, the hybridized template is washed, and a detector is used to detect a signal from the label of the nucleotide, which indicates whether the nucleotide has been incorporated into the extended primer. The label on the incorporated nucleotides may be cleaved after imaging and prior to proceeding to the next flow step of the flow cycle.

[A polymerase can be used to extend a sequencing primer by incorporating one or more nucleotides at the end of the primer in a template-dependent manner. In some embodiments, the polymerase is a DNA polymerase. The polymerase may be a naturally occurring polymerase or a synthetic (e.g., mutant) polymerase. The polymerase can be added at an initial step of primer extension, although supplemental polymerase may optionally be added during sequencing, for example with the stepwise addition of nucleotides or after a number of flow cycles. Exemplary polymerases include a DNA polymerase, an RNA polymerase, a thermostable polymerase, a wild-type polymerase, a modified polymerase, Bst DNA polymerase, Bst 2.0 DNA polymerase Bst 3.0 DNA polymerase, Bsu DNA polymerase, *E. coli* DNA polymerase I, T7 DNA polymerase, bacteriophage T4 DNA polymerase 129 (phi29) DNA polymerase, Taq polymerase, Tth polymerase, Tli polymerase, Pfu polymerase, and SeqAmp DNA polymerase.

The introduced nucleotides can include labeled nucleotides when determining the sequence of the template strand, and the presence or absence of an incorporated labeled nucleic acid can be detected to determine a sequence. The label may be, for example, an optically active label (e.g., a fluorescent label) or a radioactive label, and a signal emitted by or altered by the label can be detected using a detector. The presence or absence of a labeled nucleotide incorporated into a primer hybridized to a template polynucleotide can be detected, which allows for the determination of the sequence (for example, by generating a flowgram). In some embodiments, the labeled nucleotides are labeled with a fluorescent, luminescent, or other light-emitting moiety. In some embodiments, the label is attached to the nucleotide via a linker. In some embodiments, the linker is cleavable, e.g., through a photochemical or chemical cleavage reaction. For example, the label may be cleaved after detection and before incorporation of the successive nucleotide(s). In some embodiments, the label (or linker) is attached to the nucleotide base, or to another site on the nucleotide that does not interfere with elongation of the nascent strand of DNA. In some embodiments, the linker comprises a disulfide or PEG-containing moiety.

A given sequencing flow step can include providing labeled nucleotides to the polynucleotide, there by extending the sequencing primer. Incorporated nucleotides can be detected (e.g., by imaging) to generate the sequencing data. The label on the nucleotide may be cleaved before proceeding to the next sequencing flow step. Optionally, an additional amount of nucleotides having the same nucleobase (the nucleotides being either labeled or unlabeled, or a mixture) may be added prior to proceeding to the next sequencing flow step. This additional amount of nucleotides can reduce lagging sequencing primers.

Nucleotides used during a sequencing flow may include only labeled nucleotides or a mixture of labeled and unlabeled nucleotides. For example, the portion of labeled nucleotides compared to total nucleotides may be about 90% or less, about 80% or less, about 70% or less, about 60% or less, about 50% or less, about 40% or less, about 30% or less, about 20% or less, about 10% or less, about 5% or less, about 4% or less, about 3% or less, about 2.5% or less, about 2% or less, about 1.5% or less, about 1% or less, about 0.5% or less, about 0.25% or less, about 0.1% or less, about 0.05% or less, about 0.025% or less, or about 0.01% or less. In some embodiments, the portion of labeled nucleotides compared to total nucleotides is about 100%, about 95% or more, about 90% or more, about 80% or more about 70% or more, about 60% or more, about 50% or more, about 40% or more, about 30% or more, about 20% or more, about 10% or more, about 5% or more, about 4% or more, about 3% or more, about 2.5% or more, about 2% or more, about 1.5% or more, about 1% or more, about 0.5% or more, about 0.25% or more, about 0.1% or more, about 0.05% or more, about 0.025% or more, or about 0.01% or more. In some embodiments, the portion of labeled nucleotides compared to total nucleotides is about 0.01% to about 100%, such as about 0.01% to about 0.025%, about 0.025% to about 0.05%, about 0.05% to about 0.1%, about 0.1% to about 0.25%, about 0.25% to about 0.5%, about 0.5% to about 1%, about 1% to about 1.5%, about 1.5% to about 2%, about 2% to about 2.5%, about 2.5% to about 3%, about 3% to about 4%, about 4% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to less than 100%, or about 90% to about 100%.

Sequencing data, such as a flowgram, can be generated based on the detection of an incorporated nucleotide and the order of nucleotide introduction. Take, for example, the flowing template sequences: CTG and CAG, and a repeating flow cycle of T-A-C-G (that is, sequential addition of T, A, C, and G nucleotides, which would be incorporated into the primer only if a complementary base is present in the template polynucleotide). A resulting flowgram is shown in Table 1, where 1 indicates incorporation of an introduced nucleotide and 0 indicates no incorporation of an introduced nucleotide. The flowgram can be used to determine the sequence of the template strand.

TABLE 1

| | Cycle 1 | | | | Cycle 2 | | | |
|---|---|---|---|---|---|---|---|---|
| Sequence | T | A | C | G | T | A | C | G |
| CTG | 0 | 0 | 0 | 1 | 0 | 1 | 1 | 0 |
| CAG | 0 | 0 | 0 | 1 | 1 | 0 | 1 | 0 |
| CCG | 0 | 0 | 0 | 2 | 0 | 0 | 1 | 0 |

The flowgram may be binary or non-binary. A binary flowgram detects the presence (1) or absence (0) of an incorporated nucleotide. A non-binary flowgram can more quantitatively determine a number of incorporated nucleotide from each stepwise introduction. For example, a sequence of CCG would incorporate two G bases, and any signal emitted by the labeled base would have a greater intensity as the incorporation of a single base. This is shown in Table 1. The non-binary flowgram also indicates the presence or absence of the base, but can provide additional information including the number of bases incorporated at the given step.

The number of sequencing flows or flow cycles can be increased or decreased to obtain the desired sequencing region length. Extension of the primer in the sequencing region can include one or more sequencing flows for stepwise extension of the primer using nucleotides having one or more different base types. For example, extension of the primer through any of the sequencing regions may include between 1 and about 1000 sequencing flow steps, such as between 1 and about 10 sequencing flow steps, between about 10 and about 20 sequencing flow steps, between about 20 and about 50 sequencing flow steps, between about 50 and about 100 sequencing flow steps, between about 100 and about 250 sequencing flow steps, between about 250 and about 500 sequencing flow steps, or between about 500 and about 1000 sequencing flow steps. The sequencing flow steps may be segmented into identical or different flow cycles. The number of bases incorporated into the primer in the sequencing region depends on the sequence of the sequencing region, and the flow cycle used to extend the primer in the sequencing region. For example, the sequencing region can be about 1 base to about 4000 bases in length, such as about 1 base to about 10 bases in length, about 10 bases to about 20 bases in length, about 20 bases to about 50 bases in length, about 50 bases to about 100 bases in length, about 100 bases to about 250 bases in length, about 250 bases to about 500 bases in length, about 500 bases to about 1000 bases in length, about 1000 bases to about 2000 bases in length, or about 2000 bases to about 4000 bases in length, or more, depending on the number of sequencing flows used in the sequencing region.

Prior to generating the sequencing data, the polynucleotide is hybridized to a sequencing primer to generate a hybridized template. The polynucleotide may be ligated to an adapter during sequencing library preparation. The adapter can include a hybridization sequence that hybridizes to the sequencing primer. For example, the hybridization sequence of the adapter may be a uniform sequence across a plurality of different polynucleotides, and the sequencing primer may be a uniform sequencing primer. This allows for multiplexed sequencing of different polynucleotides in a sequencing library.

The polynucleotide may be attached to a surface (such as a solid support) for sequencing. The polynucleotides may be amplified (for example, by bridge amplification or other amplification techniques) to generate polynucleotide sequencing clusters. The amplified polynucleotides within the cluster are substantially identical or complementary (some errors may be introduced during the amplification process such that a portion of the polynucleotides may not necessarily be identical to the original polynucleotide). Cluster formation allows for signal amplification so that the detector can accurately detect incorporation of labeled nucleotides for each colony. In some cases, the cluster is formed on a bead using emulsion PCR and the beads are distributed over a sequencing surface.

Examples for systems and methods for sequencing can be found in U.S. Pat. No. 10,344,328, published International application WO 2019/099886, and published International application WO 2020/186243, each of which is incorporated herein by reference in its entirety. In brief, an exemplary system can include a rotatable substrate that polynucleotides can be affixed to for sequencing. Polynucleotides from a sample can be attached to a support, such as a bead, and amplified on to the support to generate a plurality of polynucleotide copied (i.e., a sequencing cluster) on the support. The support, including the sequencing cluster, can then be attached to the rotatable substrate. In another variation, the polynucleotide for the sample is directly attached to the rotatable substrate and amplified on the substrate to generate the sequencing cluster. Reagents (such as wash buffers, primers, polymerase buffers, nucleotides in a sequencing flow or re-phasing flow, etc.) can be dispensed onto the rotatable substrate, for example proximal to the center of the rotatable substrate. The substrate can rotate, which causes the dispense reagents to flow outwardly, thereby contacting the sequencing cluster (and the polynucleotides within the sequencing cluster) with the reagent.

A given sequencing flow step can include one or more wash steps, one or more nucleotide dispensing steps, one or more sequencing signal detection steps, and one or more label cleavage steps. The amount of reagent and/or rotation speed of the rotatable substrate can vary depending on the desired incubation time. By way of example, a sequencing flow can include an initial wash, wherein a wash buffer is applied to the rotatable substrate rotates to flow the wash buffer across the surface of the rotatable substrate. The wash can be repeated one or more times, using the same or different amount of wash buffer, and the same or a different rotation speed of the rotatable substrate. A buffer containing nucleotides according to the sequencing flow is then dispensed on the rotatable substrate, and the substrate is rotate to flow the nucleotides across the substrate. According to some flow steps, a single nucleotide base type is used in the flow steps. Other flow steps may include the simultaneous use of two or more different types of nucleotide bases. If two or more different types of nucleotide bases are simultaneously used, the different type of nucleotide bases may be pre-mixed (i.e., before being dispensed onto the substrate), or may be dispensed separately onto the substrate and mixed on the substrate. Sequencing primers can be extended upon contact with the nucleotides in accordance with the template provided by the polynucleotide. A wash buffer can then be dispensed and the rotatable substrate rotated to wash away excess nucleotide. This wash step is optionally repeated one or more times using the same amount of wash buffer or a different amount, and by rotating the substrate at the same speed or a different speed. A sequencing signal can then be detected from the labeled nucleotides, for example by imaging the substrate.

The concentration of the nucleotides in different sequencing flows may be the same or different. For example, the concentration of T nucleotides in a T sequencing flow and C nucleotides in a C sequencing flow may be the same or different from the concentration of A nucleotides in an A nucleotide and/or G nucleotides in a G nucleotide flow. Different nucleotides can have different incorporation and/or over-incorporation rates, and the concentration of any given nucleotide may be selected by balancing the under- or over-incorporation of the nucleotide during sequencing (i.e., resulting in an acceptable number of leading or lagging primers). By way of example, the concentration of the nucleotides in the sequencing flow may be between about 0.1 μM and about 100 μM (for example, any one of about 0.1 μM, about 0.5 μM, about 1 μM, about 2 μM, about 3 μM, about 4 μM, about 5 μM, about 6 μM about 7 μM, about 8 μM, about 9 μM, about 10 μM, about 11 μM, about 12 μM, about 13 μM, about 14 μM, or about 15 μM, about 20 μM, about 25 μM, about 30 μM, about 40 μM, about 50 μM, about 60 μM, about 70 μM, about 80 μM, about 90 μM or about 100 μM, or any concentration between any of such concentrations).

After detecting the sequencing signal (e.g., by imaging), a cleavage buffer can then be applied to the substrate, and the substrate rotated to flow the cleavage buffer across the substrate and contact the sequencing clusters. The cleavage buffer contains reagent that cleave the label from the labeled nucleotides. The cleavage buffer can then be washed from the substrate one or more times by dispensing a wash buffer on the substrate and rotating the substrate. Optionally, the sequencing flow may include again dispensing the same nucleotide, which can help minimize lagging strands, which is subsequently washed using a wash buffer. A similar process is then repeated for the next sequencing flow.

The polynucleotide may be, in some embodiments, up to 100 bases (bp), 150 bp, 200 bp, 250 bp, 300 bp, 400 bp, 500 bp, 600 bp, 700 bp, 800 bp, 900 bp or 1,000 bp in length. In some embodiments, the length can be longer than 1,000 bp such as up to 1.1 kilobases (kb), 1.2 kb, 1.3 kb, 1.4 kb, 1.5 kb, 1.6 kb, 1.7 kb, 1.8 kb, 1.9 kb, or 2 kb or longer.

The polynucleotides used in the methods described herein may be obtained from any suitable biological source, for example a tissue sample, a blood sample, a serum sample, a cerebrospinal fluid sample, a plasma sample, a saliva sample, a fecal sample, or a urine sample. The polynucleotides may be DNA or RNA polynucleotides. In some embodiments, RNA polynucleotides are reverse transcribed into DNA polynucleotides prior to hybridizing the polynucleotide to the sequencing primer. In some embodiments, the polynucleotide is a cell-free DNA (cfDNA), such as a circulating tumor DNA (ctDNA) or a fetal cell-free DNA.

Libraries of the polynucleotides may be prepared through known methods. In some embodiments, the polynucleotides may be ligated to an adapter sequence. The adapter sequence may include a hybridization sequence that hybridized to the primer extended during the generated of the coupled sequencing read pair.

In some embodiments, the sequencing data is obtained without amplifying the nucleic acid molecules prior to establishing sequencing colonies (also referred to as sequencing clusters). Methods for generating sequencing colonies include bridge amplification or emulsion PCR. Methods that rely on shotgun sequencing and calling a consensus sequence generally label nucleic acid molecules using unique molecular identifiers (UMIs) and amplify the nucleic acid molecules to generate numerous copies of the same nucleic acid molecules that are independently sequenced. The amplified nucleic acid molecules can then be attached to a surface and bridge amplified to generate sequencing clusters that are independently sequenced. The UMIs can then be used to associate the independently sequenced nucleic acid molecules. However, the amplification process can introduce errors into the nucleic acid molecules, for example due to the limited fidelity of the DNA polymerase. In some embodiments, the nucleic acid molecules are not amplified prior to amplification to generate colonies for obtaining sequencing data. In some embodiments, the nucleic acid sequencing data is obtained without the use of unique molecular identifiers (UMIs).

Fast Forward Regions and Distance Determination in Fast Forward Regions

The primer hybridized to the polynucleotide can be extended through a region of the polynucleotide (e.g., a second region, wherein sequencing data associated with a sequence of the first region is determined, for example as described above) using an accelerated "fast forward" process. That is, extension of the primer through the fast-forward region may proceed faster that the extension of the primer through a sequenced region. During flow sequencing, as discussed above, a labeled nucleotide is incorporated into the extending primer, the hybridized template is washed, and a detector is used to detect a signal from the label of the nucleotide, which indicates whether the nucleotide has been incorporated into the extended primer. However, the detection process takes time, and extension of the primer through the second region can be accelerated.

By including labeled nucleotides in flows used to extend the primer through the fastforward region, it is possible to detect a signal from the labeled nucleotides into the primer and determine distance information indicative of the length of the fast-forward region using the measured signal. The number of labeled nucleotides in the sequencing primer is correlated with the length of the fast forward region. The proportion of nucleotides that are labeled (compared to unlabeled nucleotides) used when extending the primer in the fastforward region may be less than the proportion of nucleotides that are labeled when generating the sequencing data. This helps prevent signal oversaturation of the detector.

Distance information refers to an approximate number of bases in the second region. The distance information is indicative of the length of the second region, although need not be the precise length of the second region because the unmapped region is ultimately mapped within a location approximated by the distance information.

Extension of the primer through the fast-forward region may be accelerated, for example, by reducing the imaging frequency. When generating sequencing data, the presence or absence of labeled nucleotides incorporated into the sequencing primer is generally detected after each sequencing flow step. This may be followed by a cleavage step (wherein the label is cleaved from the nucleotides) before proceeding with the subsequent flow step. If, instead of imaging and cleaving after each flow step, the imaging and cleaving frequency is reduced, the sequencing primer is extended at a faster rate.

Extension of the primer through the fast forward region may also or alternatively be accelerated by using a mixture of at least two different types of nucleotides in at least one step of the flow order used during extension of the primer through the second region. For example, two different bases, such as G and C, may be used simultaneously in the same step, which extends the primer if a complementary C or G base are present. This accelerates extension of the primer by incorporating consecutive bases into the primer even if those bases are of different base types. In some embodiments, at least one flow step includes the simultaneous use of 2 different bases. In some embodiments, at least one flow step includes the simultaneous use of 3 different base. In some embodiments, at least one flow step includes the simultaneous use of 4 different baes. The incubation time of the flow step may be controlled, for example when simultaneously using 4 different bases, to control the length of the fast-forward region.

Exemplary flow steps that include the simultaneous use of 2 different bases include simultaneous use of A and C nucleotides, A and G nucleotides, A and T nucleotides, C and G nucleotides, C and T nucleotides, and G and T nucleotides. Exemplary flow steps that include the simultaneous use of 3 different bases include simultaneous use of A, C, and G nucleotides; A, C, and T nucleotides; A, G, and T nucleotides; and C, G, and T nucleotides. Exemplary flow steps that include the simultaneous use of 3 different bases include simultaneous use of A, C, G, and T nucleotides.

By way of example, consider a sequence of SEQ ID NO: 1 and the corresponding flow order and flowgram shown in Table 2. The flow order process for extending the sequencing primer hybridized to a polynucleotide containing SEQ ID NO: 1 includes 5 cycles, with Cycles 1, 4, and 5 being the same as each other and Cycles 2 and 3 being the same as each other (with Cycles 1, 4, and 5 being different from Cycles 2 and 3). In this example, each cycle has 4 steps, with Cycles 1, 4, and 5 include the sequential and independent addition of A-C-T-G nucleotides, with a single base type being added at each cycle step. Cycles 2 and 3 include four cycle steps, wherein Step 1 omits A nucleotides (i.e., includes C, T, and G), Step 2 omits, C nucleotides (i.e., includes A, T, and G), Step 3 omits T nucleotides (i.e., includes A, C, and G), and Step 4 omits G nucleotides (i.e., includes A, C, and T). Because Cycles 2 and 3 include multiple different nucleotide base types simultaneously during primer extension, the primer is extended faster than if only a single base type was used at any given step. The flowgram shown in Table 2 for extending the primer against the SEQ ID NO: 1 template using this flow order results in up to 6 bases being added (Cycle 3, Step 3) during the fast forward portion of primer extension. In contrast, Table 3 shows a flowgram of the same SEQ ID NO: 1 using the A-C-T-G cycles with single nucleotides used at each step (similar to Cycles 1, 4, and 5 in Table 2). The flow order used to extend the primer shown in Table 3 requires 10 four-step cycles to extend the primer through the polynucleotide, which is substantially slower than the 5 four-step cycles used to extend the primer through the polynucleotide using the flow order provided in Table 2.

TABLE 2

| | Cycle | | | | | | | | | | | | | | | | | | | |
|---|---|---|---|---|---|---|---|---|---|---|---|---|---|---|---|---|---|---|---|---|
| | 1 | | | | 2 | | | | 3 | | | | 4 | | | | 5 | | | |
| Cycle Step | 1 | 2 | 3 | 4 | 1 | 2 | 3 | 4 | 1 | 2 | 3 | 4 | 1 | 2 | 3 | 4 | 1 | 2 | 3 | 4 |
| Flow Bases | A | C | T | G | C/T/G | A/T/G | A/C/G | A/C/T | C/T/G | A/T/G | A/C/G | A/C/T | A | C | T | G | A | C | T | G |
| Number of Bases Incorporated | 1 | 1 | 1 | 1 | 0 | 2 | 1 | 3 | 4 | 3 | 6 | 2 | 0 | 0 | 0 | 1 | 1 | 1 | 1 | 1 |
| Base(s) Incorporated | A | C | T | G | — | AA | C | TTA | GGCT (SEQ ID NO: 2) | ATA | CGGACG (SEQ ID NO: 3) | TC | — | — | — | G | A | C | T | G |

Flowgram for SEQ ID NO: 1: 3'-TGACTTGAATCCGATATGCCTGCAGCTGAC-5'

TABLE 3

| | Cycle | | | | | | | | | | | | | | | | | | | |
|---|---|---|---|---|---|---|---|---|---|---|---|---|---|---|---|---|---|---|---|---|
| | 1 | | | | 2 | | | | 3 | | | | 4 | | | | 5 | | | |
| Cycle Step | 1 | 2 | 3 | 4 | 1 | 2 | 3 | 4 | 1 | 2 | 3 | 4 | 1 | 2 | 3 | 4 | 1 | 2 | 3 | 4 |
| Flow Bases | A | C | T | G | A | C | T | G | A | C | T | G | A | C | T | G | A | C | T | G |
| Number of Bases Incorporated | 1 | 1 | 1 | 1 | 2 | 1 | 2 | 0 | 1 | 0 | 0 | 2 | 0 | 1 | 1 | 0 | 1 | 0 | 1 | 0 |
| Base(s) Incorporated | A | C | T | G | AA | C | TT | – | A | – | – | CC | – | C | T | – | A | – | T | – |

| | Cycle | | | | | | | | | | | | | | | | | | | |
|---|---|---|---|---|---|---|---|---|---|---|---|---|---|---|---|---|---|---|---|---|
| | 6 | | | | 7 | | | | 8 | | | | 9 | | | | 10 | | | |
| Cycle Step | 1 | 2 | 3 | 4 | 1 | 2 | 3 | 4 | 1 | 2 | 3 | 4 | 1 | 2 | 3 | 4 | 1 | 2 | 3 | 4 |
| Flow Bases | A | C | T | G | A | C | T | G | A | C | T | G | A | C | T | G | A | C | T | G |
| Number of Bases Incorporated | 1 | 1 | 0 | 2 | 1 | 1 | 0 | 1 | 0 | 0 | 1 | 0 | 0 | 1 | 0 | 1 | 1 | 1 | 1 | 1 |
| Base(s) Incorporated | A | C | – | GG | A | C | – | G | – | – | T | – | – | C | – | G | A | C | T | G |

Flowgram for SEQ ID NO: 1: 3'-TGACTTGAATCCGATATGCCTGCAGCTGAC-5'

The fast forward method is particularly useful for accelerating primer extension through a region that is not directly sequenced. For example, in reference to Table 2, Cycles 1, 4, and 5 used labeled nucleotides in a stepwise manner to generate sequencing data associated with the first region (Cycle 1) and the third region (Cycles 4 and 5), while the primer was quickly extended through the second region (Cycles 2 and 3) between the first and third region.

Primer extension using flow sequencing allows for long-range sequencing on the order of hundreds or even thousands of bases in length. The number of flow steps or cycles can be increased or decreased to obtain the desired sequencing length. Extension of the primer in the first region or the third region can include one or more flow steps for stepwise extension of the primer using nucleotides having one or more different base types. In some embodiments, extension of the primer in the first region or extension of the primer in the third region includes between 1 and about 1000 flow steps, such as between 1 and about 10 flow steps, between about 10 and about 20 flow steps, between about 20 and about 50 flow steps, between about 50 and about 100 flow steps, between about 100 and about 250 flow steps, between about 250 and about 500 flow steps, or between about 500 and about 1000 flow steps. The flow steps may be segmented into identical or different flow cycles. The number of bases incorporated into the primer in the first region or the third region depends on the sequence of the first region or third region, respectively, and the flow order used to extend the primer in the first region or third region. In some embodiments, the first region or third region is about 1 base to about 4000 bases in length, such as about 1 base to about 10 bases in length, about 10 bases to about 20 bases in length, about 20 bases to about 50 bases in length, about 50 bases to about 100 bases in length, about 100 bases to about 250 bases in length, about 250 bases to about 500 bases in length, about 500 bases to about 1000 bases in length, about 1000 bases to about 2000 bases in length, or about 2000 bases to about 4000 bases in length.

Primer extension through the second region may proceed through any number of flow steps. In some embodiments, extension of the primer through the second region omits labeled nucleotides, which further increases the feasible extension distance of the primer without polymerase stall. In some embodiments, extension of the primer through the second region includes between 1 and about 10,000 flow steps, such as between 1 and about 10 flow steps, between about 10 and about 20 flow steps, between about 20 and about 50 flow steps, between about 50 and about 100 flow steps, between about 100 and about 250 flow steps, between about 250 and about 500 flow steps, between about 500 and about 1000 flow steps, between about 1000 flow steps and about 2500 flow steps, between about 2500 flow steps and about 5000 flow steps, or between about 5000 flow steps and about 10,000 flow steps. In some embodiments, extension of the primer through the second region includes more than about 10,000 flow steps. The number of bases incorporated into the primer in the second region depends on the sequence of the second region, and the flow order used to extend the primer in the second region. In some embodiments, the second region is about 1 base to about 50,000 bases in length, such as about 1 base to about 10 bases in length, about 10 bases to about 20 bases in length, about 20 bases to about 50 bases in length, about 50 bases to about 100 bases in length, about 100 bases to about 250 bases in length, about 250 bases to about 500 bases in length, about 500 bases to about 1000 bases in length, about 1000 bases to about 2000 bases in length, about 2000 bases to about 2500 bases in length, about 2500 to about 5000 bases in length, about 5000 to about 10,000 bases in length, about 10,000 to about 25,000 bases in length, or about 25,000 to about 50,000 bases in length. In some embodiments, the length of the second region is more than about 50,000 bases in length.

Extension of the primer can proceed through the first region (e.g., a sequencing region), the second region (e.g., a fast-forward region), and the third region (e.g., a second sequencing region). Signals from labels of nucleotides incorporated into the extending primer through the first and third regions can be detected to generate sequencing data. Extension of the primer through the second region can occur at a faster rate than extension of the primer through the first and/or third regions, for example by decreasing the frequency of signal detection from labeled nucleotides incorporated into the extending primer, or by including a mixture of at least two different types of nucleotide bases to extend the primer.

FIG. 1 illustrates a schematic of an exemplary method for generating a coupled sequencing read pair from a polynucleotide (such as DNA). At 102, the polynucleotide 104 is hybridized with a primer 106 to form a hybridized template. In some embodiments, the polynucleotide includes an adapter region 108, which may be ligated to the 3' of the target polynucleotide during sequencing library preparation. The adapter region 108 can include a hybridization region, and the primer 106 can hybridize to the hybridization region of the adapter region 108. At step 110, sequencing data for the first region 112 of the polynucleotide 104 is generated by extending the primer 106 using labeled nucleotides, and detecting the presence or absence of an incorporated labeled nucleotide. The nucleotides used to extend the primer may further include unlabeled nucleotides, although labeled nucleotides are used to detect nucleotide incorporation for generating the sequencing data. In some embodiments, the nucleotides are added stepwise in one or more cycles according to a first region flow order to extend the primer 106 through the first region 112, and the hybridized template may be washed following a cycle step to remove unincorporated nucleotides prior to detecting the presence or absence of an incorporated labeled nucleotide. At step 114, the primer 106 is extended through a second region 116 of the polynucleotide 104 according to a second region flow order. The primer 106 may be extended through the second region 116 at a rate faster than extension of the primer in step 110. This accelerated primer extension may be referred to as the "fast-forward" portion of the method. Nucleotides (which may be labeled at a lower proportion compared to sequenced regions) are added to the hybridized template stepwise in one or more cycles according to the second region flow order. In some embodiments, more than one (e.g., two, three, or four) different base types are simultaneously used in a given cycle step, which accelerates the primer extension. At step 118, sequencing data for the third region 118 of the polynucleotide 104 is generated by extending the primer 106 using labeled nucleotides, and detecting the presence or absence of an incorporated labeled nucleotide. Generation of the sequencing data for the third region 118 may proceed in a similar manner as described for generating the sequencing data for the first region 112. At step 122, the sequencing data generated for the first region 112 is associate with the sequencing data generated for the third region 120, which results in the coupled sequencing read pair 124 for the polynucleotide 104. The sequencing data associated between the first and third regions may include the sequence of the first and third regions. The coupled sequencing read pair 124 includes sequencing data for the first region 112 and the third region 120, which are separated by the second region 116 for which sequencing data is not necessarily known.

Extension of the primer through the fast-forward region by be accelerated, for example, by reducing the frequency at which the incorporation of labeled nucleotides into the sequencing primer is detected. For example, the primer may be extended through a fast forward region using labeled nucleotides provided according to a fast-forward region flow order comprising two or more flow steps; and measuring a signal from the labeled nucleotides incorporated into the primer after the two or more flow steps. In contrast, detection in a sequencing region may occur after each flow step. Optionally, the labels of the nucleotides may be cleaved after measuring the signal before proceeding to the next flow step. Measuring the signal (and, optionally, cleaving of the label) may proceed every two or more (e.g., every 2, 3, 4, 5, or more) flow steps. From the measured signal or signals, distance information indicative of the length of the fast-forward region can be determined.

By way of example, sequencing a polynucleotide may include hybridizing the polynucleotide to a primer to form a hybridized template, and generating sequencing data associated with a sequence of a first region (i.e., a sequencing region) of the polynucleotide by extending the primer through the first region of the polynucleotide using labeled nucleotides provided according to a first region flow order comprising a plurality of flow steps, and detecting the presence or absence of an incorporated labeled nucleotide after each flow step. The primer my further be extended through a second region (i.e., a fast-forward region) of the polynucleotide using labeled nucleotides (or the simultaneous use of labeled and unlabeled nucleotides) provided according to a second region flow order (i.e., a fastforward flow order) comprising two or more flow steps. Labeled (and, if present, unlabeled) nucleotides may be incorporated into the sequencing primer, thereby extending the sequencing primer. The primer may be extended through the fast-forward region without detecting labeled nucleotides that are incorporated into the extending primer after each flow step in the second region flow order. That is a signal from the labeled nucleotide incorporated into the primer may be measured after the two or more flow steps of the fast-forward region flow order. The label of the nucleotides may be cleaved after measuring the signal. However, as the signal need not be detected after each flow step, the label need not be cleaved after each flow step. For example, signal detection and/or cleavage of the label may occur every 2, every 3, every 4, every 5, or more flow steps. The proportion of labeled nucleotides to total nucleotides (i.e., the sum of labeled and unlabeled nucleotides) used in the two or more flow steps of the fast-forward region flow order may be less than the proportion of labeled nucleotides to total nucleotides provided according to the flow order used to extend the primer in the first region (i.e., the sequencing region). Every flow step the fast-forward flow order can have labeled nucleotides. Alternative, a first portion of the two or more flow steps in the fast-forward flow order may comprise the use of only unlabeled nucleotides (i.e., no labeled nucleotides) and a second portion of the two or more flow steps comprise the use of labeled nucleotides (or the simultaneous use of labeled and unlabeled nucleotides). From the measured signal distance information indicative of the length of the second region can be determined, for example based on the correlation between signal intensity and distance. The signal can be detected multiple times with the fast-forward region, and the set of signals can be used to determine the distance information indicative of the length of the second region.

Extension of the primer through the fast forward region may also or alternatively be accelerated by using a mixture of at least two different types of nucleotides in at least one step of the flow order used during extension of the primer through the second region. For example, two different bases, such as G and C, may be used simultaneously in the same step, which extends the primer if a complementary C or G base are present. This accelerates extension of the primer by incorporating consecutive bases into the primer even if those bases are of different base types. In some embodiments, at least one step of the flow order includes 2 different bases. In some embodiments, at least one step of the flow order includes 3 different baes. In some embodiments, at least one step of the flow order includes 4 different baes. If two or more (e.g., 3 or 4) different bases are simultaneously used in a given flow step, measuring the signal (and, optionally, cleaving the label) may occur after each flow step, or after two or more flow steps.

By way of example, sequencing a polynucleotide may include hybridizing the polynucleotide to a primer to form a hybridized template, and generating sequencing data associated with a sequence of a first region (i.e., a sequencing region) of the polynucleotide by extending the primer through the first region of the polynucleotide using labeled nucleotides provided according to a first region flow order comprising a plurality of flow steps, and detecting the presence or absence of an incorporated labeled nucleotide after each flow step. The primer my further be extended through a second region (i.e., a fast-forward region) of the polynucleotide using labeled nucleotides (or the simultaneous use of labeled and unlabeled nucleotides) provided according to a second region flow order (i.e., a fastforward flow order) comprising two or more flow steps, wherein each flow step comprises the simultaneous use of two or more (e.g., 3 or 4) nucleotides. Labeled (and, if present, unlabeled) nucleotides may be incorporated into the sequencing primer, thereby extending the sequencing primer. The primer may be extended through the fast-forward region without detecting labeled nucleotides that are incorporated into the extending primer after each flow step in the second region flow order. That is a signal from the labeled nucleotide incorporated into the primer may be measured after the two or more flow steps of the fast-forward region flow order. The label of the nucleotides may be cleaved after measuring the signal. However, as the signal need not be detected after each flow step, the label need not be cleaved after each flow step. For example, signal detection and/or cleavage of the label may occur every 2, every 3, every 4, every 5, or more flow steps. The proportion of labeled nucleotides to total nucleotides (i.e., the sum of labeled and unlabeled nucleotides) used in the two or more flow steps of the fast-forward region flow order may be less than the proportion of labeled nucleotides to total nucleotides provided according to the flow order used to extend the primer in the first region (i.e., the sequencing region). Every flow step the fast-forward flow order can have labeled nucleotides. Alternative, a first portion of the two or more flow steps in the fast-forward flow order may comprise the use of only unlabeled nucleotides (i.e., no labeled nucleotides) and a second portion of the two or more flow steps comprise the use of labeled nucleotides (or the simultaneous use of labeled and unlabeled nucleotides). From the measured signal distance information indicative of the length of the second region can be determined, for example based on the correlation between signal intensity and distance. The signal can be detected multiple times with the fast-forward region, and the set of signals can be used to determine the distance information indicative of the length of the second region.

In another example, sequencing a polynucleotide may include hybridizing the polynucleotide to a primer to form a hybridized template, and generating sequencing data associated with a sequence of a first region (i.e., a sequencing region) of the polynucleotide by extending the primer through the first region of the polynucleotide using labeled nucleotides provided according to a first region flow order comprising a plurality of flow steps, and detecting the presence or absence of an incorporated labeled nucleotide after each flow step. The primer my further be extended through a second region (i.e., a fast-forward region) of the polynucleotide using labeled nucleotides (or the simultaneous use of labeled and unlabeled nucleotides) provided according to a second region flow order (i.e., a fastforward flow order) comprising one or more flow steps, wherein each flow step comprises the simultaneous use of two or more (e.g., 3 or 4) nucleotides. Labeled (and, if present, unlabeled) nucleotides may be incorporated into the sequencing primer, thereby extending the sequencing primer. A signal from the labeled nucleotide incorporated into the primer after each of the one or more flow steps in the fast-forward region flow order. The label of the nucleotides may be cleaved after measuring the signal. The proportion of labeled nucleotides to total nucleotides (i.e., the sum of labeled and unlabeled nucleotides) used in the two or more flow steps of the fast-forward region flow order may be less than the proportion of labeled nucleotides to total nucleotides provided according to the flow order used to extend the primer in the first region (i.e., the sequencing region). Each flow step the fast-forward flow order can have labeled nucleotides. From the measured signal, distance information indicative of the length of the second region can be determined, for example based on the correlation between signal intensity and distance. The signal can be detected multiple times with the fast-forward region (e.g., after each flow step), and the set of signals can be used to determine the distance information indicative of the length of the second region.

The determined distance information is correlated with a measured signal detected within the fast-forward region. For example, a larger signal intensity a greater number of bases incorporated into the extending primer.

Sequencing signal can decrease as the primer is extended through the polynucleotide, for example due to under-incorporation of nucleotides as expected (e.g., lagging strands or strands that unexpectedly fail to progress termed “droop strands”). Detected signal strength may be normalized to correct for differing signal per incorporated base ratios across the fastforward region. Signal strength may also be normalized for differences in different sequencing clusters in a sequencing run.

Different fast-forward flow types (e.g., a “not-A” flow that includes C, G, and T nucleotides; a “not-C” flow that includes A, G, and T nucleotides; a “not-G” flow that includes A, C, and T nucleotides; or a “not-T” flow that includes A, C, and G nucleotides) may have different signals per base. To account for this, a normalized signal per base within the fast-forward flow region can be determined, for example using signals from within a sequencing region of the polynucleotide. For example, for a normalized signal per base for a not-A flow, nucleotide incorporation signal from the last X number of sequencing flows (wherein X is a desired number, such as between 5 and 40) that contained C, G, or T nucleotides (not A nucleotides) is summed and divided by the number of bases called in those flows. Similar normalized signals per base for other fast-forward flow types can similarly be determined. If a signal is measured after multiple flows (rather than after every flow), a number of bases incorporated into the sequencing primer can be determined for those multiple flows. That is, a signal obtained for a particular sequencing cluster for the multiple flows can be divided by the average normalized signal per base to determine a number of bases incorporated into the sequencing primer for those multiple flows. The distance information for the fast-forward region can then be the sum of the number of bases incorporated into the sequencing primer for all fast-forward flows of the fast-forward region.

Optionally, a number of bases incorporated into the primer for the flow or flows can be corrected to account for sequencing primers that failed to extend as expected (i.e., droop strands). The number of bases incorporated into the primer for the multiple flows for a particular sequencing cluster can be multiplied by a correction factor of the number of expected bases for the multiple flows divided by the average number of bases incorporated into the primer for the multiple flow across a plurality of sequencing clusters. The number of expected bases may be estimated, for example, based on the distribution of bases in the genome and the nucleotides present in the multiple flows. For example, given the distribution of bases in the human genome, a fast-forward cycle of four triplet nucleotide flows (e.g., not-A, not-C, not-G, and not-T), the expectation is that approximately 4.5 bases will be incorporated per flow, or about 18 for the cycle.

In another example, the distance information may be determined using a machine learning model. For example, a neural network can be trained using control polynucleotides having a known length (ground truth) and signals detected while extending the primer through a fast forward region using a fast forward flow order. The neural network can be trained to associate a detected signal with a number of bases per flow or per flow order (or cycle). A measured signal can then be inputted into the trained machine learning model, which outputs the distance of the fast-forward region.

The primer may be extended through the sequencing region and the fast-forward region in either order. That is, in some embodiments, the primer is hybridized to the polynucleotide, and the primer is extended through a fast-forward region according to a fastforward flow region order before being extended through a sequencing region (i.e., generating sequencing data) according to a sequencing region flow order. In some embodiments, the primer is hybridized to the polynucleotide, and the primer is extended through a sequencing region (i.e., generating sequencing data) according to a sequencing region flow region order before being extended through a fast-forward region according to a fast-forward region flow order. In some embodiments, sequencing data is generated for two sequencing regions that are separated by a fast-forward region, and the primer can be extended through the first sequencing region, then the fast-forward region, then the second sequencing region.

Expected Sequencing Data

A reference sequence can be used to determine expected sequencing data (such as a flowgram) for the first region, the second region, and/or the third region. The sequence for the first and third regions can be determined from the generated sequencing data for those regions. For example, in reference to Table 2, Cycle 1 is associated with the first region, for which the sequence is readily determined as the complement to the bases (i.e., base flow AC-T-G corresponds to a sequence of TGAC), and Cycles 4 and 5 are associated with the third region, for which the sequence is determined as CTGAC (i.e., the complement of G-A-C-TG). Thus, using the generated sequencing data from the first region and/or the third region, the first region and/or the third region (or at least a portion of the first region and/or the third region) can be mapped to the reference sequence. Once mapped to reference sequence, expected sequencing data for the second region can be generated using the flow order used to extend the primer through the second region and the reference sequence.

Expected sequencing data may also be determined for the third region using the reference sequence for the second region, the flow order for the second region, the flow order for the third region, and information about the sequence of the third region. Similarly, expected sequencing data may be determined for the first region using the reference sequence for the second region, the flow order for the second region, the flow order for the first region, and information about the sequence of the first region. The information about the sequence of the third region (or first region) may be obtained from, for example, the reference sequence (or a different reference sequence) or generated sequencing data such as the sequencing data generated by extending the primer using labeled nucleotides and detecting the presence or absence of an incorporated labeled nucleotide, or sequencing data obtained by other methods (e.g., independently sequencing the third region of the third region of the polynucleotide).

By way of example, the expected sequencing data for the third region may be determined using a reference sequence for the second region, the second region flow order, the third region flow order, and a reference sequence for the third region. The first region (or a portion thereof) may be mapped to a reference sequence, and the reference sequence corresponding to the second region and the second region flow order may be used to determine expected reference sequencing data for the second region. Similarly, the reference sequence for the third region may be used, along with the third region flow order, to determine an expected reference sequencing data for the third region. The expected sequencing data for the first region may be determined using a similar method. For example, the expected sequencing data for the first region may be determined using a reference sequence for the second region, the second region flow order, the first region flow order, and a reference sequence for the first region. The third region (or a portion thereof) may be mapped to a reference sequence, and the reference sequence corresponding to the second region and the second region flow order may be used to determine expected reference sequencing data for the second region. Similarly, the reference sequence for the first region may be used, along with the first region flow order, to determine an expected reference sequencing data for the first region.

In another example, the expected sequencing data for the third region may be determined using a reference sequence for the second region, the second region flow order, the third region flow order, and sequencing data associated with the sequenced of the third region, which may be the same or different from the sequencing data generated as previously described. The first region (or a portion thereof) may be mapped to a reference sequence, and the reference sequence corresponding to the second region and the second region flow order may be used to determine expected reference sequencing data for the second region. The sequencing data for the third region may be used to determine the sequence of the third region. Further the sequence of the third region may be used, along with the third region flow order, to determine expected sequencing data for the third region.

Figure 2:
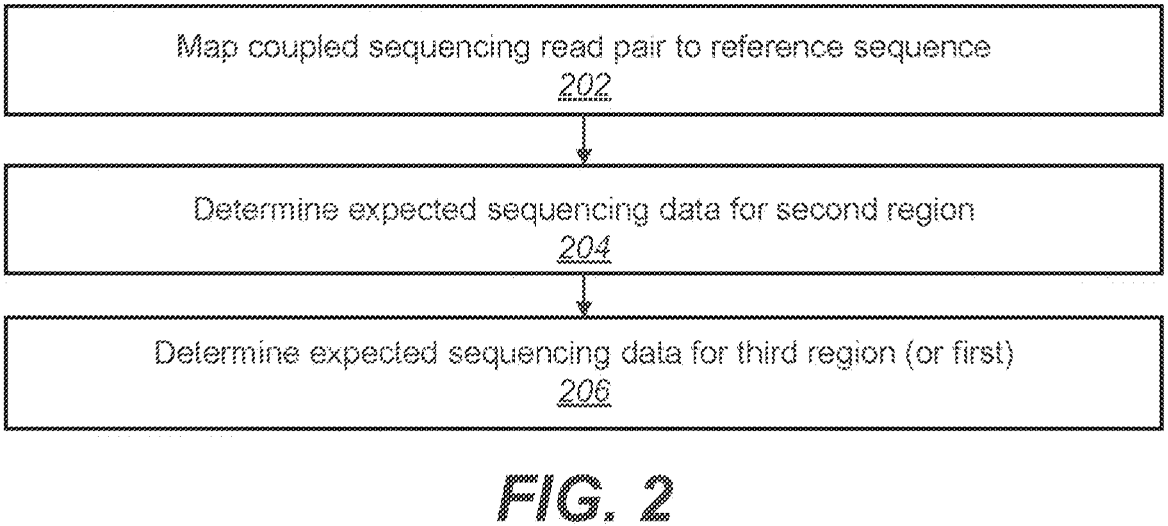
FIG. 2 illustrates a schematic of an exemplary method for generating expected sequencing data using a reference sequence.

FIG. 2 illustrates a schematic of an exemplary method for generating expected sequencing data. At step 202, the coupled sequencing read pair is mapped to a reference sequence. Mapping the coupled sequencing read pair may include mapping the first region (or portion thereof) of the coupled sequencing read pair (or portion thereof) to the reference sequence, mapping the third region (or portion thereof) of the coupled sequencing read pair to the reference sequence, or both the first region (or portion thereof) and the third region (or portion thereof) to the reference sequence. At step 204, the expected sequencing data (such as an expected flowgram) for the second region is determined using the second region flow order and the reference sequence. With the flow order and reference sequencing known, determining the expected sequencing data (that is, the sequencing data that would be expected if the second region of the polynucleotide matches the reference sequence) is readily obtainable. Further, the expected sequencing data for the second region can be used to determine the expected 5' end of the second region. The 5' end of the second region may vary depending on the flow order for that region and the sequence of the second region. Thus, the 3' end of the third region can also vary based on the second region flow order and sequence of the second region because the 3' end of the third region is adjacent to the 5' end of the second region. Once the 3' end of the third region is established (for example, as determined using the expected sequencing data for the second region), the expected sequencing data for the third region can be determined, as shown in step 206. As further described herein, the expected sequencing data for the third region may be used to determine variants, such as a variant within the second region of the polynucleotide.

If the polynucleotide includes a variant within the second region, the generated sequencing data (e.g., the flowgram) associated with the third region may differ (depending on the sequence context and the size of the variant) from the expected sequencing data associated with the third region. Thus, in some embodiments, variants are detected based on the difference between the expected sequencing data and the generated sequencing data.

The reference sequence may be any suitable sequence of the same species as the polynucleotide, and there may be some differences between the reference sequence and the sequence of the polynucleotide. In some embodiments of the methods described herein, these differences, or variants, can be detected. In some embodiments, a test variant (i.e., a variant of interest) is included in the reference sequence, and in other embodiments, the test variant is omitted from the reference sequence. In some embodiments, the analysis may be performed with two different reference sequences, with one reference sequence including the test variant and the other reference sequence omitting the test variant. In some embodiments, the only difference between the two reference sequences is the presence or absence of the test variant.

The sensitivity of the variant detection methods described herein may depend on the context of the variant and/or the flow order used to extend the primer in the first, second and/or third region. A missed variant with a given flow order may be detectable using a different flow order in the first, second and/or third region. Accordingly, in some embodiments of the method described herein, the more than one coupled sequencing read pair is generated using different flow orders for extending the primer through one or more of the first, second, and/or third region of the polynucleotide.

Mapping a Coupled Sequencing Read Pair to a Reference Sequence

A coupled sequencing read pair can be mapped to a reference sequence, which may or may not include a test variant of interest. The sequencing data for the first region or the third region can be used to derive the sequence of the first region or the third region, respectively. The first region or a portion of the first region, or the third region or a portion of the third region, can be mapped to the reference sequence. The distance between the first region and the third region (i.e., the length of the second region) can be determined or estimated, for example using the distance information indicative of the length of the second region determined using measured signal or signals from labeled nucleotides incorporated into the primer as it is extended in the second region, thereby providing an approximate locus for the unmapped third or first region. Using the approximate locus, the unmapped first or third region can then be readily mapped to the reference sequence.

A mapped sequence refers to an alignment of one sequence (such as the sequence of a region or a portion thereof) to another sequence (such as a reference sequence). A mappable sequence is a sequence (such as a sequence of a region or portion thereof) that may be mapped another sequence (such as a reference sequence) in accordance with a selected mapping threshold (i.e., a mapping score). An unmappable sequence, therefore, is a sequence that is not mappable to the other sequence in accordance with the selected mapping threshold (mapping score). The score may be predetermined (i.e., selected prior to mapping) based on an error risk tolerance. The Smith-Waterman algorithm may be used when mapping one sequence to another, for example, and the mapping threshold can be selected to distinguish a "mappable" sequence from an "unmappable" sequence. Bay way of example, the mapping score threshold may be +5 or higher, +6 or higher, +8 or higher, +10 or higher, +12 or higher, +14 or higher, +16 or higher, +18 or higher, or +20 or higher with a matching score of +1, a mismatch score of −1, a gap opening score of −2, and a gap extension score of −2. Other scores or penalty scores may be selected by one skilled in the art.

A sequence, such as one or more regions of a coupled sequencing read pair, can be mapped with any suitable mapping software, such as GATK, Bowtie, Bowtie2, BWA, BWA-MEM, Novoalign, SOAP2, SOAP3, and others including other Burrows-Wheeler transform (BWT)-based aligners. See for example, Miller et al., *Assembly algorithms for next-generation sequencing data*, Genomics, vol. 95, pp. 315-327 (2010); Chaisson et al., *De novo fragment assembly with short mate paired reads: Does the read length matter?* Genome Research, vol. 19, pp. 336-346 (2009); Mielczarek et al., *Review of alignment and SNP calling algorithms for next-generation sequencing data*, J. Appl. Genetics, vol. 57, pp. 71-79 (2016); Nielsen et al., *Genotype and SNP calling from next-generation sequencing data*, Nature Reviews Genetics, vol. 2, pp. 443-451 (2011); and Hwang et al., *Systematic comparison of variant calling pipelines using gold standard personal exome variants*, Sci Rep., vol. 5, 17875 (2015); each of which is incorporated herein by reference for all purposes.

The use of distance information to approximate the locus of a region of the polynucleotide to the reference sequence is useful for detecting structural variants (such as insertions or deletions) within the second region of the polynucleotide, or to resolve multiple mappable loci within the genome (for example, when the first region or the third region includes a repeat region or other non-unique sequence).

The distance information can be used to map the coupled sequencing read pair to a reference sequence when more than one mappable positions are available within the reference sequence. For example, in some embodiments, the first region can be mapped to the reference sequence with a high confidence, but the third region may map to a plurality of different locations within the reference sequence. In some embodiments, the third region can be mapped to the reference sequence with a high confidence, but the first region may map to a plurality of different locations within the reference sequence. In some embodiments, both the first region and the third region can be mapped to a plurality of different locations within the reference sequence. The correct position pair for the first region and the second region mapped to the reference sequence can be selected using the distance information for the second region. For example, a method of mapping a coupled sequencing read pair to a reference sequence can include mapping a first region (or portion thereof) and a third region (or portion thereof) of a coupled sequencing read pair to a reference sequence at two or more different position pairs comprising a first position and a second position. Distance information indicative of the length of the second region of the polynucleotide can then be compared to the distance between the mapped first position and the mapped second position. If the compared distance information approximate each other or match, the correct position pair can then be selected. If, however, the length of the second region is significantly different from the distance between the first position and the second position, that position pair can be rejected.

Figure 3:
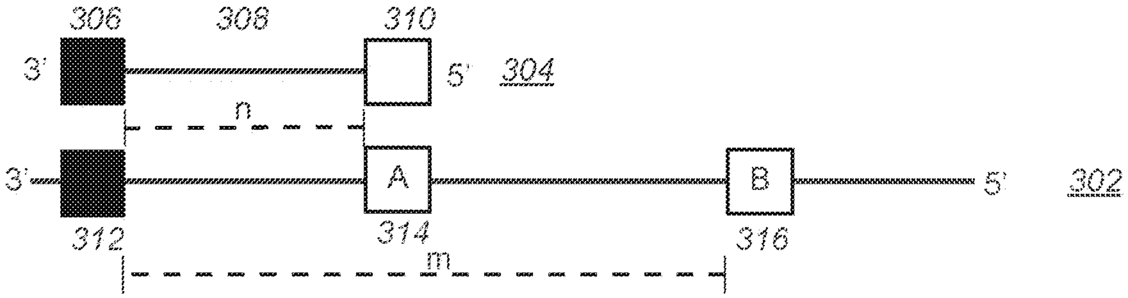
FIG. 3 illustrates how a coupled sequencing read pair is mapped to a reference sequence using distance information indicative of the length of the second region of the coupled sequencing read pair when the third region of the coupled sequencing read pair maps to two different loci.

FIG. 3 illustrates how a coupled sequencing read pair is mapped to a reference sequence using distance information indicative of the length of the second region of the coupled sequencing read pair. The coupled sequencing read pair 304 includes first region 306, a second region 308 and a third region 310. The first region 306 can map to the reference first region 312 of a reference sequence 302, but the third region 310 can map to both reference third region, option A, 314, and the reference third region, option B, 316. The distance between the end of the reference first region 312 and the start of the reference third region, option A, 314 is n bases in length (based on the reference sequence), and the distance between the end of the reference first region 312 and the start of the reference third region, option B, 316 is m bases in length (based on the reference sequence). The distance information for the second region indicates that the length of the second region is approximately n bases in length. Therefore, it can be concluded that the third region 310 properly maps to reference third region, option A, 314. A similar analysis may be performed even if there are multiple mappable loci for the first region and/or multiple mappable loci for the third region.

Figure 4:
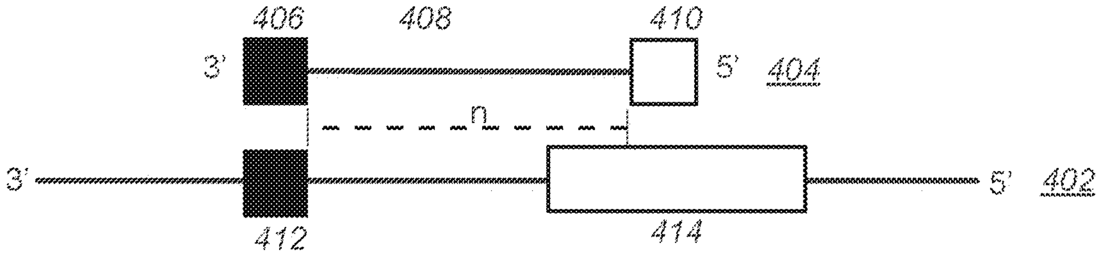
FIG. 4 illustrates how a coupled sequencing read pair is mapped to a reference sequence using distance information indicative of the length of the second region of the coupled sequencing read pair when the third region of the coupled sequencing read pair maps to a repeat region.

Furthermore, the distance information can be used to map the coupled sequencing read pair to a reference sequence when the first region or the third region cannot be definitively mapped to an exact location because of a repeat region at the locus of the first region or the third region. FIG. 4 illustrates how a coupled sequencing read pair is mapped to a reference sequence using distance information indicative of the length of the second region of the coupled sequencing read pair when the third region of the coupled sequencing read pair maps to a repeat region. FIG. 4 shows a reference sequence 402 and a coupled sequencing read pair 404. The coupled sequencing read pair includes first region 406, a second region 408 and a third region 410. The first region 406 can map to a specific locus within the reference first region 412, but the third region 410 can map anywhere within a repeat region 414. By knowing the length of the second region 408, the third region 410 can be more accurately mapped within the repeat region 414. For example, if the length of the second region 408 is approximately n bases in length, this distance information can be used to position the third region 410 once the first region 406 has been mapped. Similarly, this method can be used when the third region can be precisely mapped but the first region maps within a repeat region.

Detection of a Structural Variant

The coupled sequencing read pairs generated from a polynucleotide derived from genome can be used to detect a variant, such as a structural variant within the genome. Structural variants can include insertion, deletion, inversion, and chromosomal fusion variants, which may be located within the first, second, or third region of the polynucleotides, or may be located at a position bridging the first, second or third region of the polynucleotide.

An insertion in a genome may be of any size, such as between 1 base in length to hundreds or thousands of kilobases or more in length. Further, the insertion may be and endogenous insertion (that is, a sequence inserted into a locus originating from elsewhere in the subject's genome), or may be an exogenous insertion (such as a sequence inserted into a locus originating from a source other than the subject's genome, such as a viral genome inserted into the subjects genome). Exogenous insertions result in nucleic acid sequences that are not present within the reference sequence, posing an additional challenge for detecting or locating exogenous insertion variants within the subject's genome. The methods described herein can be used to detect and/or locate an exogenous insertion, among other structural variants.

Figure 5:
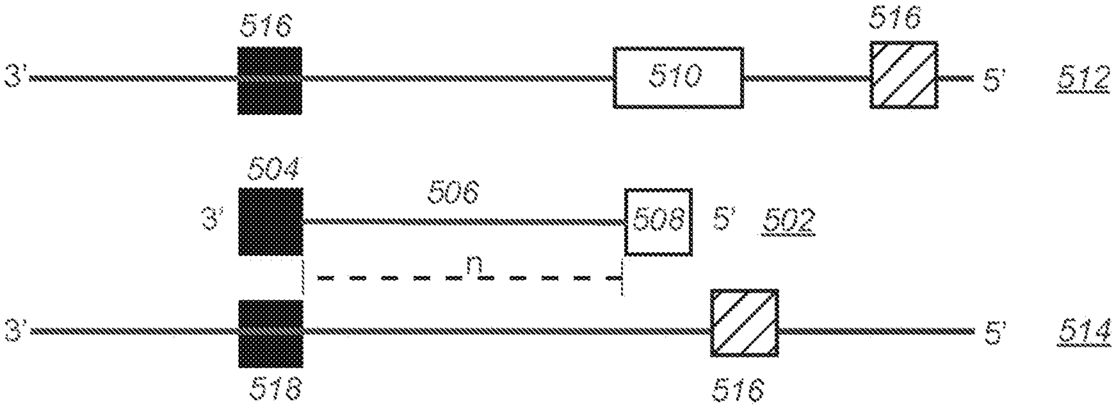
FIG. 5 illustrates a schematic for how a coupled sequencing read pair can be used to detect an insertion in a subject's genome.

In one example, a method of detecting a structural variant (such as an exogenous insertion) within a genome using a coupled sequencing read pair includes mapping the first region (or portion thereof) of the coupled sequencing read pair to a reference sequence, and attempting to map the third region (or portion thereof) to the reference sequence. If the third region (or portion thereof) is unmappable, then the presence of an exogenous insertion can be identified. This is because the reference sequence does not include a sequence corresponding to the third region. Similarly, a method of detecting an exogenous insertion within a genome using a coupled sequencing read pair can include mapping the third region (or portion thereof) of the coupled sequencing read pair to a reference sequence, and attempting to map the first region (or portion thereof) to the reference sequence. If the first region (or portion thereof) is unmappable, then the presence of an exogenous insertion can be identified. This is because the reference sequence does not include a sequence corresponding to the first region. Further (and in either example), the locus of the exogenous insertion within the reference sequence can be determined based on distance information indicative of the length of the second region, for example using the distance information indicative of the length of the second region determined using measured signal or signals from labeled nucleotides incorporated into the primer as it is extended in the second region. FIG. 5 illustrates a schematic for an exemplary method of detecting an exogenous insertion. The coupled sequencing read pair 502 includes a first region 504, a second region 506, and a third region 508, with the second region 506 between the first region 504 and the third region 508. The third region 508 includes an exogenous insertion element 510 present in the subject's genome 512, although not present in the reference sequence 514. Reference element 516 is present in both the subject's genome 512 and the reference sequence 514, although is spaced differently from the reference first region 518. The first region 504 maps to reference first region 518 within the reference sequence. However, the third region 508 does not have a corresponding region on which to map (i.e., it is unmappable) within the reference sequence 514. This indicates that the sequence of the third region 508 is the result of an exogenous insertion within the subject's genome. Distance information for the second region 506 can also be used to determine the locus of the exogenous genome relative to the reference first region 518. That is, if the second region 506 is approximately n bases in length, the exogenous insert is positioned approximately n bases from the end of the first region 504.

In another example, the coupled sequencing read pair can be used to detect a structural variant (such as an insertion, deletion, inversion, or chromosomal fusion) using expected sequencing data, and comparing the generated sequencing data to expected sequencing data. For example, one of the first region (or a portion thereof) or the third region (or portion thereof) of a coupled sequencing read pair can be mapped to a reference sequence. A locus within the reference sequence for the unmapped first region (or portion thereof) or the unmapped third region (or portion thereof) can be determined using distance information indicative of the length of the second region. The distance information can be determined, for example, as described herein. Once the locus for the unmapped first region (or portion thereof) or unmapped third region (or portion thereof) is determined, expected sequencing data reference sequence at the locus can be determined. For example, the expected sequence data may be determined based on the sequence of the second region, the second region flow order, information related to the sequence of the unmapped region, and the unmapped region flow order. The expected sequencing data can then be compared to the generated sequencing data of the unmapped region. A difference between the sequencing data of the unmapped region and the expected sequencing data indicates a structural variant at the locus.

Figure 6:
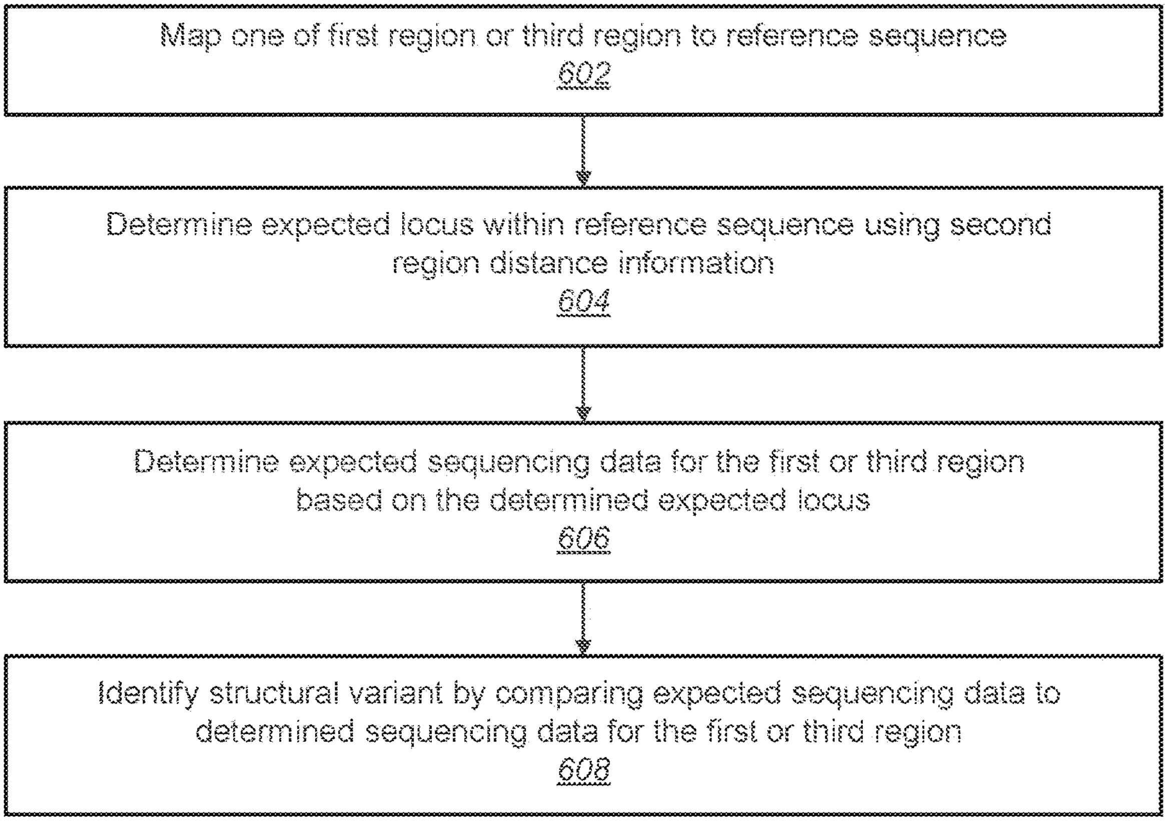
FIG. 6 illustrates an exemplary method for detecting a structural variant using a coupled sequencing read pair.

FIG. 6 illustrates an exemplary method for detecting a structural variant using a coupled sequencing read pair. At step 602, one of the first region or portion thereof (or the third region or portion thereof) is mapped to a reference sequence. At step 604, an expected locus within a reference sequenced is determined for the third region or portion thereof (or first region or portion thereof). This is, if the first region or portion thereof is mapped during step 602, the expected locus for the third region or portion thereof is determined at step 604, and if the third region or portion thereof is mapped during step 602, the expected locus for the first region or portion thereof is determined at step 604. At step 606, an expected sequencing data at the determined expected locus for the third region or portion thereof (or the first region or portion thereof) is determined. At step 608, the expected sequencing data for the third region or portion thereof (or the first region or portion thereof) is compared to determined sequencing data for the third region or portion thereof (or the first region or portion thereof), wherein a difference between the determined sequencing data and the expected sequencing data indicates a structural variant.

Figure 7:
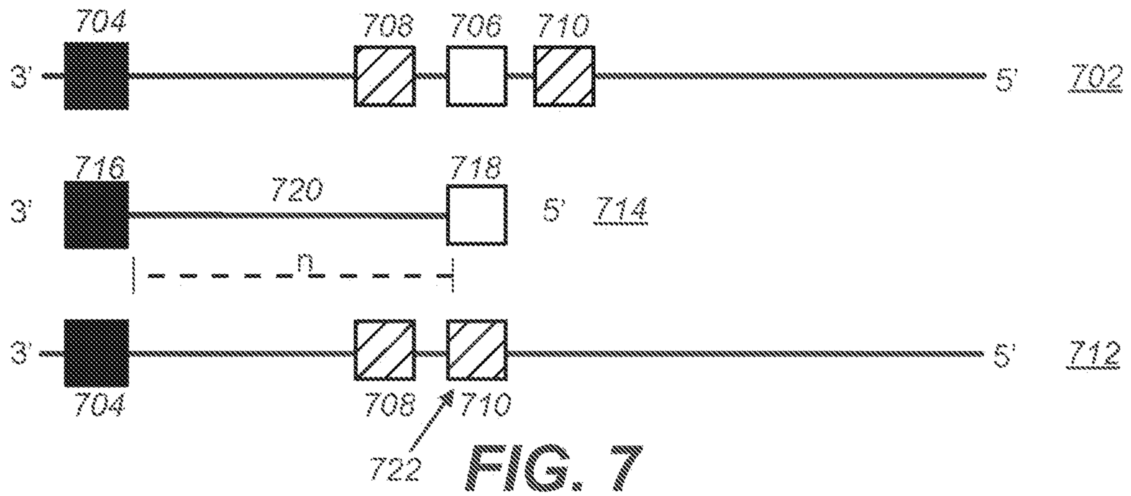
FIG. 7 illustrates a schematic for using a coupled sequencing read pair for detecting a structural variant in the subject's genome, wherein the structural variant is an insertion.

FIG. 7 illustrates a schematic for using a coupled sequencing read pair for detecting a structural variant in the subject's genome, wherein the structural variant is an insertion. The subject's genome 702 includes a first region 704 and an insertion 706 between a first reference region 708 and a second reference region 710. The reference sequence 712 includes the first region 704, the first reference region 708, and the second reference region 710, but does not include the insertion 706 between the first reference region 708 and the second reference region 710 (the insertion may correspond to a region found in another portion of the reference region, or may be an entirely exogenous sequence). The coupled sequencing read pair 714 includes a first region 716 (corresponding to first region 704) and a third region 718 (corresponding to the insertion 706), which separate a second region 720. The first region 716 of the coupled sequencing read pair 714 maps to the first region 704 of the reference sequence 712. Distance information indicates the length of the second region 720 of the coupled sequencing read pair 714 as approximately n bases in length. Therefore, the start of the expected locus 722 for the third region 718 is determined to start approximately n bases from the end of the first region 704. Expected sequencing data can then be determined for the expected locus as described herein. For example, expected sequencing data may be determined for the expected locus using the reference sequence 712 (for example, the reference sequence between the first region 704 to and/or including the expected locus), the flow order for the second region, and the flow order for the third region. In the example illustrated in FIG. 7, the expected sequencing data corresponds to sequencing data that would have been obtained if the third region 718 was the second reference region 710, as the second reference region 710 is at the expected locus. If the expected sequencing data for the expected locus differs from the generated sequencing data for the third region 718 of the coupled sequencing read pair 714 (which is the circumstance of the example illustrated in FIG. 7), then the structural variant is detected.

Figure 8:
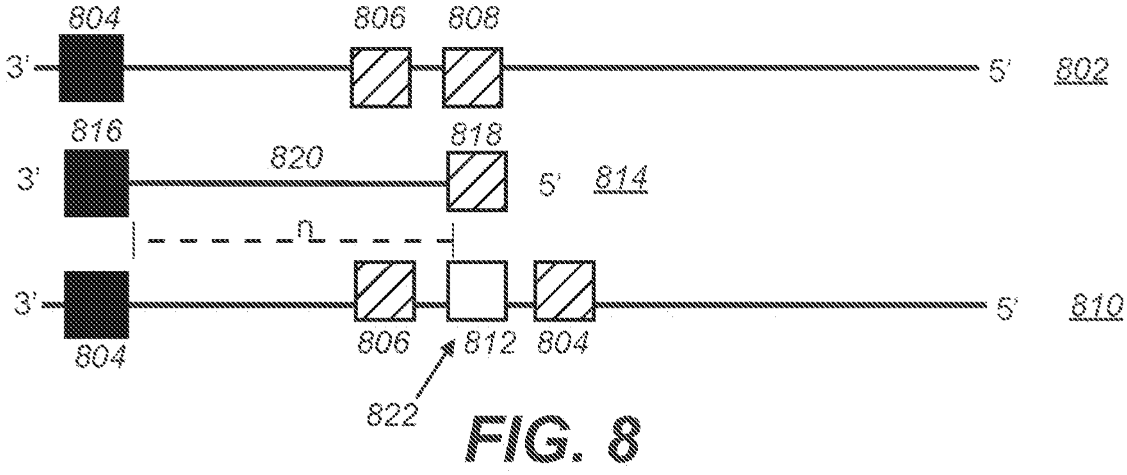
FIG. 8 illustrates a schematic for using a coupled sequencing read pair for detecting a structural variant in the subject's genome, wherein the structural variant is a deletion.

FIG. 8 illustrates a schematic for using a coupled sequencing read pair for detecting a structural variant in the subject's genome, wherein the structural variant is a deletion. The subject's genome 802 includes a first region 804, first reference region 806, and a second reference region 808. The reference sequence 810 includes the first region 804, the first reference region 806, and the second reference region 808, along with an additional region 812 positioned between the first reference region 806 and the second reference region 808. Although the additional region 812 is present in the reference sequence 810, the additional region 812 has been deleted from the subject's genome 802. The coupled sequencing read pair 814 includes a first region 816 (corresponding to first region 804) and a third region 818 (corresponding to the second reference region 808), which separate a second region 820. The first region 816 of the coupled sequencing read pair 814 maps to the first region 804 of the reference sequence 810. Distance information indicates the length of the second region 820 of the coupled sequencing read pair 814 as approximately n bases in length. Therefore, the start of the expected locus 822 for the third region 818 is determined to start approximately n bases from the end of the first region 804. Expected sequencing data can then be determined for the expected locus as described herein. For example, expected sequencing data may be determined for the expected locus using the reference sequence 812 (for example, the reference sequence between the first region 804 to and/or including the expected locus), the flow order for the second region, and the flow order for the third region. In the example illustrated in FIG. 8, the expected sequencing data corresponds to sequencing data that would have been obtained if the third region 818 was the additional region 812 (deleted in the subject's genome), as the additional region 812 is at the expected locus. If the expected sequencing data for the expected locus differs from the generated sequencing data for the third region 818 of the coupled sequencing read pair 814 (which is the circumstance of the example illustrated in FIG. 8), then the structural variant is detected.

Figure 9:
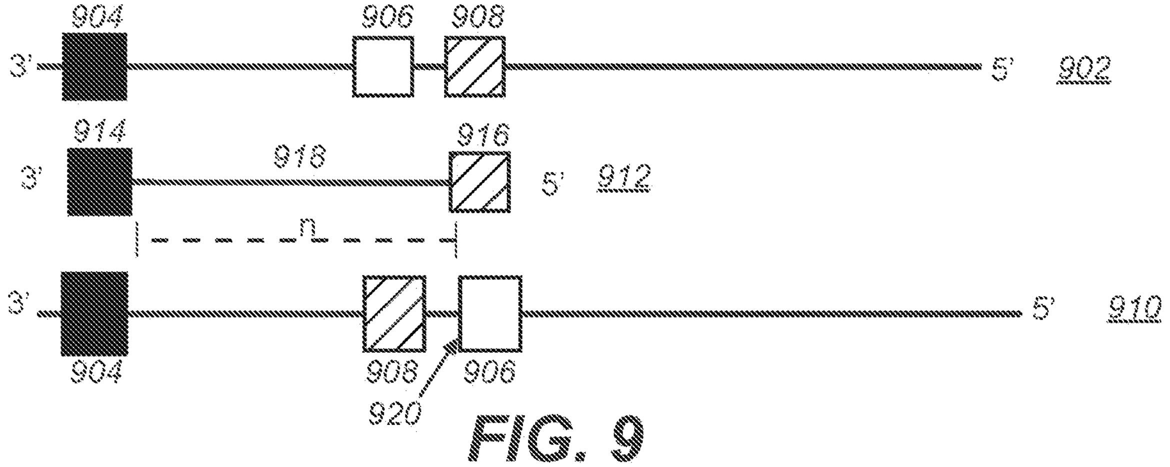
FIG. 9 illustrates a schematic of using a coupled sequencing read pair for detecting a structural variant in the subject's genome, wherein the structural variant is an inversion.

FIG. 9 illustrates a schematic of using a coupled sequencing read pair for detecting a structural variant in the subject's genome, wherein the structural variant is an inversion. The subject's genome 902 includes a first segment 904, a second segment 906, and a third segment 908. The reference sequence 910 also includes the first segment 904, the second segment 906, and the third segment 908. However, in the reference sequence 910, the second segment 906 is proximal to the 5' end relative to the third segment 908, whereas in the subject's genome 902, the second segment 906 is proximal to the 3' end relative to the third segment 908. Thus, the second segment 906 and the third segment 908 in the subject's genome 902 are inverted relative to the reference sequence 910. The coupled sequencing read pair 912 includes a first region 914 (corresponding to first segment 904) and a third region 916 (corresponding to the third segment 908), which separate a second region 918. The first region 914 of the coupled sequencing read pair 912 maps to the first segment 904 of the reference sequence 910. Distance information indicates the length of the second region 918 of the coupled sequencing read pair 912 as approximately n bases in length. Therefore, the start of the expected locus 920 for the third segment 908 is determined to start approximately n bases from the end of the first segment 904. Expected sequencing data can then be determined for the expected locus as described herein. For example, expected sequencing data may be determined for the expected locus using the reference sequence 910 (for example, the reference sequence between the first segment 904 to and/or including the expected locus), the flow order for the second region, and the flow order for the third region. In the example illustrated in FIG. 9, the expected sequencing data corresponds to sequencing data that would have been obtained if the third region 916 corresponded with the second segment 906, as the second segment 906 (and not the third segment 908) is at the expected locus in the reference sequence 910. If the expected sequencing data for the expected locus differs from the generated sequencing data for the third region 916 of the coupled sequencing read pair 912 (which is the circumstance of the example illustrated in FIG. 9), then the structural variant is detected.

Figure 10:
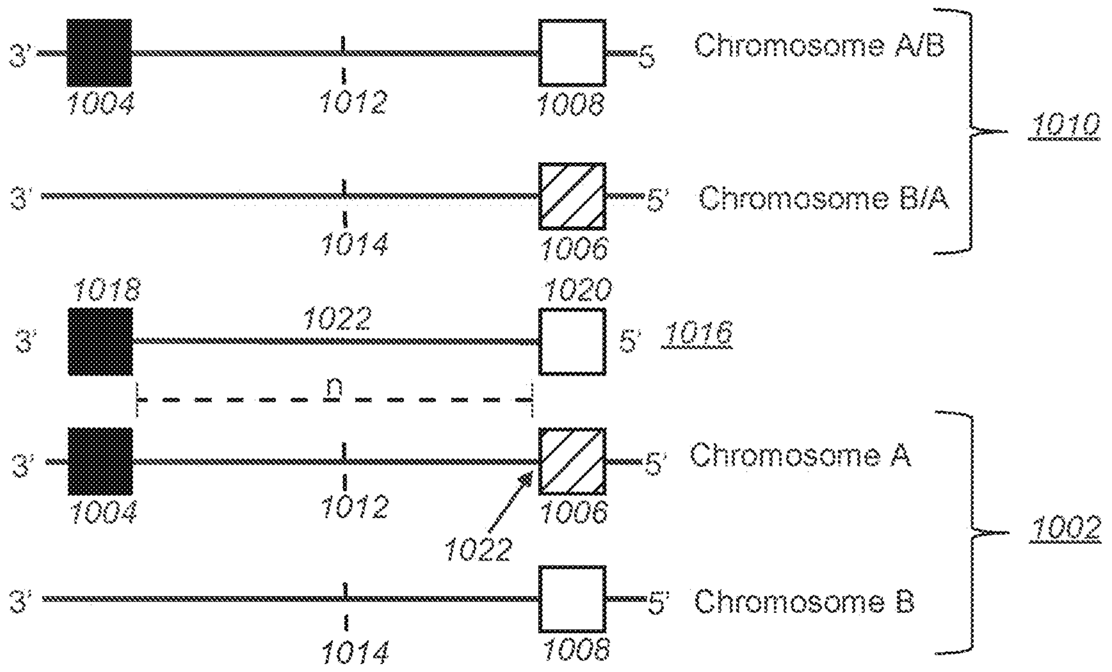
FIG. 10 illustrates a schematic for using a coupled sequencing read pair for detecting a structural variant in the subject's genome, wherein the structural variant is a chromosomal fusion.

FIG. 10 illustrates a schematic for using a coupled sequencing read pair for detecting a structural variant in the subject's genome, wherein the structural variant is a chromosomal fusion. A chromosomal fusion results from a chromosomal rearrangement event, wherein a portion of a chromosome fuses to another portion of a chromosome (either the same chromosome or a different chromosome). The reference sequence 1002 includes Chromosome A, which includes first segment 1004 and second segment 1006, and Chromosome B, which includes third segment 1008. The subject's genome 1010 includes a chromosomal fusion of Chromosome A and Chromosome B at points 1012 and 1014 of the reference genome 1002. This results in Chromosome A/B, which includes the 3' end of Chromosome A and the 5' end of Chromosome B, and Chromosome B/A, which includes the 3' end of Chromosome B and the 5' end of Chromosome A. Thus, Chromosome A/B includes first segment 1004 and third segment 1008, and Chromosome B/A includes second segment 1006. A coupled sequencing read pair 1016 is derived from Chromosome A/B of the subject's genome 1010, and includes a first region 1018 (corresponding to first segment 1004) and a third region 1020 (corresponding to the third segment 1008), which separate a second region 1022. The first region 1018 of the coupled sequencing read pair 1016 maps to the first segment 1004 of the reference genome 1002. Distance information indicates the length of the second region 1022 of the coupled sequencing read pair 1016 as approximately n bases in length. Therefore, the start of the expected locus 1024 for the third segment 1020 is determined to start approximately n bases from the end of the first segment 1004. Expected sequencing data can then be determined for the expected locus as described herein. For example, expected sequencing data may be determined for the expected locus using Chromosome A of the reference sequence 1002 (for example, the reference sequence between the first segment 1004 to and/or including the expected locus, second segment 1006), the flow order for the second region 1022, and the flow order for the third region 1020. In the example illustrated in FIG. 10, the expected sequencing data corresponds to sequencing data that would have been obtained if the third region 1020 corresponded with the second segment 1006, as the second segment 1006 (and not the third segment 1008) is at the expected locus in the reference sequence 1002. If the expected sequencing data for the expected locus differs from the generated sequencing data for the third region 1020 of the coupled sequencing read pair 1016 (which is the circumstance of the example illustrated in FIG. 10), then the structural variant is detected.

The junction of the structural variant (e.g., the insertion, deletion, chromosomal fusion, or inversion) relative to the reference sequence need not span the entirety of the first region or the third region of the coupled sequencing read pair. In some embodiments, at least a portion of the structural variant terminates within the first region or the third region of the coupled sequencing read pair. The expected sequencing data will still differ from the determined sequencing data for the first or third region.

Detection of a Variant within the Second Region

In some embodiments, the coupled sequencing read pair is used to detect a variant within the second region, even though the incorporation of nucleotides into the primer extended through the second region need not be detected. Detectable variants include structural variants (such as an insertion, deletion, inversion, or chromosomal fusion) or a single nucleotide polymorphism (SNP).

A method of detecting a structural variant (e.g., chromosomal fusion, inversion, insertion, or deletion) can include mapping both a first region (or portion thereof) and a third region (or portion thereof) of a coupled sequencing read pair to a reference sequence. Distance information between the first region mapped to the reference sequence and the third region mapped to the reference sequence (i.e., mapped distance information) can be determined. The mapped distance information is indicative of the distance between the mapped position of first region mapped to the reference sequence and the mapped position of the third region mapped to the reference sequence, for example a number of bases between the first and third mapped regions. A comparison between the determined distance information and the mapped distance information can be used to detect the structural variant. For example, if the determined distance is shorter than the mapped distance, then a structural variant such as an insertion or a chromosomal fusion variant within the subject's genome is indicated. If the determined distance is longer than the mapped distance, then a deletion variant within the subject's genome is indicated.

Figure 11:
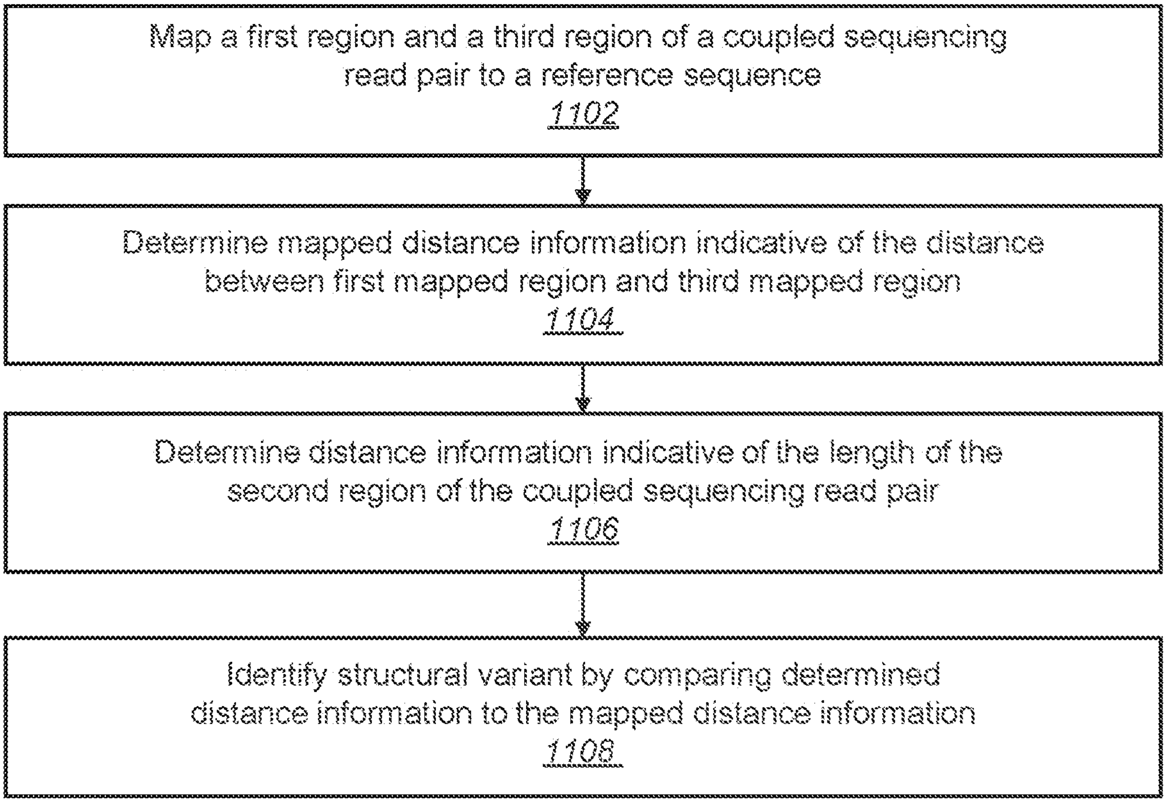
FIG. 11 illustrates an exemplary method of detecting a structural variant using a coupled sequencing read pair.

FIG. 11 illustrates an exemplary method of detecting a structural variant that includes, at step 1102, mapping a first region (or a portion thereof) and a third region (or portion thereof) of a coupled sequencing read pair to a reference sequence. A step 1104, a mapped sequence distance information is determined indicative of the distance between the first region mapped to the reference sequence and the third region mapped to the reference sequence. At step 1106, a distance information for the second region is determined using the method described herein, for example using measured signal or signals from labeled nucleotides incorporated into the primer as it is extended in the second region. At step 1108, a structural variant is identified by comparing the determined distance information to the mapped distance information, wherein a difference between the mapped distance information and the determined distance information indicates the structural variant.

Figure 12:
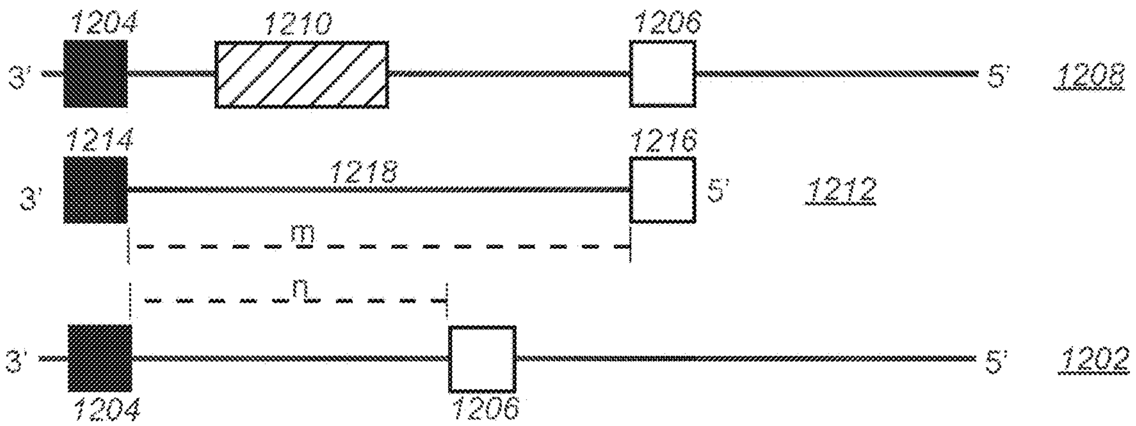
FIG. 12 illustrates a schematic demonstrating one example of how a coupled sequencing read pair can be used to detect a structural variant using distance information indicative of the length of the second region of the coupled sequencing read pair.

FIG. 12 illustrates a schematic demonstrating one example of how a coupled sequencing read pair can be used to detect a structural variant. The illustrated example shows an insertion in the subject's genome, but the methodology is similarly applied to other structural variants (e.g., deletions or chromosomal fusions). The reference sequence 1202 includes a first segment 1204 and a second segment 1206. The subject's genome 1208 also includes the first segment 1204 and the second segment 1206, but further includes an insert 1210 between the first segment 1204 and the second segment 1206. A coupled sequencing read pair 1212 generated from the subject's genome 1208 includes a first region 1214 corresponding to the first segment 1204 and a third region 1216 corresponding to the second segment 1206. A second region 1218 separates the first region 1214 and the third region 1216. The sequence of the first region 1214 and the third region 1216 can be mapped to the reference sequence 1202 at the first segment 1204 and the second segment 1206, respectively. Once mapped, the mapped distance information indicative of the distance between the first region 1214 and the third region 1216 mapped to the reference sequence 1202 (i.e., the distance between the first segment 1204 and the second segment 1206 of the reference sequence 1202) is determined as a distance of n. Determined distance information for the length of the second region 1218 can also be determined as m. The structural variant can then be determined by comparing the mapped distance information n to the determined distance information m.

In another method of detecting a variant (such as a structural variant or a SNP) within the second region, expected sequencing data is compared to determined sequencing data. For example, in some embodiments, a method of detecting a variant between two sequenced regions of a coupled sequencing read pair (with the primer having been extended through the first region using nucleotides provided in a first region flow order and/or the primer having been extended through the third region using nucleotides provided in a third region flow order) includes mapping the first region (or a portion thereof) and/or the third region (or portion thereof) to a reference sequence. Expected reference sequencing data for the other region or portion thereof (i.e., if the first region or portion is mapped, the other region refers to the third region or portion thereof; and if the third region or portion thereof is mapped, the other region refers to the first region or portion thereof) is then determined. The expected sequencing data can be determined, for example, using a reference sequence for the second region, the second region flow order, the reference sequence for the other region or portion thereof (i.e., the third region or portion thereof if the first region or portion thereof is the region that is mapped, and the first region or portion thereof if the third region or portion thereof is the region that is mapped), and the flow order for the other region or portion thereof. In another example, the expected sequencing data is determined using a reference sequence for the second region, the second region flow order, a flow order for the other region, and sequencing data associated with the sequence of the other region (which may be the same sequencing data generated when generating the coupled sequencing read pair, or sequencing data generated by other means). The determined expected sequencing data for the other region can be compared to generated sequencing data for the other region. A difference between the expected and generated sequencing data indicates the presence of a variant.

In some embodiments a method of detecting a variant (such as a structural variant (e.g., a chromosomal fusion, an inversion, an insertion, or a deletion) or a SNP) between two sequenced regions of a coupled sequencing read pair, wherein the primer is extended using nucleotides provided in a third region flow order, includes mapping the first region or portion thereof to a reference sequence; determining expected sequencing data for the third region or portion thereof using (1) a reference sequence for the second region, the second region flow order, the third region flow order, and a reference sequence for the third region, or (2) a reference sequence for the second region, the second region flow order, the third region flow order, and generated sequencing data associated with the sequence of the third region; and detecting the presence of a variant by comparing the expected sequencing data for the third region to the generated sequencing data associated with the sequence of the third region. In some embodiments, a method of detecting a variant (such as a structural variant (e.g., a chromosomal fusion, an inversion, an insertion, or a deletion) or a SNP) between two sequenced regions of a coupled sequencing read pair, wherein the primer is extended using nucleotides provided in a first region flow order, includes mapping the third region or portion thereof to a reference sequence; determining expected sequencing data for the first region or portion thereof using (1) a reference sequence for the second region, the second region flow order, the first region flow order, and a reference sequence for the first region, or (2) a reference sequence for the second region, the second region flow order, the first region flow order, and generated sequencing data associated with the sequence of the first region; and detecting the presence of a variant by comparing the expected sequencing data for the first region to the generated sequencing data associated with the sequence of the first region.

Figure 13:
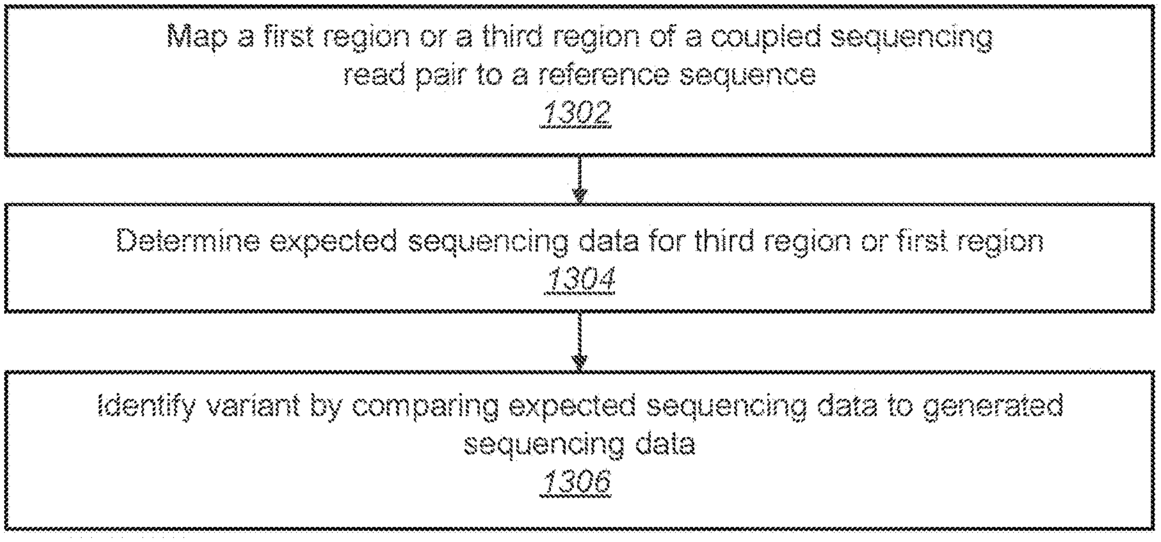
FIG. 13 illustrates an exemplary method of detecting a variant between two sequenced regions of a coupled sequencing read pair.

FIG. 13 illustrates an exemplary method of detecting a variant between two sequenced regions of a coupled sequencing read pair. At step 1302, a first region or portion thereof, or a third region or portion thereof, of a coupled sequencing read pair is mapped to a reference sequence. At step 1304, expected sequencing data for the third region or portion thereof, or the first region or portion thereof, is determined. At step 1306, the presence of a variant is detected by comparing the expected sequencing data for the first region or third region to generated sequencing data associated with the sequence of the first region or the third region. Exemplary variant detection methods are provided in the Examples.

The method of detecting a variant can use a reference sequence, which may or may not include a test variant. The test variant may be selected, for example, identifying the test variant within a second polynucleotide or from a biomarker panel. By way of example, the test variant may be used to determine a haplotype of polynucleotide. An allele or variant may be identified in a polynucleotide, and the method described herein can be used to determine whether the polynucleotide that gave rise to the coupled sequencing read pair is of the same haplotype or a different haplotype as the polynucleotide having the identified allele or variant. The detected test variant in the coupled sequencing read pair can be associated with an allele sequenced in the first region or the third region of the polynucleotide.

When detecting the presence of a test variant, the reference sequence can include a test variant, and the presence of the test variant within the subject's genome can be detected by comparing the expected test variant sequencing data for the third region or portion thereof to determined sequencing data for the third region or portion thereof. If the expected test variant sequencing data matches the determined sequencing data, then the test variant is detected within the reference sequence. For example, in some embodiments, a method of detecting a test variant between two sequenced regions of a coupled sequencing read pair (with the primer having been extended through the first region using nucleotides provided in a first region flow order and/or the primer having been extended through the third region using nucleotides provided in a third region flow order) includes mapping the first region or a portion thereof to a reference sequence that includes the test variant. Test variant expected reference sequencing data for the other region or portion thereof (i.e., if the first region or portion is mapped, the other region refers to the third region or portion thereof) is then determined. The test variant expected sequencing data can be determined, for example, using a reference sequence that includes the test variant for the second region, the second region flow order, the reference sequence for the other region or portion thereof, and the flow order for the other region or portion thereof. In another example, the expected sequencing data is determined using a reference sequence having the test variant for the second region, the second region flow order, a flow order for the other region, and sequencing data associated with the sequence of the other region (which may be the same sequencing data generated when generating the coupled sequencing read pair, or sequencing data generated by other means). The determined test variant expected sequencing data for the other region can be compared to generated sequencing data for the other region. A match between the expected and generated sequencing data indicates the presence of the test variant.

Detection of a Short Genetic Variant

The methods described herein may be used to detect a short genetic variant (e.g., a SNP or a short indel (less than 10 consecutive bases in length) within the second region (for example, when the primer is extended through the second region without detecting the presence or absence of a label of a nucleotide incorporated into the extending primer, or by including a mixture of at least two different types of nucleotide bases to extend the primer). A short genetic variant within the second region may be detected by analyzing the signal obtained when detecting the incorporation of nucleotides in a downstream (e.g., third) region. The short genetic variant can be, for example, a variant or mutation found within a subpopulation of individuals or a variant or mutation unique to a single or specific individual. The short genetic variants may be germline variants or somatic variants.

Sequencing data can be generated based on the detection of an incorporated nucleotide and the order of nucleotide introduction. Take, for example, the flowing extended sequences (i.e., each reverse complement of a corresponding template sequence): CTG, CAG, CCG, CGT, and CAT (assuming no preceding sequence or subsequent sequence subjected to the sequencing method), and a repeating flow cycle of T-A-C-G (that is, sequential addition of T, A, C, and G nucleotides in repeating cycles). A particular type of nucleotides at a given flow position would be incorporated into the primer only if a complementary base is present in the template polynucleotide). An exemplary resulting flowgram is shown in Table 5, where 1 indicates incorporation of an introduced nucleotide and 0 indicates no incorporation of an introduced nucleotide. The flowgram can be used to derive the sequence of the template strand. For example, the sequencing data (e.g., flowgram) discussed represents the sequence of the extended primer strand, and the reverse complement of which can readily be determined to represent the sequence of the template strand. An asterisk (*) in Table 5 indicates that a signal may be present in the sequencing data if additional nucleotides are incorporated in the extended sequencing strand (e.g., a longer template strand).

TABLE 5

| | Cycle 1 | | | | Cycle 2 | | | | Cycle 3 | | | |
|---|---|---|---|---|---|---|---|---|---|---|---|---|
| Flow Position | 1 | 2 | 3 | 4 | 5 | 6 | 7 | 8 | 9 | 10 | 11 | 12 |
| Base in Flow | T | A | C | G | T | A | C | G | T | A | C | G |
| Extended sequence: CTG | 0 | 0 | 1 | 0 | 1 | 0 | 0 | 1 | * | * | * | * |
| Extended sequence: CAG | 0 | 0 | 1 | 0 | 0 | 1 | 0 | 1 | * | * | * | * |
| Extended sequence: CCG | 0 | 0 | 2 | 1 | * | * | * | * | * | * | * | * |
| Extended sequence: CGT | 0 | 0 | 1 | 1 | 1 | * | * | * | * | * | * | * |
| Extended sequence: CAT | 0 | 0 | 1 | 0 | 0 | 1 | 0 | 0 | 1 | * | * | * |

The flowgram may be binary or non-binary. A binary flowgram detects the presence (1) or absence (0) of an incorporated nucleotide. A non-binary flowgram can more quantitatively determine a number of incorporated nucleotides from each stepwise introduction. For example, an extended sequence of CCG would include incorporation of two C bases in the extending primer within the same C flow (e.g., at flow position 3), and signals emitted by the labeled base would have an intensity greater than an intensity level corresponding to a single base incorporation. This is shown in Table 5. The non-binary flowgram also indicates the presence or absence of the base, and can provide additional information including the number of likely bases incorporated into each extending at the given flow position. The values do not need to be integers. In some cases, the values can be reflective of uncertainty and/or probabilities of a number of bases being incorporated at a given flow position.

In some embodiments, the sequencing data set includes flow signals representing a base count indicative of the number of bases in the sequenced nucleic acid molecule that are incorporated at each flow position. For example, as shown in Table 5, the primer extended with a CTG sequence using a T-A-C-G flow cycle order has a value of 1 at position 3, indicating a base count of 1 at that position (the 1 base being C, which is complementary to a G in the sequenced template strand). Also in Table 5, the primer extended with a CCG sequence using the T-A-C-G flow cycle order has a value of 2 at position 3, indicating a base count of 2 at that position for the extending primer during this flow position. Here, the 2 bases refer to the C-C sequence at the start of the CCG sequence in the extending primer sequence, and which is complementary to a G-G sequence in the template strand.

The flow signals in the sequencing data set may include one or more statistical parameters indicative of a likelihood or confidence interval for one or more base counts at each flow position. In some embodiments, the flow signal is determined from an analog signal that is detected during the sequencing process, such as a fluorescent signal of the one or more bases incorporated into the sequencing primer during sequencing. In some cases, the analog signal can be processed to generate the statistical parameter. For example, a machine learning algorithm can be used to correct for context effects of the analog sequencing signal as described in published International patent application WO 2019084158 A1, which is incorporated by reference herein in its entirety. Although an integer number of zero or more bases are incorporated at any given flow position, a given analog signal many not perfectly match with the analog signal. Therefore, given the detected signal, a statistical parameter indicative of the likelihood of a number of bases incorporated at the flow position can be determined. Solely by way of example, for the CCG sequence in Table 5, the likelihood that the flow signal indicates 2 bases incorporated at flow position 3 may be 0.999, and the likelihood that the flow signal indicates 1 base incorporated at flow position 3 may be 0.001. The sequencing data set may be formatted as a sparse matrix, with a flow signal including a statistical parameter indicative of a likelihood for a plurality of base counts at each flow position. Solely by way of example, a primer extended with a sequence of TATGGTCGTCGA (SEQ ID NO: 15) using a repeating flow-cycle order of T-A-C-G may result in a sequencing data set shown in FIG. 14A. The statistical parameter or likelihood values may vary, for example, based on the noise or other artifacts present during detection of the analog signal during sequencing. In some embodiments, if the statistical parameter or likelihood is below a predetermined threshold, the parameter may be set to a predetermined non-zero value that is substantially zero (i.e., some very small value or negligible value) to aid the statistical analysis further discussed herein, wherein a true zero value may give rise to a computational error or insufficiently differentiate between levels of unlikelihood, e.g. very unlikely (0.0001) and inconceivable (0).

A value indicative of the likelihood of the sequencing data set for a given sequence can be determined from the sequencing data set without a sequence alignment. For example the most likely sequence, given the data, can be determined by selecting the base count with the highest likelihood at each flow position, as shown by the stars in FIG. 14B (using the same data shown in FIG. 14A). Thus, the sequence of the primer extension can be determined according to the most likely base count at each flow position: TATGGTCGTCGA (SEQ ID NO: 15). From this, the reverse complement (i.e., the template strand) can be readily determined. Further, the likelihood of this sequencing data set, given the TATGGTCGTCGA (SEQ ID NO: 15) sequence (or the reverse complement), can be determined as the product of the selected likelihood at each flow position.

The sequencing data set associated with a nucleic acid molecule can be compared to one or more (e.g., 2, 3, 4, 5, 6 or more) possible candidate sequences. A close match (based on match score, as discussed below) between the sequencing data set and a candidate sequence indicates that it is likely the sequencing data set arose from a nucleic acid molecule having the same sequence as the closely matched candidate sequence. In some embodiments, the sequence of the sequenced nucleic acid molecule may be mapped to a reference sequence (for example using a Burrows-Wheeler Alignment (BWA) algorithm or other suitable alignment algorithm) to determine a locus (or one or more loci) for the sequence. As discussed above, the sequencing data set in flowspace can be readily converted to basespace (or vice versa, if the flow order is known), and the mapping may be done in flowspace or basespace. The locus (or loci) corresponding with the mapped sequence can be associated with one or more variant sequences, which can operate as the candidate sequences (or haplotype sequences) for the analytical methods described herein. One advantage of the methods described herein is that the sequence of the sequenced nucleic acid molecule does not need to be aligned with each candidate sequence using an alignment algorithm in some cases, which is generally computationally expensive. Instead, a match score can be determined for each of the candidate sequences using the sequencing data in flow-space, a more computationally efficient operation.

A match score indicates how well the sequencing data set supports a candidate sequence. For example, a match score indicative of a likelihood that the sequencing data set matches a candidate sequence can be determined by selecting a statistical parameter (e.g., likelihood) at each flow position that corresponds with the base count that flow position, given the expected sequencing data for the candidate sequence. The product of the selected statistical parameter can provide the match score. For example, assume the sequencing data set shown in FIG. 14A for an extended primer, and a candidate primer extension sequence of TATGGTCATCGA (SEQ ID NO: 16). FIG. 14C (showing the same sequencing data set in FIG. 14A) shows a trace for the candidate sequence (solid circles). As a comparison, the trace for the TATGGTCGTCGA (SEQ ID NO: 15) sequence (see FIG. 14B) is shown in FIG. 14C using open circles. The match score indicative of the likelihood that the sequencing data matches a first candidate sequence TATGGTCATCGA (SEQ ID NO: 16) is substantially different from the match score indicative of the likelihood that the sequencing data matches a second candidate sequence TATGGTCGTCGA (SEQ ID NO: 15), even though the sequences vary only by a single base variation. As seen in FIG. 14C, the differences between the traces is observed at flow position 12, and propagates for at least 9 flow positions (and potentially longer if the sequencing data extended across additional flow positions). This continued propagation across one or more flow cycles may be referred to as a "flow shift" or a "cycle shift," and is generally a very unlikely event if the sequencing data set matches the candidate sequence.

A match score between each sequencing data set and candidate sequences (or each candidate sequence) can then be determined. For example, a likelihood that a sequencing data set matches a give candidate sequence $L(R_i|H_i)$ can be determined using (for example, product of) the likelihood of the selected base count at each flow position for the given candidate sequence.

The match score can be used to classify the test sequencing data and/or the nucleic acid molecule associated with the test sequencing data. The classifier can indicate that the nucleic acid molecule includes the variant (e.g., the variant included in the candidate sequence), that the nucleic acid molecule does not include the variant, or can indicate a null call. A null call neither indicates the presence or absence of the variant in the nucleic acid molecule associated with the test sequencing data, but instead indicates that the match score cannot be used to make a call with the desired statistical confidence. The test sequencing data or nucleic acid molecule may be classified as having the variant, for example, if the match score is above a desired confidence threshold. Conversely, the test sequencing data or nucleic acid molecule may be classified as not having the variant, for example, if the match score is below a desired confidence threshold.

The above analysis may be applied to select a candidate sequence from two or more different candidate sequences. The match score indicative of a likelihood that the sequencing data set matches each candidate sequence can be determined. For example, the statistical parameter at each flow position in the sequencing data set that corresponds with a base count of the candidate sequence at that flow position can be selected for each candidate sequence. In some embodiments, this analysis includes generating expected sequencing data for the candidate sequencing assuming the candidate sequence is sequenced using the same flow order used to generate the sequencing data set for the sequenced test nucleic acid molecule. This may be generated by sequencing a nucleic acid molecule with the candidate sequence, or by generating the candidate sequencing data set in silico based on the candidate sequence and the flow order. Exemplary candidate sequencing data sets are shown below the test data sequencing data set in FIG. 14C, with the first candidate sequence (TATGGTCATCGA (SEQ ID NO: 16)) corresponding to the solid circles trace and the second candidate sequence (TATGGTCGTCGA (SEQ ID NO: 15)) corresponding to the open circle trace. In some embodiments, for example, if a match score is determined for two or more different candidate sequences, the test sequencing data or the nucleic acid molecule may be classified as having the variant of one of the two or more candidate sequences, not having the variant of one of the two or more candidate sequence, or a null call may be made between the two or more candidate sequences (for example, if a call cannot be made for any of the candidate sequences or if the match score indicates two or more different variants at the same locus).

Once the match score for the sequencing data set is determined for the candidate sequences, the candidate sequence having the short genetic variant can be selected based on the match score (for example, the candidate sequence that results in a match score with the highest likelihood match from among the two or more candidate sequences). The sequencing data arising from the sequence nucleic acid molecule having the short genetic variant will match the candidate sequence having the short genetic variant, and that candidate sequence can be selected, while the rejected (or non-selected) candidate sequence(s) do not include the short genetic variant as indicated by the less likelihood match (based on the determined match scores for those candidate sequences). The non-selected candidate sequence may differ from the selected candidate sequence (which best matches the sequenced nucleic acid molecule sequencing data set) at two or more flow positions, which may be two or more consecutive flow positions or two or more non-consecutive flow positions. In some embodiments, the non-selected candidate sequence differs from the selected candidate sequence at 3 or more, 4 or more, 5 or more, 6 or more, 7 or more, 8 or more, 9 or more, or 10 or more flow positions. In some embodiments, non-selected candidate sequence differs from the selected candidate sequence across 1 or more, 2 or more, 3 or more, 4 or more, or 5 or more flow cycles. In some embodiments, the non-selected candidate sequence differs from the selected candidate sequence at X base positions, wherein the sequencing data set associated with the sequence nucleic acid molecule differs from the non-selected candidate sequence at (X+2) or more flow positions. An increase in the number of different flow positions between the selected and the non-selected candidate sequence, wherein the sequenced nucleic acid molecule sequencing data set best matches the selected candidate sequence, lowers the likelihood that the sequenced nucleic acid molecule sequencing data set resulted from sequencing a nucleic acid molecule with the non-selected candidate sequence.

The likelihood that the sequencing data set for a sequenced nucleic acid molecule matches a non-selected candidate sequence is preferably low, such as less than 0.05, less than 0.04, less than 0.03, less than 0.02, less than 0.01, less than 0.005, less than 0.001, less than 0.0005, or less than 0.0001. The likelihood that the sequencing data set for a sequenced nucleic acid molecule matches a selected candidate sequence is preferably high, such as greater than 0.95, greater than 0.96, greater than 0.97, greater than 0.98, greater than 0.99, greater than 0.995, or greater than 0.999.

The method for detecting a short genetic variant in a test sample may, in some embodiments, include analyzing a plurality of test sequencing data sets, with each test sequencing data set being associated with a separate test nucleic acid molecule in the test sample. The nucleic acid molecules at least partially overlap at a locus, for example if the sequences of the nucleic acid molecules were aligned to a reference sequence. At least a portion of the nucleic acid molecules may have different sequencing start positions (with respect to a locus), which results in different flow positions for a given base within the sequence and/or a different flow order context. In this manner, the same candidate sequences can be used to analyze the test sequencing data sets in the plurality. For each candidate sequence, a match score indicative of a likelihood that the plurality of test sequencing data sets matches the candidate sequence can be determined, and the candidate sequence having the highest likelihood match (and thus, including the short genetic variant) can be selected. An exemplary analysis for detecting a short genetic variant using a plurality of test sequencing data sets is shown in FIGS. 15A-15D. In FIG. 15A, the sequence corresponding to three sequenced test nucleic acid molecules (R1, R2, and R3, each represented by the sequence of the extended primer) are aligned to a reference sequence at an overlapping locus associated with two candidate sequences (H1 and H2). FIG. 15B, FIG. 15C, and FIG. 15D show exemplary sequencing data sets for R1, R2, and R3, respectively, along with the selected statistical parameter at each flow position in the sequencing data set that corresponds with a base of H1 (closed circle) or H2 (open circle).

The presence (or identity) or absence of a short genetic variant can be called for the test sample using one or more determined match scores. In some embodiments, for example, a single nucleic acid molecule (or associated test sequencing data set) classified as having the variant may be sufficient to call the presence, identity, or absence of the variant, for example if the match score indicates a match with the candidate sequence with a desired or pre-set confidence. In some embodiments, an predetermined number (e.g., 1 or more, 2 or more, 3 or more, 4 or more, 5 or more, etc.) of nucleic acid molecules (or test sequencing data sets associated with nucleic acid molecules) are classified as having the variant before the variant is called for the test sample. In some embodiments, the number of nucleic acid molecules (or test sequencing data sets associated with nucleic acid molecules) is dynamically selected depending on the match scores; for example, a single nucleic acid molecule classified as having the variant with a high confidence match score may be used to call the variant, or two or more nucleic acid molecules classified as having the variant with lower confidence match scores may be used to call the variant.

Optionally, the separate match scores for sequencing data sets are collectively analyzed to determine a match score for the plurality of test sequencing data sets. For example, once the match score for each test sequencing data set for each candidate sequence is determined using the methods described herein, the match score indicative of a likelihood that the plurality of test sequencing data sets matches the candidate sequences can be determined using known Bayesian methods, for example using the HaplotypeCaller algorithm included in the Genome Analysis Toolkit (GATK), and the candidate sequence with the highest likelihood match can be selected. See, e.g., DePristo et al., *A framework for variation discovery and genotyping using next-generation DNA sequencing data*, Nature Genetics 43, 491-498 (2011); and Poplin et al., *Scaling accurate genetic variant discovery to tens of thousands of samples*, bioRxiv, www.biorxiv.org/content/10.1101/201178v3 (Jul. 24, 2018); Hwang et al., *Systematic comparison of variant calling pipelines using gold standard personal exome variants*, Scientific Reports, vol. 5, no. 17875 (2015); the contents of each of which are incorporated herein.

Hypothetical Example 1—SNP detection. A hypothetical nucleic acid molecule is sequenced using non-terminating nucleotides provided in separate nucleotide flows according to a flow-cycle order A-T-G-C, resulting in the test sequencing data set shown in FIG. 14A. Each value of in the sequencing data set indicates the likelihood that the indicated base count at each flow position is correct. Based on the sequencing data set, a preliminary sequence is determined as TATGGTCGTCGA (SEQ ID NO: 15), which is mapped to a locus of reference genome. The locus of the reference genome is associated with potential haplotype sequences TATGGTCGTCGA (SEQ ID NO: 15) (H1) and TATGGTCATCGA (SEQ ID NO: 16) (H2). A likelihood value associated with the base count of the haplotype sequence for each flow position is selected, for each haplotype. The likelihood of the sequencing data set given each haplotype is determined by multiplying the likelihood value associated with the base count of the haplotype sequence for each flow position. The log likelihood of the sequencing data set if H1 is the correct sequence is −0.015, and the log likelihood of the sequencing data set if H2 is the correct sequence is −27.008. Thus, the sequence of H1 is selected for this nucleic acid molecule.

Hypothetical Example 2—Indel detection. A hypothetical nucleic acid molecule is sequenced using non-terminating nucleotides provided in separate nucleotide flows according to a flow-cycle order A-T-G-C, resulting in the test sequencing data set shown in FIG. 16. Each value of in the sequencing data set indicates the likelihood that the indicated base count at each flow position is correct. Based on the sequencing data set (i.e., by selecting the most likely base count at each flow position), a preliminary sequence is determined as TATGGTCGATCG (SEQ ID NO: 22), which is mapped to a locus of reference genome. The locus of the reference genome is associated with potential haplotype sequences TATGGTCGTCGA (SEQ ID NO: 21) (H1) and TATGGTCGATCG (SEQ ID NO: 22) (H2). A likelihood value associated with the base count of the haplotype sequence for each flow position is selected, for each haplotype. The likelihood of the sequencing data set given each haplotype is determined by multiplying the likelihood value associated with the base count of the haplotype sequence for each flow position. The log likelihood of the sequencing data set if H1 is the correct sequence is −24.009, and the log likelihood of the sequencing data set if H2 is the correct sequence is −0.015. Thus, the sequence of H2 is selected for this nucleic acid molecule.

When the signal difference due to a variant in the second (i.e., "dark") region propagates into the third region (i.e., a region where incorporation of nucleotides is detected), the flow shift that results from the variant in the second region can be detected in the third region. In the hypothetical examples discussed above, for example, Cycle 3 could be considered the "dark" or second region (which may be any number of cycles), and Cycle 4 and Cycle 5 could be the third region (which may also be any number of cycles).

Detection of a Transversion

A transversion is a SNP that swaps a purine for a pyrimidine or vice versa. The method described herein can be implemented to be particularly sensitive for the detection of transversions within the second region of the coupled sequencing read pair. For example, primer extension through the second region using a second region flow order comprising alternating nucleotide pairs of pyrimidines (C+T) with the purines (A+G) would be highly sensitive to transversions.

For example, a coupled sequencing read pair for detecting the presence of a base transversion in a polynucleotide can be generated by (a) hybridizing the polynucleotide to a primer to form a hybridized template; (b) generating sequencing data associated with a sequence of a first region of the polynucleotide by extending the primer using labeled nucleotides, and detecting the presence or absence of an incorporated labeled nucleotide; (c) further extending the primer extended in step (b) through a second region using a flow order comprising alternating nucleotide pairs of (1) cytosine and thymine, and (2) adenine and guanine; and (d) generating sequencing data associated with a sequence of a third region of the polynucleotide by further extending the primer extended in step (c) using labeled nucleotides, and detecting the presence or absence of an incorporated labeled nucleotide. Transversion can be detected in the second region even without detecting the presence or absence of a label of a nucleotide incorporated into the primer extended through the second region.

The coupled sequencing read pair generated for transversion detection can be used to detect the transversion by mapping a first region or portion thereof (or a third region or a portion thereof) of the coupled sequencing read pair; determining expected sequencing data for the third region or portion thereof (or the first region or portion thereof) using the second region flow order, the third region flow order, and the reference sequence; and detecting the presence of the base transversion based on the difference between expected reference sequencing data for the third region and the generated sequencing data for the third region.

The expected reference sequencing data for the third region or portion thereof (or first region or portion thereof) may be determined by, for example, using the second region flow order, the third region flow order, the reference sequence for the second region, and the reference sequence for the third region. In some embodiments, the expected reference sequencing data for the third region is determined using the second region flow order, the third region flow order, the reference sequence for the second region, and generated sequence data associated with the sequence of the third region, wherein the generated sequence data associated with the sequence of the third region is the same or different sequence data generated when generated the coupled sequencing read pair.

Variant Validation

A plurality of at least partially overlapping coupled sequencing reads can be used to validate a variant status. As sequencing errors may occasionally occur during the normal course of nucleotide incorporation into an extending primer (for example, due to polymerase error or read error), variant validation can be helpful to minimize reporting false positive or false negatives. Additionally, the sensitivity of the method described herein may vary depending on the context of the variant and flow order used when extending the primer through the second region. Therefore, to minimize false positive or false negative errors, coupled sequencing read pairs that overlap or at least partially overlap can be compared to validate the variant. The plurality of coupled sequencing read pairs that are used to validate the variant can include different start points (e.g., different first region start points, different second region start points, and/or different third region start point) or may be generated using different second region flow orders.

A test variant of interest can be selected, and a plurality of overlapping coupled sequencing read pairs are analyzed to determine the status of the test variant (e.g., whether the variant is present or absent) within the coupled sequencing read pairs. The overlapping coupled sequencing read pairs include a locus corresponding to a locus of the test variant. In some embodiments, the test variant is within the first region of at least a portion of the coupled sequencing read pairs. In some embodiments, the test variant is within the second region of at least a portion of the coupled sequencing read pairs. In some embodiments, the test variant is within the third region of at least a portion of the coupled sequencing read pairs.

A tolerance threshold can be selected to make the call as to whether the test variant is present or absent at the locus. If more couple sequencing read pairs in the plurality positively identify the test variant than a predetermined threshold identify the test variant, for example, the test variant is positively called. The threshold may be set as desired by a risk tolerance. For example, the tolerance threshold may be 60% or more, 70% or more, 80% or more, 90% or more, or 95% or more of the coupled sequencing read pairs identifying the test variant.

Figure 17:
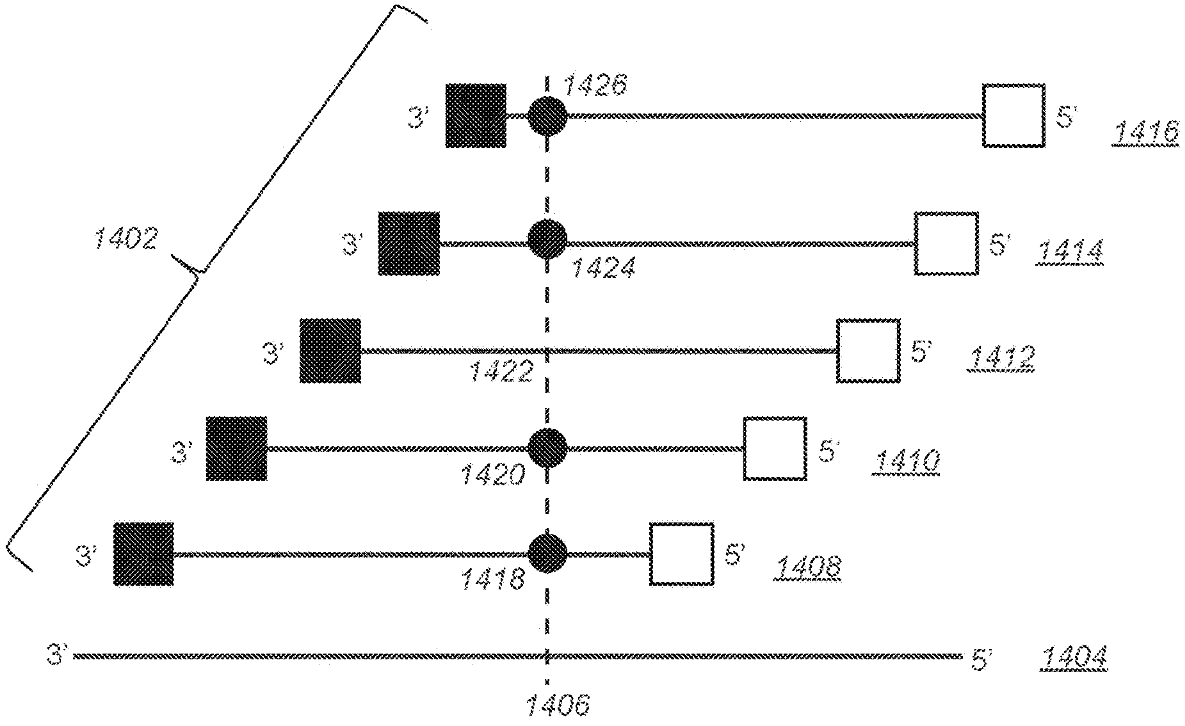
FIG. 17 illustrates an exemplary schematic for comparing coupled sequencing read pairs to determine the status of a test variant.

FIG. 17 illustrates an exemplary schematic for comparing coupled sequencing read pairs to determine the status of a test variant. A plurality of overlapping coupled sequencing read pairs 1402 are aligned to reference sequence 1404. At locus 1406, four of the five overlapping coupled sequencing read pairs allowed for the identification of the variant, which was not identified in one of the coupled sequencing read pairs. Specifically, coupled sequencing read pairs 1408, 1410, 1414, and 1416 include the identified variant at loci 1418, 1420, 1424, and 1426, respectively. The locus of the variant at each coupled sequencing read pair aligns with the reference sequence 1404 at locus 1406. Coupled sequencing read pair 1412 did not identify the variant at locus 1422 (for example, due to a sequencing read error or because of the context of the variant with the second region and the flow order used to generate coupled sequencing read pair 1412.

Construction or Validation of a Consensus Sequence

Coupled sequencing read pairs generated according to the methods described herein may be used to generate one or more consensus sequences by assembling the couple sequencing read pairs. Paired-end sequencing has been previously used to assemble a consensus sequence, but the limited information available for the region between the sequenced ends of the polynucleotides results in a lower quality consensus sequence with frequent mis-aligned sequences. See, for example, and Zerbino et al., *Velvet: Algorithms for de novo short read assembly using de Bruinn graphs*, Genome Research, vol. 18, pp. 821-820 (2008), incorporated herein by reference for all purposes. The methods described herein allow for substantially more information to be extracted from the unsequenced second region between the sequenced first and third regions. This additional information allows for a more robust and accurate consensus sequence.

The coupled sequencing read pairs can be used to validate one or more consensus sequences or a portion of one or more consensus sequences. Consensus sequence assembly may result in multiple possible sequence assemblies given the available data, and it can be challenging to select which of these possible sequences is the correct consensus sequence using traditional paired-end sequencing data. Because additional information can be extracted from the second region of the coupled sequencing read pairs, consensus sequence validation is more robust using the methods described herein. To validate the consensus sequence, the first region or a portion thereof (or the third region or portion thereof) can be mapped to a selected consensus sequence. Expected sequencing data for the other region or portion thereof (i.e., the third region or portion thereof if the first region or portion thereof is mapped, or the first region or portion thereof if the third region or portion thereof is mapped). The expected sequencing data may be determined, for example, as described herein. In one example, the expected sequencing data is determined using the second region flow order, the selected consensus sequence, and the first region flow order (if the expected sequencing data is for the first region or portion thereof) or the third region flow order (if the expected sequencing data is for the third region or portion thereof). The expected sequencing data can then be compared to the generated sequencing data for the coupled sequencing read pair at the corresponding region to validate the consensus sequence portion. Expected sequencing data matching the generated sequencing data indicates that the consensus sequence portion is correctly assembled. Expected sequencing data not matching the generated sequencing data indicates that the consensus sequence portion is incorrectly assembled.

In some embodiments, more than one consensus sequence is constructed or validated. For example, certain organisms are polyploid (healthy humans, for example, are diploid organisms and have two copies of each chromosome (except the sex chromosomes in male humans). A consensus sequences can be assembled corresponding to one or more chromosome copies (e.g., a consensus sequence may be assembled for each chromosome pair in a human sequence). The process of assigning a coupled sequencing read pair to the corresponding chromosome of a polyploidal organism may be referred to as haplotyping. The methods described herein can be used to improve the accuracy or efficiency of haplotyping. For example, the test variant can be associated with a first chromosome or a second chromosome (or other additional chromosome from the polyploid organism) using information from the second region of the coupled sequencing read pairs described herein.

Systems, Devices, and Reports

The operations described above, including those described with reference to FIGS. 1-17, are optionally implemented by components depicted in FIG. 18. It would be clear to a person of ordinary skill in the art how other processes, for example, combinations or sub-combinations of all or part of the operations described above, may be implemented based on the components depicted in FIG. 18. It would also be clear to a person having ordinary skill in the art how the methods, techniques, systems, and devices described herein may be combined with one another, in whole or in part, whether or not those methods, techniques, systems, and/or devices are implemented by and/or provided by the components depicted in FIG. 18.

Figure 18:
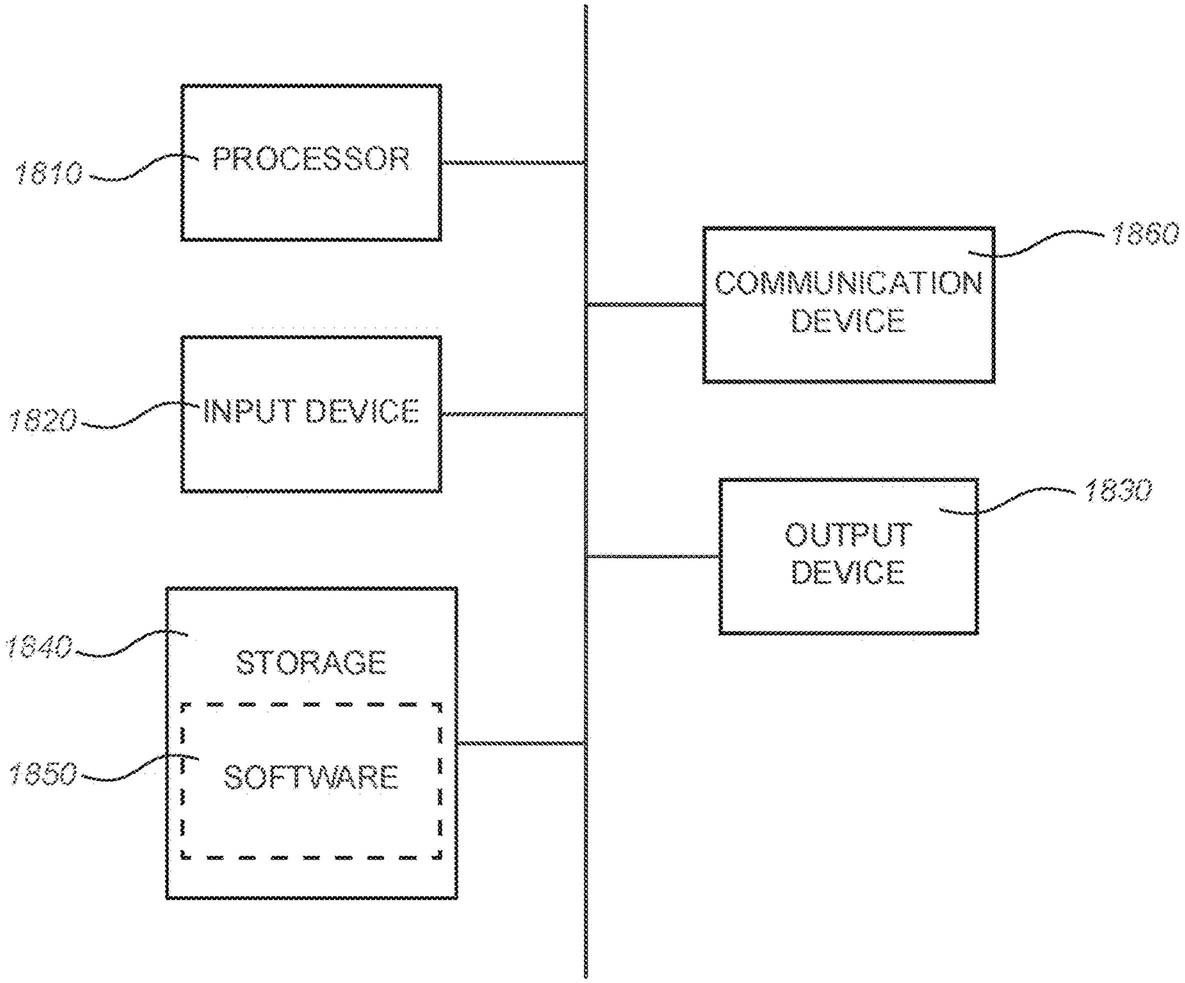
FIG. 18 illustrates an example of a computing device in accordance with one embodiment, which may be used to implement a method as described herein.

FIG. 18 illustrates an example of a computing device in accordance with one embodiment. Device 1800 can be a host computer connected to a network. Device 1800 can be a client computer or a server. As shown in FIG. 18, device 1800 can be any suitable type of microprocessor-based device, such as a personal computer, workstation, server, or handheld computing device (portable electronic device) such as a phone or tablet. The device can include, for example, one or more of processor 1810, input device 1820, output device 1830, storage 1840, and communication device 1860. Input device 1820 and output device 1830 can generally correspond to those described above, and can either be connectable or integrated with the computer.

Input device 1820 can be any suitable device that provides input, such as a touch screen, keyboard or keypad, mouse, or voice-recognition device. Output device 1830 can be any suitable device that provides output, such as a touch screen, haptics device, or speaker.

Storage 1840 can be any suitable device that provides storage, such as an electrical, magnetic or optical memory including a RAM, cache, hard drive, or removable storage disk. Communication device 1860 can include any suitable device capable of transmitting and receiving signals over a network, such as a network interface chip or device. The components of the computer can be connected in any suitable manner, such as via a physical bus or wirelessly.

Software 1850, which can be stored in storage 1840 and executed by processor 1810, can include, for example, the programming that embodies the functionality of the present disclosure (e.g., as embodied in the devices as described above).

Software 1850 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1840, that can contain or store programming for use by or in connection with an instruction execution system, apparatus, or device.

Software 1850 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 1800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1800 can implement any operating system suitable for operating on the network. Software 1850 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

The methods described herein optionally further include reporting information determined using the analytical methods and/or generating a report containing the information determined suing the analytical methods. For example, in some embodiments, the method further includes reporting or generating a report containing related to the identification of a variant in a polynucleotide derived from a subject (e.g., within a subject's genome). Reported information or information within the report may be associated with, for example, a locus of a coupled sequencing read pair mapped to a reference sequence, a detected variant (such as a detected structural variant or detected SNP), one or more assembled consensus sequences and/or the validation statistic for the one or more assembled consensus sequences. The report may be distributed to or the information may be reported to a recipient, for example a clinician, the subject, or a researcher.

EXEMPLARY EMBODIMENTS

The following embodiments are exemplary and are not intended to limit the scope of the claimed invention.

Embodiment 1. A method of sequencing a polynucleotide, comprising: hybridizing the polynucleotide to a primer to form a hybridized template; generating sequencing data associated with a sequence of a first region of the polynucleotide by extending the primer through the first region of the polynucleotide using labeled nucleotides provided according to a first region flow order comprising a plurality of flow steps, and detecting the presence or absence of an incorporated labeled nucleotide after each flow step; extending the primer through a second region of the polynucleotide using labeled nucleotides provided according to a second region flow order comprising two or more flow steps; measuring a signal from the labeled nucleotides incorporated into the primer after the two or more flow steps of the second region flow order; and determining distance information indicative of the length of the second region using the measured signal.

Embodiment 2. The method of embodiment 1, wherein at least a portion of the two or more flow steps in the second region flow order comprises the simultaneous use of two or more different nucleotide bases.

Embodiment 3. The method of embodiment 1, wherein at least a portion of the two or more flow steps in the second region flow order comprises the simultaneous use of three or more different nucleotide bases.

Embodiment 4. The method of any one of embodiments 1-3, wherein the primer is extended through the second region without detecting incorporated labeled nucleotides after each flow step in the second region flow order.

Embodiment 5. The method of any one of embodiments 1-4, wherein the labeled nucleotides provided according to the second region flow order comprise a label that is not cleaved after each flow step in the second region flow order.

Embodiment 6. The method of any one of embodiments 1-5, comprising measuring a plurality of signals, wherein a signal is measured from labeled nucleotides incorporated into the primer after the every two to five flow steps in the second region flow order; and determining the distance information using the plurality of signals.

Embodiment 7. The method of embodiment 6, wherein the labeled nucleotides provided according to the second region flow comprise a label that is cleaved after measuring the signal after every two to five flow steps in the second region flow order.

Embodiment 8. The method of any one of embodiments 1-7, wherein nucleotides provided according to the second region flow order comprise unlabeled nucleotides and labeled nucleotides.

Embodiment 9. The method of any one of embodiments 1-7, wherein a first portion of the two or more flow steps in the second region flow order comprise the use of only unlabeled nucleotides and a second portion of the two or more flow steps of the second region flow order comprise the use of labeled nucleotides.

Embodiment 10. The method of embodiment 9, wherein the second portion of the flow steps in the second region flow order comprise the simultaneous use of labeled nucleotides and unlabeled nucleotides.

Embodiment 11. The method of any one of embodiments 1-7, wherein each of the two or more flow steps in the second region flow order comprises the simultaneous use of labeled and unlabeled nucleotides.

Embodiment 12. A method of sequencing a polynucleotide, comprising: hybridizing the polynucleotide to a primer to form a hybridized template; generating sequencing data associated with a sequence of a first region of the polynucleotide by extending the primer through the first region of the polynucleotide using labeled nucleotides provided according to a first region flow order comprising a plurality of flow steps, and detecting the presence or absence of an incorporated labeled nucleotide after each flow step; extending the primer through a second region of the polynucleotide using labeled nucleotides provided according to a second region flow order comprising a one or more flow steps, wherein at least one of the one or more flow steps comprises the simultaneous use of two or more different nucleotide bases; measuring a signal from labeled nucleotides incorporated into the primer after each of the one or more flow step in the second region flow order; and determining distance information indicative of a length of the second region using the measured signal or signals.

Embodiment 13. The method of embodiment 12, wherein each of the one or more flow steps in the second region flow order comprises the simultaneous use of two or more different nucleotide bases.

Embodiment 14. The method of embodiment 12 or 13, wherein at least one of the one or more flow steps in the second region flow order comprise the simultaneous use of three or more different nucleotide bases.

Embodiment 15. The method of embodiment 12 or 13, wherein at least one of the one or more flow steps in the second region flow order comprise the simultaneous use of four different nucleotide bases.

Embodiment 16. The method of any one of embodiments 12-15, wherein the labeled nucleotides provided according to the second region flow order comprise a label that is cleaved after measuring the signal after each flow step in the second region flow.

Embodiment 17. The method of any one of embodiments 12-16, wherein the one or more flow steps in the second region flow order comprise the simultaneous use of labeled nucleotides and unlabeled nucleotides.

Embodiment 18. The method of any one of embodiments 12-16, wherein each of the one or more flow steps in the second region flow order comprise the simultaneous use of labeled nucleotides and unlabeled nucleotides.

Embodiment 19. The method of any one of embodiments 1-18, wherein labeled nucleotides provided in the first region flow order are provided at a concentration less than a concentration of labeled nucleotides provided in the second region flow order.

Embodiment 20. The method of any one of embodiments 1-19, wherein the primer is extended through the first region before being extended through the second region.

Embodiment 21. The method of any one of embodiments 1-19, wherein the primer is extended through the second region prior to being extended through the first region.

Embodiment 22. The method of any one of embodiments 1-21, wherein the distance information is corrected for primers within a cluster comprising a plurality of copies of the polynucleotide that failed to extend with other primers within the cluster.

Embodiment 23. The method of any one of embodiments 1-22, wherein determining the distance information comprises determining a normalized signal per base incorporated into the primer, and determining a number of bases incorporated into the primer using the measured signal and the normalized signal per base.

Embodiment 24. The method of any one of embodiments 1-21, wherein the distance information indicative of the length of the second region is determined using a machine learning model.

Embodiment 25. The method of any one of embodiments 1-24, further comprising characterizing the polynucleotide as a duplicate of another polynucleotide or a unique polynucleotide using the distance information.

Embodiment 26. The method of any one of embodiments 1-25, further comprising generating sequencing data associated with a sequence of a third region of the polynucleotide by extending the primer through a third region using labeled nucleotides according to a third region flow order comprising a plurality of flow steps, and detecting the presence or absence of an incorporated labeled nucleotide after each flow step, wherein the second region is between the first region and the third region, thereby generating a coupled sequencing read pair.

Embodiment 27. The method of embodiment 26, further comprising associating the sequencing data of the first region with the sequencing data of the third region.

Embodiment 28. The method of embodiment 26 or 27, further comprising determining expected sequencing data for the second region using a reference sequence and the second region flow order.

Embodiment 29. The method of any one of embodiments 26-28, method further comprising determining expected sequencing data for the third region using a reference sequence for the second region, the second region flow order, a reference sequence for the third region, and the third region flow order.

Embodiment 30. The method of any one of embodiments 26-29, further comprising determining expected test variant sequencing data for the second region using the second region flow order and a second reference sequence for the second region, wherein the second reference sequence comprises the test variant.

Embodiment 31. The method of embodiment 30, further comprising determining expected test variant sequencing data for the third region using the second reference sequence for the second region, the second region flow order, a reference sequence for the third region, and the third region flow order.

Embodiment 32. A method of mapping a coupled sequencing read pair to a reference sequence, comprising: mapping a first region or portion thereof, or a third region or portion thereof, of a coupled sequencing read pair generated according to the method of any one of embodiments 26-31, to a reference sequence; and mapping the unmapped first region or portion thereof, or the unmapped third region or portion thereof, to the reference sequence using the determined distance information.

Embodiment 33. A method of detecting a structural variant, comprising: mapping a first region or portion thereof, or a third region or portion thereof, of a coupled sequencing read pair generated according to the method of any one of embodiments 26-31, to a reference sequence; determining an expected locus within a reference sequence for the unmapped first region or portion thereof, or the unmapped third region or portion thereof, using the determined distance information; determining expected sequencing data for a sequence at the expected locus based on the reference sequence; and detecting the structural variant by comparing the sequencing data of the unmapped first region or portion thereof, or the unmapped third region or portion thereof, to the expected sequencing data, wherein a difference between the sequencing data of the unmapped first region or portion thereof, or the unmapped third region or portion thereof, and the expected sequencing data indicates the structural variant.

Embodiment 34. A method of detecting a structural variant, comprising: mapping a first region or portion thereof and a third region or portion thereof, of a coupled sequencing read pair generated according to the method of any one of embodiments 26-31, to a reference sequence; determining a mapped distance information between the mapped first region and the mapped third region; and detecting the structural variant by comparing the mapped distance information to the determined distance information of the second region, wherein a difference between the mapped distance information and the determined distance information indicates the structural variant.

Embodiment 35. The method of embodiment 33 or 34, wherein the structural variant is a chromosomal fusion, an inversion, an insertion, or a deletion.

Embodiment 36. The method of embodiment 33 or 34, wherein the variant is an insertion or deletion within the second region.

Embodiment 37. A method of mapping a coupled sequencing read pair to a reference sequence, comprising: mapping a first region or portion thereof and a third region or portion thereof of a coupled sequencing read pair generated according to the method of any one of embodiments 26-31 to a reference sequence at two or more different position pairs comprising a first position and a second position; and selecting a correct position pair using the determined distance information.

Embodiment 38. A method for sequencing, comprising:

(a) providing a nucleic acid molecule comprising a first region and a second region;

(b) sequencing the first region by, in each flow step of a plurality of first flow cycles, incorporating a labeled nucleotide into a primer hybridized to the nucleic acid and detecting the labeled nucleotide, or detecting a lack of incorporation thereof into the primer; and (c) sequencing the second region by, (i) in each flow step of a plurality of second flow cycles, providing a plurality of nucleotides to the primer, (ii) subsequent to at least two or more flow steps of the plurality of second flow cycles, detecting one or more signals from one or more labeled nucleotides of the plurality of nucleotides incorporated into the primer, or detecting lack of incorporation thereof into the primer, and (iii) determining distance information indicative of a length of the second region based at least in part on the one or more signals.

Embodiment 39. The method of embodiment 38, wherein at least one of the at least two or more flow steps comprises a simultaneous use of two or more different nucleotide bases.

Embodiment 40. The method of embodiment 38, wherein at least one of the at least two or more flow steps comprises a simultaneous use of three or more different nucleotide bases.

Embodiment 41. The method of any one of embodiments 38-40, wherein, in (c), the primer is extended through the second region without detecting incorporated labeled nucleotides after each flow step in the plurality of second flow cycles.

Embodiment 42. The method of any one of embodiments 38-41, wherein a label of the one or more labeled nucleotides incorporated in (c) is not cleaved after each flow step in the plurality of second flow cycles.

Embodiment 43. The method of any one of embodiments 38-42, wherein (c) comprises measuring a plurality of signals, wherein a signal of the plurality of signals is measured after every two to five flow steps of the plurality of second flow cycles and determining the distance information based at least in part on the plurality of signals.

Embodiments 44. The method of embodiment 43, further comprising, subsequent to measuring the signal after the every two to five flow steps, cleaving one or more labels from labeled nucleotides incorporated in the primer.

Embodiment 45. The method of any one of embodiments 38-44, wherein the plurality of nucleotides comprises a mixture of unlabeled nucleotides and labeled nucleotides.

Embodiment 46. The method of any one of embodiments 38-44, wherein a first portion of the at least two or more flow steps comprises use of only unlabeled nucleotides and a second portion of the at least two or more flow steps comprises use of labeled nucleotides.

Embodiment 47. The method of embodiment 46, wherein the second portion of the at least two or more comprises a simultaneous use of labeled nucleotides and unlabeled nucleotides.

Embodiment 48. The method of any one of embodiments 38-44, wherein each of the at least two or more flow steps comprises a simultaneous use of labeled and unlabeled nucleotides.

Embodiment 49. A method for sequencing, comprising:

(a) providing a nucleic acid molecule comprising a first region and a second region;

(b) sequencing the first region by, in each flow step of a plurality of first flow cycles, incorporating a labeled nucleotide into a primer hybridized to the nucleic acid and detecting the labeled nucleotide, or detecting a lack of incorporation thereof into the primer; and (c) sequencing the second region by, (i) in each flow step of a plurality of second flow cycles, incorporating a labeled nucleotide into a primer hybridized to the nucleic acid and detecting one or more signals indicative of the labeled nucleotide, or detecting a lack of incorporation thereof into the primer, wherein at least one flow step of the plurality of second flow cycles comprises providing to the primer a plurality of nucleotides comprising two or more different bases, and (ii) determining distance information indicative of a length of the second region based at least in part on the one or more signals.

Embodiment 50. The method of embodiment 49, wherein the each flow step of the plurality of second flow cycles comprises a simultaneous use of two or more different nucleotide bases.

Embodiment 51. The method of embodiment 49 or 50, wherein the each flow step of the plurality of second flow cycles comprises a simultaneous use of three or more different nucleotide bases.

Embodiment 52. The method of any one of embodiments 49-51, wherein the each flow step of the plurality of second flow cycles comprises a simultaneous use of four different nucleotide bases.

Embodiment 53. The method of any one of embodiments 49-52, further comprising, in the each flow step of the plurality of second flow cycles, subsequent to detecting the one or more signals indicative of the labeled nucleotide, cleaving a label of the labeled nucleotide.

Embodiment 54. The method of any one of embodiments 49-53, wherein the plurality of second flow cycles comprises a simultaneous use of labeled nucleotides and unlabeled nucleotides.

Embodiment 55. The method of any one of embodiments 49-53, wherein the each flow step of the plurality of second flow cycles comprises a simultaneous use of labeled nucleotides and unlabeled nucleotides.

Embodiment 56. The method of any one of embodiments 38-55, wherein labeled nucleotides provided in the plurality of first flow cycles are provided at a concentration less than a concentration of labeled nucleotides provided in the plurality of second flow cycles.

Embodiment 57. The method of any one of embodiments 38-56, wherein the primer is extended through the first region before being extended through the second region.

Embodiment 58. The method of any one of embodiments 38-56, wherein the primer is extended through the second region prior to being extended through the first region.

Embodiment 59. The method of any one of embodiments 38-58, further comprising correcting the distance information by identifying primers within a cluster that comprise a plurality of copies of the nucleic acid molecule that failed to extend with other primers within the cluster.

Embodiment 60. The method of any one of embodiments 38-59, wherein determining the distance information comprises determining a normalized signal per base incorporated into the primer, and determining a number of bases incorporated into the primer using the one or more signals and the normalized signal per base.

Embodiment 61. The method of any one of embodiments 38-60, wherein the distance information is determined using a machine learning model.

Embodiment 62. The method of any one of embodiments 38-61, further comprising characterizing the polynucleotide as a duplicate of another polynucleotide or a unique polynucleotide using the distance information.

Embodiment 63. The method of any one of embodiments 38-62, further comprising sequencing a third region of the nucleic acid molecule by, in each flow step of a plurality of third flow cycles, incorporating a given labeled nucleotide into the primer and detecting the given labeled nucleotide, or detecting a lack of incorporation thereof into the primer, wherein the second region is between the first region and the third region, thereby generating a coupled sequencing read pair.

Embodiment 64. The method of embodiment 63, further comprising associating sequencing data of the first region with sequencing data of the third region.

Embodiment 65. The method of embodiment 63 or 64, further comprising determining expected sequencing data for the second region using a reference sequence and a second flow order of the plurality of second flow cycles.

Embodiment 66. The method of any one of embodiments 63-65, further comprising determining expected sequencing data for the third region using a reference sequence for the second region, the second flow order, a reference sequence for the third region, and a third flow order of the plurality of third flow cycles.

Embodiment 67. The method of any one of embodiments 63-66, further comprising determining expected test variant sequencing data for the second region using the second flow order and a second reference sequence for the second region, wherein the second reference sequence comprises a test variant.

Embodiment 68. The method of embodiment 67, further comprising determining expected test variant sequencing data for the third region using the second reference sequence for the second region, the second flow order, a reference sequence for the third region, and the third flow order.

EXAMPLES

The application may be better understood by reference to the following non-limiting examples, which is provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

Example 1

Figure 19A:
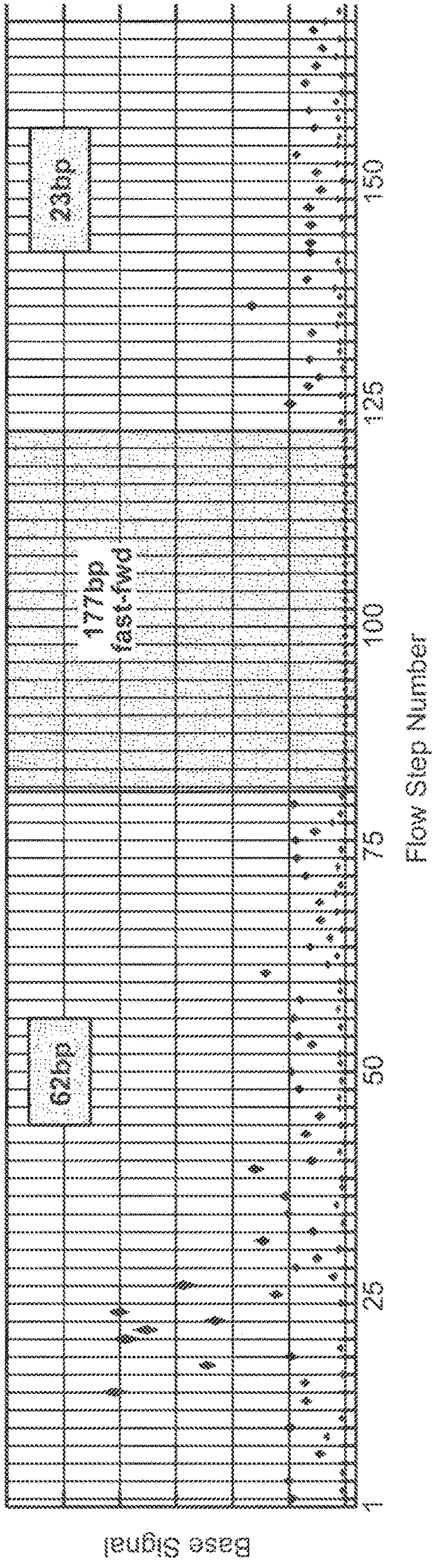
FIG. 19A show the signal coming from an incorporated base after each flow sequencing cycle in the first and third regions when extending a sequencing primer through a polynucleotide. Data was not collected within the second region because extension of the primer was accelerated through this region without detected base incorporation.

A nucleic acid construct having 262 bases was sequenced using a flow sequencing method that includes a fast-forward region, and again using a standard flow sequencing method (i.e., which does not include a fast forward region). A polynucleotide was ligated to an adapter sequence and tethered to a bead, which was amplified and associated with a sequencing surface. A sequencing primer was hybridized to a hybridization region within the adapter sequence, which allowed for the start of the flow sequencing method. In the first method, 62 bases were sequenced by extending the sequencing primer using alternating flows of a single type of fluorescently labeled, non-terminating nucleotide, and nucleotide incorporation after each step was determined using a fluorescence detector. The next 177 bases were exposed to alternating flows of un-labeled, non-terminating nucleotides where each flow has three of the four nucleotides present (i.e., "fast forward" mode) to allow the primer to be extended through the second region. Following extension of the primer through the "dark" (i.e., without detecting incorporated nucleotides) second region, another 23 bases were sequenced alternating flows of a single type of fluorescently labeled, non-terminating nucleotide, and nucleotide incorporation after each step was determined using a fluorescence detector. The results are shown in FIG. 19A, which shows the flow step number on the horizontal access and measure of sequencing signal (i.e., normalized fluorescence signal) in the vertical access. The method results in high-quality sequencing data following the fast forward regime.

Figure 19B:
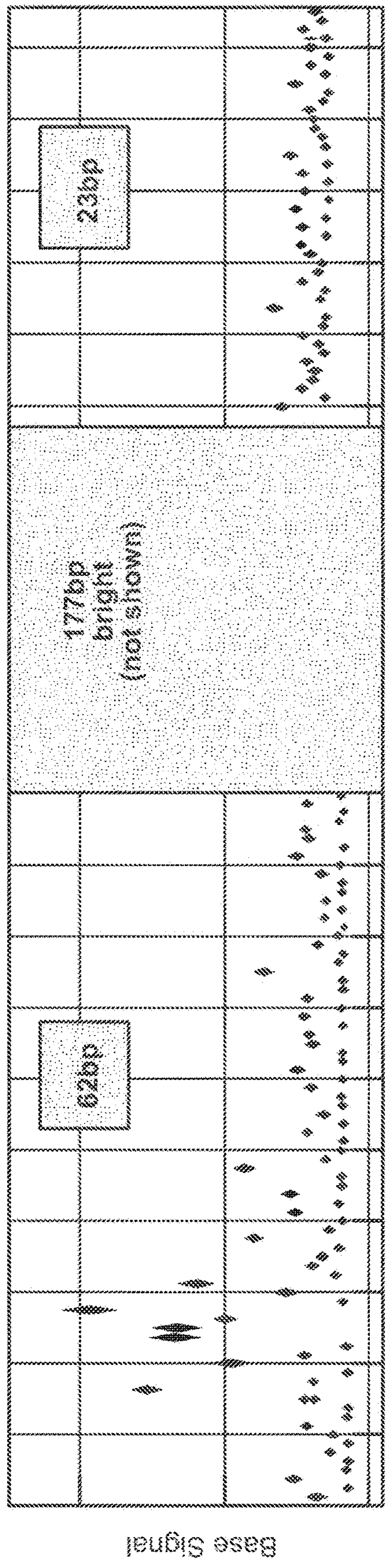
FIG. 19B show the signal coming from an incorporated base after each flow sequencing cycle in the first and third regions when extending a sequencing primer through a polynucleotide. Data was collected through the second region, but is not shown to condense the size of the figure.

The same 262 base construct was sequenced entirely in a standard flow sequencing method without an intervening fast forward regime. That is, the full 262 bases were sequenced alternating flows of a single type of fluorescently labeled, non-terminating nucleotide, and nucleotide incorporation after each step was determined using a fluorescence detector. Results are shown in FIG. 19B, which omits data from the corresponding 177 base region to compress the figure.

The sequencing construct advances more rapidly using the fast-forward flow sequencing method than the standard flow-sequencing method. The sequencing data from both ends of the polynucleotide can be associated to generate a coupled sequencing read pair and analyzed.

Example 2

Detection of a variant within SEQ ID NO: 4 (with a C→G single nucleotide polymorphism variant at base position 15 relative to reference sequence SEQ ID NO: 1) is described in this example. A coupled sequencing read pair can be generated for SEQ ID NO: 4 by hybridizing a primer to a hybridization sequence at the 5' end of SEQ ID NO: 4, and extending the primer using a flow sequencing method. In this example, 5 cycles are used, with Cycle 1 being used to extend the primer through the first region, Cycle 2 and Cycle 3 being used to extend the primer through the second region, and Cycle 4 and Cycle 5 being used to extend the primer through the third region. Cycle 1, Cycle 4, and Cycle 5 use labeled nucleotides to extend the primer, and the incorporation of a nucleotide into the primer is detected after each cycle step. In contrast, incorporation of a nucleotide into the primer may be skipped during Cycle 2 and Cycle 3. Each cycle has 4 steps, with Cycles 1, 4, and 5 include the sequential and independent addition of A-C-T-G labeled nucleotides, with a single base type being added at each cycle step, and incorporation of a labeled nucleotide being detected after each step. Cycle 2 and Cycle 3 are implemented in a “fast forward” mode, and include 4 cycle steps, wherein Step 1 omits A nucleotides (i.e., includes C, T, and G), Step 2 omits, C nucleotides (i.e., includes A, T, and G), Step 3 omits T nucleotides (i.e., includes A, C, and G), and Step 4 omits G nucleotides (i.e., includes A, C, and T). Nucleotide incorporation is not detected during the fast forward mode of Cycle 2 and Cycle 3. Because Cycles 2 and 3 include multiple different nucleotide base types simultaneously during primer extension, the primer is extended faster than if only a single base type was used at any given step. The flowgrams for SEQ ID NO: 1 (the reference sequence) and SEQ ID NO: 4 (the SNP sequence) are shown in Table 6. The sequencing data indicates that the third region (Cycle 4 and Cycle 5) of SEQ ID NO: 1 is 3'-CTGAC-5' (SEQ ID NO: 5), and that the third region (Cycle 4 and Cycle 5) of SEQ ID NO: 4 is 3'-CCTGC-5' (SEQ ID NO: 7). The difference between the sequencing data between SEQ ID NO: 1 and SEQ ID NO: 4 indicates the presence of a variant within the second region.

TABLE 6

| | | Cycle | | | | | | | | | | | | | | | | | | | |
|---|---|---|---|---|---|---|---|---|---|---|---|---|---|---|---|---|---|---|---|---|---|
| | | 1 | | | | 2 | | | | 3 | | | | 4 | | | | 5 | | | |
| | | Cycle Step | | | | | | | | | | | | | | | | | | | |
| | | 1 | 2 | 3 | 4 | 1 | 2 | 3 | 4 | 1 | 2 | 3 | 4 | 1 | 2 | 3 | 4 | 1 | 2 | 3 | 4 |
| | | Flow Bases | | | | | | | | | | | | | | | | | | | |
| | | First Region | | | | Second Region (Fast-Forward Region) | | | | | | | | Third Region | | | | | | | |
| | | A | C | T | G | C/T/G | A/T/G | A/C/G | A/C/T | C/T/G | A/T/G | A/C/G | A/C/T | A | C | T | G | A | C | T | G |
| SEQ ID NO: 4 | Number of Bases Incorporated | 1 | 1 | 1 | 1 | 0 | 2 | 1 | 3 | 1 | 1 | 1 | 5 | 0 | 0 | 0 | 2 | 1 | 1 | 0 | 1 |
| | Base(s) Incorporated | A | C | T | G | — | AA | C | TTA | G | A | C | TATAC (SEQ ID NO: 6) | — | — | — | GG | A | C | — | G |
| SEQ ID NO: 1 | Number of Bases Incorporated | 1 | 1 | 1 | 1 | 0 | 2 | 1 | 3 | 4 | 3 | 6 | 2 | 0 | 0 | 0 | 1 | 1 | 1 | 1 | 1 |
| | Base(s) Incorporated | A | C | T | G | — | AA | C | TTA | GGCT (SEQ ID NO: 2) | ATA | CGGACG (SEQ ID NO: 3) | TC | — | — | — | G | A | C | T | G |

SEQ ID NO: 4: 3'-TGACTTGAATCTGATATGCCTGCAGCTGAC-5'

SEQ ID NO: 1: 3'-TGACTTGAATCCGATATGCCTGCAGCTGAC-5'

TABLE 7

| | | Cycle | | | | | | | | | | | | |
|---|---|---|---|---|---|---|---|---|---|---|---|---|---|---|
| | | 1 | | | | 2 | | | | 3 | | | | 4 5 |
| | | Cycle Step | | | | | | | | | | | | |
| | | 1 | 2 | 3 | 4 | 1 | 2 | 3 | 4 | 1 | 2 | 3 | 4 | 1 2 3 4 1 2 3 4 |
| | | Flow Bases | | | | | | | | | | | | |
| | | | | | | Second Region (Fast-Forward Region) | | | | | | | | |
| | | First Region | | | | C/T/ | A/T/ | A/C/ | A/C/ | | A/T/ | | A/C/ | Third Region |
| | | A | C | T | G | G | G | G | T | C/T/G | G | A/C/G | T | A C T G A C T G |
| SEQ ID NO: 8 | Number of Bases Incorporated | 1 | 1 | 1 | 1 | 0 | 2 | 1 | 3 | 4 | 3 | 6 | 2 | 0 0 0 1 0 0 1 0 |
| | Base(s) Incorporated | A | C | T | G | - | AA | C | TTA | GGCT (SEQ ID NO: 2) | ATA | CGGACG (SEQ ID NO: 3) | TA | — — — G — — T — |
| SEQ ID NO: 1 | Number of Bases Incorporated | 1 | 1 | 1 | 1 | 0 | 2 | 1 | 3 | 4 | 3 | 6 | 2 | 0 0 0 1 1 1 1 1 |
| | Base(s) Incorporated | A | C | T | G | - | AA | C | TTA | GGCT (SEQ ID NO: 2) | ATA | CGGACG (SEQ ID NO: 3) | TC | — — — G A C T G |

SEQ ID NO: 8: 3'-TGACTTGAATCCGATATGCCTGCATCAGCTGAC-5'
SEQ ID NO: 1: 3'-TGACTTGAATCCGATATGCCTGCAGCTGAC-5'

TABLE 8

| | | Cycle | | | | | | | | | | | | |
|---|---|---|---|---|---|---|---|---|---|---|---|---|---|---|
| | | 1 | | | | 2 | | | | 3 | | | | 4 5 |
| | | Cycle Step | | | | | | | | | | | | |
| | | 1 | 2 | 3 | 4 | 1 | 2 | 3 | 4 | 1 | 2 | 3 | 4 | 1 2 3 4 1 2 3 4 |
| | | Flow Bases | | | | | | | | | | | | |
| | | | | | | Second Region (Fast-Forward Region) | | | | | | | | |
| | | First Region | | | | C/T/ | A/T/ | A/C/ | A/C/ | | A/T/ | | A/C/ | Third Region |
| | | A | C | T | G | G | G | G | T | C/T/G | G | A/C/G | T | A C T G A C T G |
| SEQ ID NO: 9 | Number of Bases Incorporated | 1 | 1 | 1 | 1 | 0 | 2 | 1 | 3 | 4 | 3 | 4 | 0 | 0 0 1 1 0 0 0 0 |
| | Base(s) Incorporated | A | C | T | G | — | AA | C | TTA | GGCT (SEQ ID NO: 2) | ATA | CGAC (SEQ ID NO: 11) | — | — — T G — — — — |
| SEQ ID NO: 1 | Number of Bases Incorporated | 1 | 1 | 1 | 1 | 0 | 2 | 1 | 3 | 4 | 3 | 6 | 2 | 0 0 0 1 1 1 1 1 |
| | Base(s) Incorporated | A | C | T | G | — | AA | C | TTA | GGCT (SEQ ID NO: 2) | ATA | CGGACG (SEQ ID NO: 3) | TC | — — — G A C T G |

SEQ ID NO: 9: 3'-TGACTTGAATCCGATATGCTGAC-5'
SEQ ID NO: 1: 3'-TGACTTGAATCCGATATGCCTGCAGCTGAC-5'

TABLE 9

| | | Cycle | | | | | | | | | | | | | | | | | | | |
|---|---|---|---|---|---|---|---|---|---|---|---|---|---|---|---|---|---|---|---|---|---|
| | | 1 | | | | 2 | | | | 3 | | | | 4 | | | | 5 | | | |
| | | Cycle Step | | | | | | | | | | | | | | | | | | | |
| | | 1 | 2 | 3 | 4 | 1 | 2 | 3 | 4 | 1 | 2 | 3 | 4 | 1 | 2 | 3 | 4 | 1 | 2 | 3 | 4 |
| | | Flow Bases | | | | | | | | | | | | | | | | | | | |
| | | First Region | | | | Second Region (Fast-Forward Region) | | | | | | | | Third Region | | | | | | | |
| | | A | C | T | G | C/T/G | A/T/G | A/C/G | A/C/T | C/T/G | A/T/G | A/C/G | A/C/T | A | C | T | G | A | C | T | G |
| SEQ ID NO: 12 | Number of Bases Incorporated | 1 | 1 | 1 | 1 | 0 | 2 | 1 | 3 | 4 | 5 | 9 | 1 | 0 | 0 | 0 | 1 | 0 | 0 | 0 | 0 |
| | Base(s) Incorporated | A | C | T | G | — | AA | C | TTA | GGCT (SEQ ID NO: 2) | ATATG (SEQ ID NO: 10) | CAGGCCGAC (SEQ ID NO: 14) | T | — | — | — | G | — | — | — | — |
| SEQ ID NO: 1 | Number of Bases Incorporated | 1 | 1 | 1 | 1 | 0 | 2 | 1 | 3 | 4 | 3 | 6 | 2 | 0 | 0 | 0 | 1 | 1 | 1 | 1 | 1 |
| | Base(s) Incorporated | A | C | T | G | — | AA | C | TTA | GGCT (SEQ ID NO: 2) | ATA | CGGACG (SEQ ID NO: 3) | TC | — | — | — | G | A | C | T | G |

SEQ ID NO: 12: 3'-TGACTTGAATCCGATATACGTCCGGCTGAC-5'
SEQ ID NO: 1: 3'-TGACTTGAATCCGATATGCCTGCAGCTGAC-5'

Example 3

Detection of a variant within SEQ ID NO: 8 (which includes an ATC insert following base position 23 relative to the reference sequence SEQ ID NO: 1) is described in this example. A coupled sequencing read pair can be generated for SEQ ID NO: 1 and SEQ ID NO: 8 using a flow sequencing method that includes a fast forward portion through a second region. In this example, 5 cycles are used, with Cycle 1 being used to extend the primer through the first region, Cycle 2 and Cycle 3 being used to extend the primer through the second region, and Cycle 4 and Cycle 5 being used to extend the primer through the third region. Cycle 1, Cycle 4, and Cycle 5 use labeled nucleotides to extend the primer, and the incorporation of a nucleotide into the primer is detected after each cycle step. In contrast, incorporation of a nucleotide into the primer may be skipped during Cycle 2 and Cycle 3. Each cycle has 4 steps, with Cycles 1, 4, and 5 include the sequential and independent addition of A-C-T-G labeled nucleotides, with a single base type being added at each cycle step, and incorporation of a labeled nucleotide being detected after each step. Cycle 2 and Cycle 3 are implemented in a "fast forward" mode, and include 4 cycle steps, wherein Step 1 omits A nucleotides (i.e., includes C, T, and G), Step 2 omits, C nucleotides (i.e., includes A, T, and G), Step 3 omits T nucleotides (i.e., includes A, C, and G), and Step 4 omits G nucleotides (i.e., includes A, C, and T). Nucleotide incorporation is not detected during the fast forward mode of Cycle 2 and Cycle 3. Because Cycles 2 and 3 include multiple different nucleotide base types simultaneously during primer extension, the primer is extended faster than if only a single base type was used at any given step. The flowgrams for SEQ ID NO: 1 (the reference sequence) and SEQ ID NO: 8 are shown in Table 7. The sequencing data indicates that the third region (Cycle 4 and Cycle 5) of SEQ ID NO: 1 is 3'-CTGAC-5' (SEQ ID NO: 5), and that the third region (Cycle 4 and Cycle 5) of SEQ ID NO: 8 is 3'-AC-5'. The difference between the sequencing data between SEQ ID NO: 1 and SEQ ID NO: 8 indicates the presence of a variant within the second region.

Example 4

Detection of a variant within SEQ ID NO: 9 (which includes a deletion of the GCCTGCA (SEQ ID NO: 13) bases following base position 17 relative to reference sequence SEQ ID NO: 1) is described in this example. A coupled sequencing read pair can be generated for SEQ ID NO: 1 and SEQ ID NO: 9 using a flow sequencing method that includes a fast forward portion through a second region. In this example, 5 cycles are used, with Cycle 1 being used to extend the primer through the first region, Cycle 2 and Cycle 3 being used to extend the primer through the second region, and Cycle 4 and Cycle 5 being used to extend the primer through the third region. Cycle 1, Cycle 4, and Cycle 5 use labeled nucleotides to extend the primer, and the incorporation of a nucleotide into the primer is detected after each cycle step. In contrast, incorporation of a nucleotide into the primer may be skipped during Cycle 2 and Cycle 3. Each cycle has 4 steps, with Cycles 1, 4, and 5 include the sequential and independent addition of A-C-T-G labeled nucleotides, with a single base type being added at each cycle step, and incorporation of a labeled nucleotide being detected after each step. Cycle 2 and Cycle 3 are implemented in a "fast forward" mode, and include 4 cycle steps, wherein Step 1 omits A nucleotides (i.e., includes C, T, and G), Step 2 omits, C nucleotides (i.e., includes A, T, and G), Step 3 omits T nucleotides (i.e., includes A, C, and G), and Step 4 omits G nucleotides (i.e., includes A, C, and T). Nucleotide incorporation is not detected during the fast forward mode of Cycle 2 and Cycle 3. Because Cycles 2 and 3 include multiple different nucleotide base types simultaneously during primer extension, the primer is extended faster than if only a single base type was used at any given step. The flowgrams for SEQ ID NO: 1 (the reference sequence) and SEQ ID NO: 9 are shown in Table 8. The sequencing data indicates that the third region (Cycle 4 and Cycle 5) of SEQ ID NO: 1 is 3'-CTGAC-5' (SEQ ID NO: 5), and that the third region (Cycle 4 and Cycle 5) of SEQ ID NO: 9 is 3'-AC-5'. The difference between the sequencing data between SEQ ID NO: 1 and SEQ ID NO: 8 indicates the presence of a variant within the second region.

Example 5

Detection of a variant within SEQ ID NO: 12 (which includes an inversion of bases GCCTGCA (SEQ ID NO: 13) bases following base position 17 relative to reference sequence SEQ ID NO: 1) is described in this example. A coupled sequencing read pair can be generated for SEQ ID NO: 1 and SEQ ID NO: 12 using a flow sequencing method that includes a fast forward portion through a second region. In this example, 5 cycles are used, with Cycle 1 being used to extend the primer through the first region, Cycle 2 and Cycle 3 being used to extend the primer through the second region, and Cycle 4 and Cycle 5 being used to extend the primer through the third region. Cycle 1, Cycle 4, and Cycle 5 use labeled nucleotides to extend the primer, and the incorporation of a nucleotide into the primer is detected after each cycle step. In contrast, incorporation of a nucleotide into the primer may be skipped during Cycle 2 and Cycle 3. Each cycle has 4 steps, with Cycles 1, 4, and 5 include the sequential and independent addition of A-C-T-G labeled nucleotides, with a single base type being added at each cycle step, and incorporation of a labeled nucleotide being detected after each step. Cycle 2 and Cycle 3 are implemented in a "fast forward" mode, and include 4 cycle steps, wherein Step 1 omits A nucleotides (i.e., includes C, T, and G), Step 2 omits, C nucleotides (i.e., includes A, T, and G), Step 3 omits T nucleotides (i.e., includes A, C, and G), and Step 4 omits G nucleotides (i.e., includes A, C, and T). Nucleotide incorporation is not detected during the fast forward mode of Cycle 2 and Cycle 3. Because Cycles 2 and 3 include multiple different nucleotide base types simultaneously during primer extension, the primer is extended faster than if only a single base type was used at any given step. The flowgrams for SEQ ID NO: 1 (the reference sequence) and SEQ ID NO: 12 are shown in Table 9. The sequencing data indicates that the third region (Cycle 4 and Cycle 5) of SEQ ID NO: 1 is 3'-CTGAC-5' (SEQ ID NO: 5), and that the third region (Cycle 4 and Cycle 5) of SEQ ID NO: 12 is 3'-G-5'. The difference between the sequencing data between SEQ ID NO: 1 and SEQ ID NO: 12 indicates the presence of a variant within the second region.

Example 6

Figure 20:
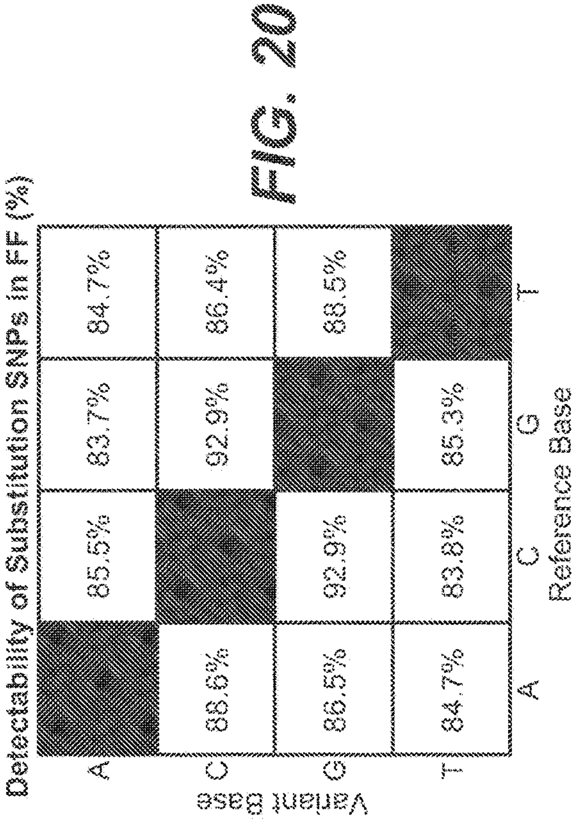
FIG. 20 shows a matrix showing the base detection sensitivity for various SNP variants detected using a simulated fast forward sequencing protocol, wherein the second regions of the synthetic polynucleotides are sequenced using a repeated four-step flow cycle, each flow having a single nucleotide base.

To test sensitivity of fast forward sequencing to detect SNPs, the sequencing method was simulated in silico to sequence Approximately 1.14 million synthetic nucleic acid molecules within the hg38 reference genome, each synthetic nucleic acid molecule being a 2 kilobase segment with a random starting point within the reference genome. 502 bp segments from each synthetic sequencing read was generated, and all three possible single base mutations queried at each base within the ~502 bp segment (i.e., a total of 500×~1.14M×3 possible variants (i.e., ABC→ADC, wherein B/D)) were queried for SNP detection. For each SNP variant ABC→ADC, the SNP was considered non-detectable when (A=B and D=C) or (A=D and B=C), as neither SNP would generate a new zero or new non-zero signal in a flowgram. A matrix of variant base to reference base detection sensitivity is shown in FIG. 20.

Figure 21A:
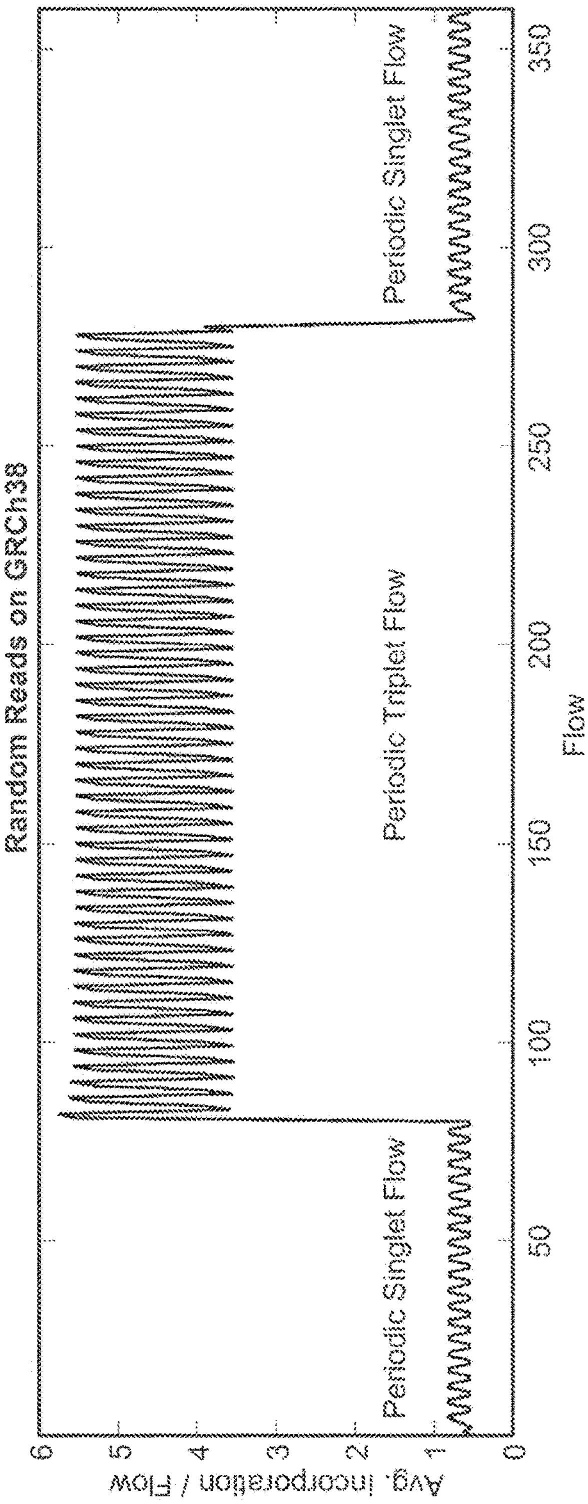
FIG. 21A shows average base incorporation across the flows in the first, second and third regions for a simulated fast-forward sequencing protocol using a repeated four-step flow cycle, wherein each flow includes a mixture of three different nucleotide bases. A matrix of variant base to reference base detection sensitivity is shown in FIG. 21B.
Figure 21B:
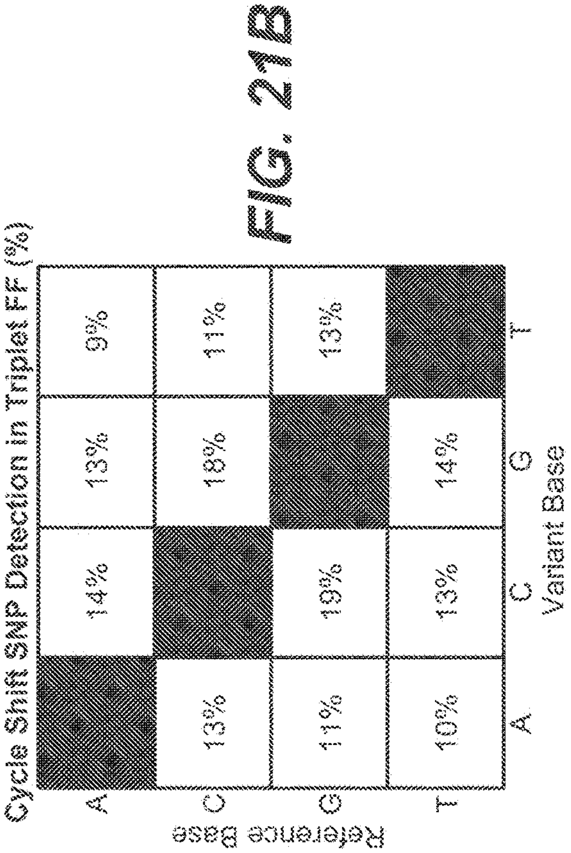
FIG. 21C shows the distribution of base coverage across the synthetic reads.
Figure 21C:
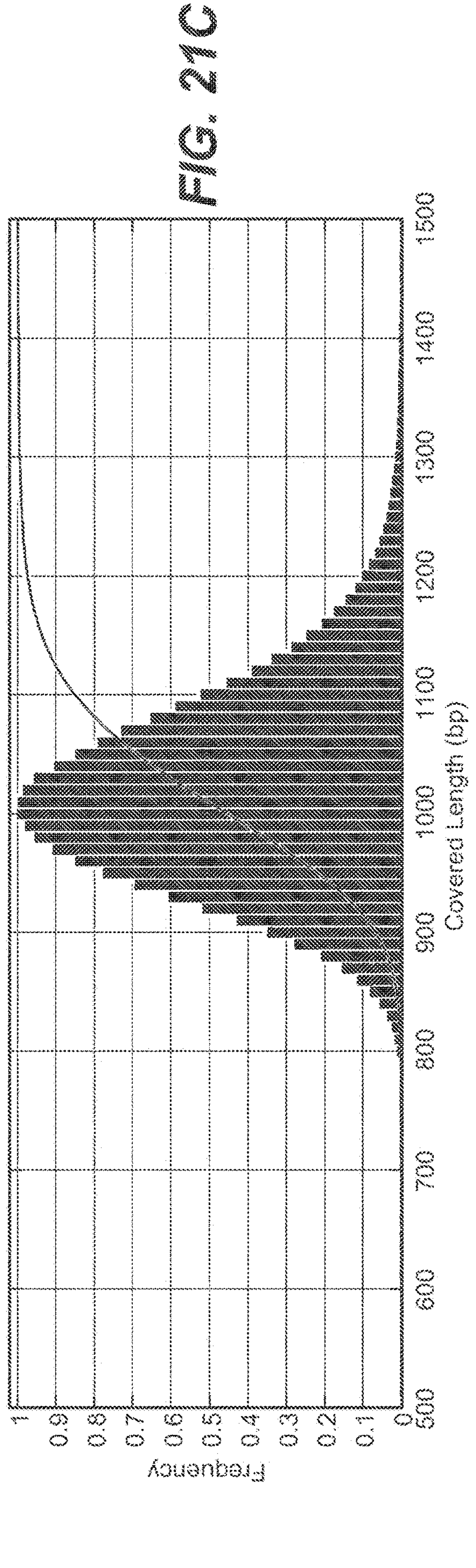

The synthetic nucleic acid molecules were then sequenced in silico using a four-step flow cycle, where each flow included a mixture of three nucleotides in a middle (second) region. The first regions of the synthetic nucleic acid molecules were sequenced using 80 nucleotide flows according to a four-step flow cycle, wherein each step included a single nucleotide base type. The sequencing primer extended across 54±7 bases in the 80 flows in the first region (~0.675 bases per flow). The second regions of the synthetic nucleic acid molecules were sequenced using 200 nucleotides according to a four-step flow cycle, wherein each step included three and omitted one nucleotide base type (i.e., (i) A, C, T, and not G; (ii) G, A, C, and not T; (iii) T, G, A, and not C; and (iv) C, T, G, and not A). The sequencing primer extended across 915±89 bases in the 200 flows in the second region (~4.575 bases per flow). The third regions of the synthetic nucleic acid molecules were sequenced using 80 nucleotide flows according to a four-step flow cycle, wherein each step included a single nucleotide base type. The sequencing primer extended across 54±7 bases in the 80 flows in the third region (~0.675 bases per flow). The flowgram of the third (downstream) region for each synthetic variant nucleic acid molecule was compared to the flowgram of the third region for a corresponding synthetic wild-type nucleic acid molecule. A new non-zero flowgram entry and/or a new zero flowgram entry in the third region of the synthetic variant nucleic acid molecule, compared to the corresponding synthetic wild-type nucleic acid molecule, indicated detection of the SNP introduced into the second region. FIG. 21A shows average base incorporation across the flows in the first, second and third regions. A matrix of variant base to reference base detection sensitivity is shown in FIG. 21B. FIG. 21C shows the distribution of base coverage across the synthetic reads.

Example 7

Polynucleotides in a sequencing library with an average insert length of 450 bases (and an approximate range between 300 and 600 bases) are attached to beads and amplified to generate sequencing clusters on the beads. The polynucleotides in the sequencing clusters are then hybridized to sequencing primers and subjected to flow sequencing using 400 single nucleotide flows according to a four step flow cycle. Each nucleotide flow contains a single base type, and a portion of the nucleotides are labeled. After each flow, the inserts are imaged to detect the presence or absence of an incorporated nucleotide, thereby generating sequencing data for the inserts. The label from the incorporated nucleotides is also cleaved and washed away. The average number of bases incorporated per flow is approximately 0.76 (based on the distribution of bases in the human genome), and the average expected sequencing region is about 300 bases in length.

The sequencing primers are then extended using 20 cycles in a fast-forward region, wherein each cycle contains four flow steps, each flow step containing three different base types (i.e., "triplet" flows, e.g. a "not-A" flow that includes C, G, and T nucleotides; a "not-C" flow that includes A, G, and T nucleotides; a "not-G" flow that includes A, C, and T nucleotides; or a "not-T" flow that includes A, C, and G nucleotides). On average, approximately 4.5 bases are incorporated into the sequencing strand per triplet flow, as approximated using the distribution of bases in the human genome. A portion of the nucleotides in each triplet flow are labeled. The portion of labeled nucleotides used in the triplet flows is approximately 0.2-0.25 of the portion of labeled nucleotides used during sequencing. After every four flows, the inserts are imaged to detect a signal from the incorporated labeled nucleotide, and the labels of the nucleotides are cleaved and washed away. With an average incorporation rate of 4.5 bases per flow, the detected signal is expected to indicate the incorporation of 18 bases after the four triplet flows. Using this expectation, the average fast-forward region is expected to be approximately 360 bases in length. Since the average insert length is approximately 450 bases in length, ranging from 300 bases to 600 bases, it is expected that a portion of the inserts may be entirely covered by the sequencing region (that is, the sequencing primer would have been fully extended to the end of the insert prior to the start of the fast-forward flows), and that all or nearly all of the inserts would be covered by the end of the fast-forward flows.

Some clusters may fail during sequencing, for example due to a large portion of polynucleotides within the cluster failing to extend the complementary sequencing primer ("droop strands") or substantial and rapid signal decay. Insert length for these inserts cannot be determined. For the remaining beads, the first imaging signal with no new nucleotide incorporation signal (i.e., the signal from this image and images onward are approximately constant and close to zero) are used to define the previous flow as $F_{last}$. That is, $F_{last}$ is the final flow in which a signal was detected indicating incorporation of a nucleotide into the extending sequencing primer.

If $F_{last}$ is a flow in the standard sequencing region (i.e., a single nucleotide flow), the length of the insert is defined by the called sequence. If $F_{last}$ is within the fast-forward region, the following algorithm is used to determine the insert length:

First, for each cluster (bead), a normalized signal per base within the fast-forward region is determined using the last 20 similar sequencing flows (i.e., single nucleotide flows in the sequencing region) to provide a signal for each fast-forward flow type (e.g., not-A, not-C, not-G, or not-T). For example, for a normalized signal per base for a not-A flow, nucleotide incorporation signal from the last 20 sequencing single nucleotide flows that contained C, G, or T nucleotides (not A nucleotides) is summed and divided by the number of bases called in those flows. For a normalized signal per base for a not-C flow, nucleotide incorporation signal from the last 20 sequencing single nucleotide flows that contained A, G, or T nucleotides (not C nucleotides) is summed and divided by the number of bases called in those flows. For a normalized signal per base for a not-G flow, nucleotide incorporation signal from the last 20 sequencing single nucleotide flows that contained A, C, or T nucleotides (not G nucleotides) is summed and divided by the number of bases called in those flows. For a normalized signal per base for a not-T flow, nucleotide incorporation signal from the last 20 sequencing single nucleotide flows that contained A, C, or G nucleotides (not T nucleotides) is summed and divided by the number of bases called in those flows. This normalized signal per base for each fast-forward flow type is determined per bead do normalize bead-specific properties, such as the number of polynucleotide copies in the cluster, the location of the cluster on the sequencing substrate, and the percentage of failed polynucleotides (i.e. "droops") in the cluster.

Second, the signal for a given fast-forward cycle (i.e., the set of four triplet flows) for a particular sequencing cluster (bead) is divided by the signal by the average normalized signal per base (i.e., the average of the normalized not-A signal per base, normalized not-C signal per base, normalized not-G signal per base, and normalized not-T signal per base) to determine the number of bases incorporated into the sequencing primer during that cycle for that sequencing cluster.

Third, the number of bases incorporated into the sequencing primer during any given cycle is corrected to account for droop strands (i.e., sequencing primers that failed to extend as expected) in the cluster. An expected number of bases per fast-forward cycle (e.g., approximately 18 bases per cycle) can be used along with the average number of bases incorporated into a sequencing primer during that cycle across all beads. That is, the corrected number (B) of bases incorporated into a sequencing primer for cluster i during cycle j is determined as:

$$B_{i,j} = \frac{N_{i,j}E}{AvgN_j}$$

wherein $B_{i,j}$ is a corrected number of bases incorporated into the sequencing primer during cycle i for cluster j; $N_{i,j}$ is the uncorrected number of bases incorporated into the sequencing primer during cycle i for cluster j; E is the expected number of bases incorporated into a sequencing primer during a cycle; and $AvgN_j$ is the average uncorrected number of bases incorporated into the sequencing primer during cycle i across all clusters in the run.

The length of the fast-forward region for the polynucleotide of a given cluster is then the sum of the corrected number of bases incorporated into the sequencing primmer across all fast-forward cycles (until Fast), and the length of the insert as a whole is the sum of the length of the fast-forward region and the sequencing region.

Figure 22B:
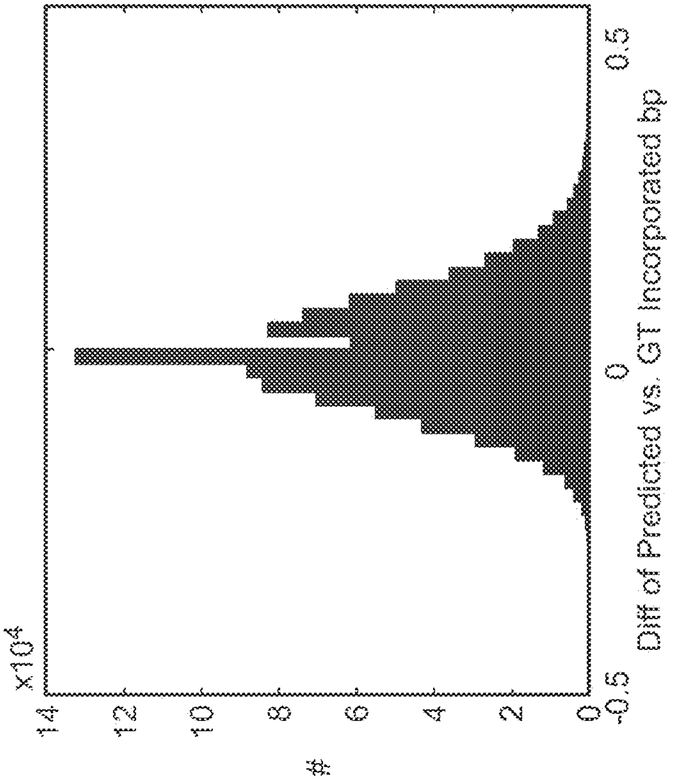
FIG. 22B shows a histogram of the difference of the predicted insert length from the ground truth, with 76% of the estimated lengths deviating from the ground truth by less than 10%.
Figure 22A:
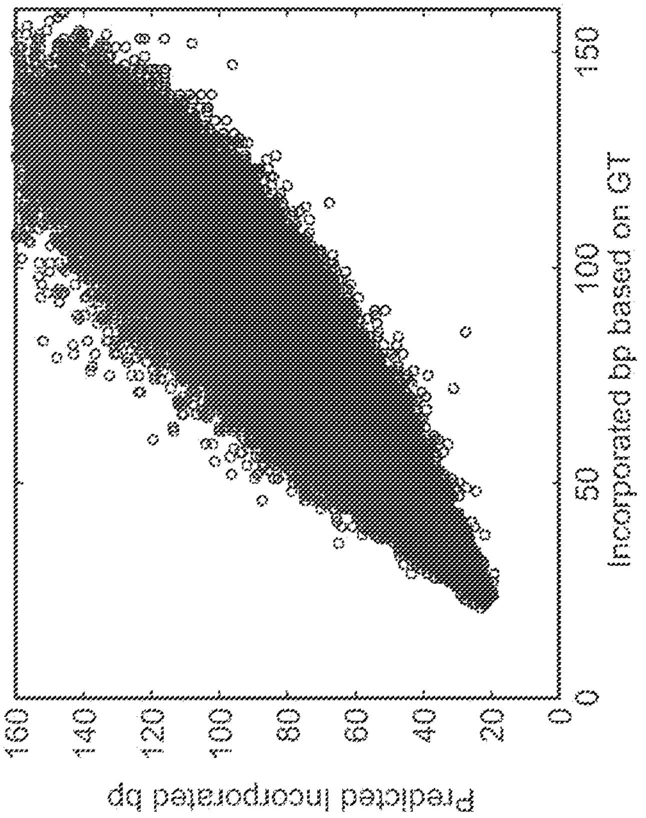
FIG. 22A shows the comparison of a predicted insert length to a ground truth sequence length, demonstrating a high correlation with an $r^2$ of 0.939.

To validate the algorithm, 1 million reads from a standard sequencing run were simulated with cycles of four triplet flows. The signal from single nucleotide flows was summed to simulate a triplet flow. The length of the insert, as simulated, was determined using the algorithm discussed above and compared to a ground truth from the original sequencing read from flows 161 to 320. The average polynucleotide length from these flows (ground truth) was 72.7 bases, which correlated with the predicted length with an $r^2$ of 0.939. See FIG. 22A and FIG. 22B. Further, 76% of the estimated lengths deviate from the ground truth by 10% or less.

What is claimed is:

1. A method for sequencing, comprising:

(a) providing a nucleic acid molecule comprising a first region and a second region;

(b) sequencing the first region by, in each flow step of a plurality of first flow cycles, incorporating a labeled nucleotide into a primer hybridized to the nucleic acid molecule and detecting the labeled nucleotide incorporated into the primer, or detecting a lack of incorporation thereof into the primer; and (c) determining distance information for the second region by, (i) in each flow step of a plurality of second flow cycles, providing a plurality of nucleotides to the primer, wherein, during the plurality of second flow cycles, one or more labeled nucleotides are incorporated into the primer, (ii) subsequent to at least two or more flow steps of the plurality of second flow cycles, detecting one or more signals from one or more labeled nucleotides incorporated into the primer, or detecting lack of incorporation thereof into the primer, without detecting the one or more signals from the one or more labeled nucleotides incorporated into the primer, or the lack of incorporation thereof, between at least two or more flow steps in the plurality of second flow cycles, and (iii) determining distance information indicative of a length of the second region based at least in part on a relationship between an intensity of the one or more signals and a distance.

2. The method of claim 1, wherein at least one of the at least two or more flow steps comprises a simultaneous use of two or more different nucleotide bases.

3. The method of claim 1, wherein at least one of the at least two or more flow steps comprises a simultaneous use of three or more different nucleotide bases.

4. The method of claim 1, wherein, in (c), the primer is extended through the second region without detecting incorporated labeled nucleotides after each flow step in the plurality of second flow cycles.

5. The method of claim 1, wherein a label of the one or more labeled nucleotides incorporated in (c) is not cleaved after each flow step in the plurality of second flow cycles.

6. The method of claim 1, wherein (c) comprises measuring a plurality of signals, wherein a signal of the plurality of signals is measured after every two to five flow steps of the plurality of second flow cycles and determining the distance information based at least in part on the plurality of signals.

7. The method of claim 6, further comprising, subsequent to measuring the signal after the every two to five flow steps, cleaving one or more labels from labeled nucleotides incorporated in the primer.

8. The method of claim 1, wherein the plurality of nucleotides comprises a mixture of unlabeled nucleotides and labeled nucleotides.

9. The method of claim 1, wherein a first portion of the at least two or more flow steps comprises use of only unlabeled nucleotides and a second portion of the at least two or more flow steps comprises use of labeled nucleotides.

10. The method of claim 9, wherein the second portion of the at least two or more flow steps comprises a simultaneous use of labeled nucleotides and unlabeled nucleotides.

11. The method of claim 1, wherein each of the at least two or more flow steps comprises a simultaneous use of labeled and unlabeled nucleotides.

12. The method of claim 1, further comprising, subsequent to detecting the one or more signals, cleaving a label of the one or more labeled nucleotides.

13. The method of claim 1, wherein the primer is extended through the first region before being extended through the second region.

14. The method of claim 1, wherein the primer is extended through the second region prior to being extended through the first region.

15. The method of claim 1, wherein determining the distance information comprises determining a normalized signal per base incorporated into the primer, and determining a number of bases incorporated into the primer using the one or more signals and the normalized signal per base.

16. The method of claim 1, further comprising characterizing the nucleic acid molecule as a duplicate of another nucleic acid molecule or a unique nucleic acid molecule using the distance information.

17. The method of claim 1, further comprising sequencing a third region of the nucleic acid molecule by, in each flow step of a plurality of third flow cycles, incorporating a given labeled nucleotide into the primer and detecting the given labeled nucleotide, or detecting a lack of incorporation thereof into the primer, wherein the second region is between the first region and the third region, thereby generating a coupled sequencing read pair.

18. The method of claim 17, further comprising determining expected sequencing data for the second region using a reference sequence and a second flow order of the plurality of second flow cycles.

19. The method of claim 17, further comprising determining expected sequencing data for the third region using a reference sequence for the second region, a second flow order of the plurality of second flow cycles, a reference sequence for the third region, and a third flow order of the plurality of third flow cycles.

20. The method of claim 17, further comprising determining expected test variant sequencing data for the second region using a second flow order of the plurality of second flow cycles and a second reference sequence for the second region, wherein the second reference sequence comprises a test variant.

21. The method of claim 20, further comprising determining expected test variant sequencing data for the third region using the second reference sequence for the second region, the second flow order, a reference sequence for the third region, and a third flow order of the plurality of third flow cycles.

* * * * *

SEQUENCE LISTING

```
<160> NUMBER OF SEQ ID NOS: 22

<210> SEQ ID NO 1
<211> LENGTH: 30
<212> TYPE: DNA
<213> ORGANISM: Artificial Sequence
```

<220> FEATURE:
<223> OTHER INFORMATION: Synthetic Construct

<400> SEQUENCE: 1
cagtcgacgt ccgtatagcc taagttcagt 30

<210> SEQ ID NO 2
<211> LENGTH: 4
<212> TYPE: DNA
<213> ORGANISM: Artificial Sequence
<220> FEATURE:
<223> OTHER INFORMATION: Synthetic Construct

<400> SEQUENCE: 2 ggct 4

<210> SEQ ID NO 3
<211> LENGTH: 6
<212> TYPE: DNA
<213> ORGANISM: Artificial Sequence
<220> FEATURE:
<223> OTHER INFORMATION: Synthetic Construct

<400> SEQUENCE: 3 cggacg 6

<210> SEQ ID NO 4
<211> LENGTH: 30
<212> TYPE: DNA
<213> ORGANISM: Artificial Sequence
<220> FEATURE:
<223> OTHER INFORMATION: Synthetic Construct

<400> SEQUENCE: 4
cagtcgacgt ccgtatagtc taagttcagt 30

<210> SEQ ID NO 5
<211> LENGTH: 5
<212> TYPE: DNA
<213> ORGANISM: Artificial Sequence
<220> FEATURE:
<223> OTHER INFORMATION: Synthetic Construct

<400> SEQUENCE: 5 cagtc 5

<210> SEQ ID NO 6
<211> LENGTH: 5
<212> TYPE: DNA
<213> ORGANISM: Artificial Sequence
<220> FEATURE:
<223> OTHER INFORMATION: Synthetic Construct

<400> SEQUENCE: 6 tatac 5

<210> SEQ ID NO 7
<211> LENGTH: 5
<212> TYPE: DNA
<213> ORGANISM: Artificial Sequence
<220> FEATURE:
<223> OTHER INFORMATION: Synthetic Construct

<400> SEQUENCE: 7 cgtcc 5

<210> SEQ ID NO 8
<211> LENGTH: 33
<212> TYPE: DNA
<213> ORGANISM: Artificial Sequence
<220> FEATURE:
<223> OTHER INFORMATION: Synthetic Construct

<400> SEQUENCE: 8
cagtcgacta cgtccgtata gcctaagttc agt 33

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
cagtcgtata gcctaagttc agt 23

<210> SEQ ID NO 10
<211> LENGTH: 5
<212> TYPE: DNA
<213> ORGANISM: Artificial Sequence
<220> FEATURE:
<223> OTHER INFORMATION: Synthetic Construct

<400> SEQUENCE: 10 atatg 5

<210> SEQ ID NO 11
<211> LENGTH: 4
<212> TYPE: DNA
<213> ORGANISM: Artificial Sequence
<220> FEATURE:
<223> OTHER INFORMATION: Synthetic Construct

<400> SEQUENCE: 11 cgac 4

<210> SEQ ID NO 12
<211> LENGTH: 30
<212> TYPE: DNA
<213> ORGANISM: Artificial Sequence
<220> FEATURE:
<223> OTHER INFORMATION: Synthetic Construct

<400> SEQUENCE: 12
cagtcggcct gcatatagcc taagttcagt 30

<210> SEQ ID NO 13
<211> LENGTH: 7
<212> TYPE: DNA
<213> ORGANISM: Artificial Sequence
<220> FEATURE:
<223> OTHER INFORMATION: Synthetic Construct

<400> SEQUENCE: 13 gcctgca 7

<210> SEQ ID NO 14
<211> LENGTH: 9
<212> TYPE: DNA
<213> ORGANISM: Artificial Sequence
<220> FEATURE:
<223> OTHER INFORMATION: Synthetic Construct

<400> SEQUENCE: 14 caggccgac 9

<210> SEQ ID NO 15
<211> LENGTH: 12
<212> TYPE: DNA
<213> ORGANISM: Artificial Sequence
<220> FEATURE:
<223> OTHER INFORMATION: Synthetic Construct

<400> SEQUENCE: 15
tatggtcgtc ga 12

<210> SEQ ID NO 16
<211> LENGTH: 12
<212> TYPE: DNA
<213> ORGANISM: Artificial Sequence
<220> FEATURE:
<223> OTHER INFORMATION: Synthetic Construct

<400> SEQUENCE: 16
tatggtcatc ga 12

<210> SEQ ID NO 17
<211> LENGTH: 12
<212> TYPE: DNA
<213> ORGANISM: Artificial Sequence
<220> FEATURE:
<223> OTHER INFORMATION: Synthetic Construct

<400> SEQUENCE: 17
tggtcgtcga gc 12

<210> SEQ ID NO 18
<211> LENGTH: 12
<212> TYPE: DNA
<213> ORGANISM: Artificial Sequence
<220> FEATURE:
<223> OTHER INFORMATION: Synthetic Construct

<400> SEQUENCE: 18
tatatggtcg tc 12

<210> SEQ ID NO 19
<211> LENGTH: 19
<212> TYPE: DNA
<213> ORGANISM: Artificial Sequence
<220> FEATURE:
<223> OTHER INFORMATION: Synthetic Construct

<400> SEQUENCE: 19
tatatggtca tcgagctat 19

<210> SEQ ID NO 20
<211> LENGTH: 19
<212> TYPE: DNA
<213> ORGANISM: Artificial Sequence
<220> FEATURE:
<223> OTHER INFORMATION: Synthetic Construct

<400> SEQUENCE: 20
tatatggtcg tcgagctat 19

<210> SEQ ID NO 21

-continued

```
<211> LENGTH: 12
<212> TYPE: DNA
<213> ORGANISM: Artificial Sequence
<220> FEATURE:
<223> OTHER INFORMATION: Synthetic Construct

<400> SEQUENCE: 21

tatggtcgtc ga                                                          12


<210> SEQ ID NO 22
<211> LENGTH: 12
<212> TYPE: DNA
<213> ORGANISM: Artificial Sequence
<220> FEATURE:
<223> OTHER INFORMATION: Synthetic Construct

<400> SEQUENCE: 22

tatggtcgat cg                                                          12
```